(12) United States Patent
Giurleo et al.

(10) Patent No.: US 12,077,587 B2
(45) Date of Patent: *Sep. 3, 2024

(54) ANTI-CD8 ANTIBODIES AND USES THEREOF

(71) Applicant: Regeneron Pharmaceuticals, Inc., Tarrytown, NY (US)

(72) Inventors: Jason T. Giurleo, Franklin Lakes, NJ (US); Dangshe Ma, Millwood, NY (US); William Olson, Yorktown Heights, NY (US); Gavin Thurston, Briarcliff Manor, NY (US); Richard Tavare, Croton-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 120 days.

This patent is subject to a terminal disclaimer.

(21) Appl. No.: 18/049,972

(22) Filed: Oct. 26, 2022

(65) Prior Publication Data
US 2023/0159639 A1  May 25, 2023

Related U.S. Application Data

(63) Continuation of application No. 16/914,112, filed on Jun. 26, 2020, now Pat. No. 11,525,001, which is a (Continued)

(51) Int. Cl.
*C07K 16/28* (2006.01)
*A61K 45/06* (2006.01)
(Continued)

(52) U.S. Cl.
CPC .......... *C07K 16/2815* (2013.01); *A61K 45/06* (2013.01); *A61K 49/0032* (2013.01); (Continued)

(58) Field of Classification Search
None
See application file for complete search history.

(56) References Cited

U.S. PATENT DOCUMENTS

| | | |
|---|---|---|
| 4,680,338 A | 7/1987 | Sundoro |
| 5,332,567 A | 7/1994 | Goldenberg |

(Continued)

FOREIGN PATENT DOCUMENTS

| | | |
|---|---|---|
| CN | 104 360 049 | 2/2015 |
| EP | 3266465 | 7/2016 |

(Continued)

OTHER PUBLICATIONS

Petrick et al. (2015) "In Vitro and In Vivo Comparison of Selected Ga-68 and Zr-89 Labelled Siderophores" Mol. Imaging Biol. 18(3):344-352.

(Continued)

*Primary Examiner* — Karl J Puttlitz
(74) *Attorney, Agent, or Firm* — FisherBroyles, LLP; Cara L. Crowley-Weber; Elysa Goldberg

(57) ABSTRACT

Anti-CD8 antibodies, radiolabeled anti-CD8 antibodies, fluorescently labeled anti-CD8 antibodies and their use in imaging are provided herein. Included are methods of detecting the presence of CD8 proteins in a subject or sample.

19 Claims, 13 Drawing Sheets

Specification includes a Sequence Listing.

Related U.S. Application Data continuation of application No. 16/043,048, filed on Jul. 23, 2018, now Pat. No. 10,730,944.

(60) Provisional application No. 62/660,902, filed on Apr. 20, 2018, provisional application No. 62/536,239, filed on Jul. 24, 2017.

(51) Int. Cl.
*A61K 49/00* (2006.01)
*A61K 51/10* (2006.01)
*G01N 33/53* (2006.01)
*A61K 39/00* (2006.01)

(52) U.S. Cl.
CPC ...... *A61K 49/0058* (2013.01); *A61K 51/1027* (2013.01); *C07K 16/2818* (2013.01); *G01N 33/53* (2013.01); *A61K 2039/505* (2013.01); *C07K 2317/21* (2013.01); *C07K 2317/33* (2013.01); *C07K 2317/76* (2013.01); *C07K 2317/92* (2013.01)

(56) References Cited

U.S. PATENT DOCUMENTS

| | | | |
|---|---|---|---|
| 5,639,879 | A | 6/1997 | Mease et al. |
| 6,596,541 | B2 | 7/2003 | Murphy et al. |
| 7,087,411 | B2 | 8/2006 | Daly et al. |
| 8,771,966 | B2 | 7/2014 | Dennis et al. |
| 9,429,584 | B2 | 8/2016 | Matsumura et al. |
| 9,475,874 | B2 | 10/2016 | Sawada et al. |
| 9,546,206 | B2 | 1/2017 | Ring et al. |
| 10,730,944 | B2 | 8/2020 | Giurleo et al. |
| 2002/0106629 | A1 | 8/2002 | Murphy et al. |
| 2004/0018557 | A1 | 1/2004 | Qu et al. |
| 2008/0193376 | A1 | 8/2008 | Tawakol et al. |
| 2008/0260650 | A1 | 10/2008 | Tawakol et al. |
| 2009/0297439 | A1 | 12/2009 | Comoglio et al. |
| 2014/0243504 | A1 | 8/2014 | Davis et al. |
| 2014/0377174 | A1 | 12/2014 | Houthoff et al. |
| 2015/0191543 | A1 | 7/2015 | Wu et al. |
| 2015/0203580 | A1 | 7/2015 | Papadopoulos et al. |
| 2015/0299133 | A1 | 10/2015 | Osterkamp et al. |
| 2016/0000946 | A1 | 1/2016 | Cheng et al. |
| 2016/0151515 | A1 | 6/2016 | Joubert et al. |
| 2017/0029507 | A1 | 2/2017 | Ho et al. |
| 2017/0119913 | A1 | 5/2017 | Osterkamp et al. |
| 2017/0258948 | A1 | 9/2017 | Morin et al. |
| 2017/0283442 | A1 | 10/2017 | D'Souza et al. |
| 2018/0015154 | A1 | 1/2018 | Weichert et al. |
| 2018/0043041 | A1 | 2/2018 | Bansal et al. |
| 2018/0055947 | A1 | 3/2018 | Van Dongen et al. |
| 2018/0078662 | A1 | 3/2018 | Agnew et al. |
| 2018/0126012 | A1 | 5/2018 | Weichert et al. |

FOREIGN PATENT DOCUMENTS

| | | |
|---|---|---|
| WO | 2008124467 | 10/2008 |
| WO | 2009085879 | 7/2009 |
| WO | 2009149382 | 12/2009 |
| WO | 2011056983 | 5/2011 |
| WO | 2011153346 | 12/2011 |
| WO | 2012087962 | 6/2012 |
| WO | 2013138696 | 9/2013 |
| WO | 2013149159 | 10/2013 |
| WO | 2013165940 | 11/2013 |
| WO | 2013177055 | 11/2013 |
| WO | 2014025828 | 2/2014 |
| WO | 2014159087 | 10/2014 |
| WO | 2014159835 | 10/2014 |
| WO | 2014164553 | 10/2014 |
| WO | 2014200969 | 12/2014 |
| WO | 2014210064 | 12/2014 |
| WO | 2015053871 | 4/2015 |
| WO | 2015061209 | 4/2015 |
| WO | 2015075445 | 5/2015 |
| WO | 2015089344 | 6/2015 |
| WO | 2015132602 | 9/2015 |
| WO | 2015140212 | 9/2015 |
| WO | 2015179658 | 11/2015 |
| WO | 2015191715 | 12/2015 |
| WO | 2016020502 | 2/2016 |
| WO | 2016040723 | 3/2016 |
| WO | 2016040724 | 3/2016 |
| WO | 2016040868 | 3/2016 |
| WO | 2016058056 | 4/2016 |
| WO | 2016144873 | 9/2016 |
| WO | 2017059397 | 4/2017 |
| WO | 2017087826 | 5/2017 |
| WO | 2017201111 | 11/2017 |
| WO | 2017213494 | 12/2017 |
| WO | 2017223565 | 12/2017 |
| WO | 2018049083 | 3/2018 |
| WO | 2018058125 | 3/2018 |
| WO | 2018128664 | 7/2018 |
| WO | 2018083705 | 12/2018 |

OTHER PUBLICATIONS

Powell et al. (1998) "Compendium of Excipients for Parenteral Formulations" PDA J Pharm Sci Technol 52:238-311.

Price et al. (2014) "H6phospa-trastuzumab: bifunctional methylenephosphonate-based chelator with 89Zr, 111In and 177Lu" Dalton Trans. 43(1):119-131.

Reddy et al. (2000) "Elimination of Fc Receptor-Dependent Effector Functions of a Modified IgG4 Monoclonal Antibody to Human CD4" J. Immunol. 164:1925-1933.

Robbins et al. (2008) "Single and Dual Amino Acid Substitutions in TCR CDRs Can Enhance Antigen-Specific T Cell Functions", J. Immunol. 180(9):6116-6131.

Schumacher et al. (2016) "Current Status: Site-Specific Antibody Drug Conjugates" 36(Suppl 1):S100-7.

Shapiro et al. (1998) "Cutting Edge: Nuclear Factor of Activated T Cells and AP-1 Are Insufficient for IL-2 Promoter Activation: Requirement for CD28 Up-Regulation of RE/AP", J. Immunol. 161(12): 6455-6458.

Shield et al. (2002) "Lack of Fucose on Human IgG1 N-Linked Oligosaccharide Improves Binding to Human Fc RIII and Antibody-dependent Cellular Toxicity" Journal of Biological Cancer 277:26733-26740.

Slizys and Widnersson (2016) "The new "Pet" on the block: radio imaginig with Zirconium-89" FPA Patent Attorneys, 5 pages.

Tavare et al. (2014) "Engineered Antibody Fragments for Immuno-PET Imaging of Endogenous CD8+ T Cells in Vivo" Proceeding of the National Academy of Sciences of the USA 111(3):1108-1113.

Tavare et al. (2015) "Detection of Antibody Therapy-Induced Anti-Tumor Immune Responses Using Anti-CD8 Immuno-Pet", J. Immunother. Cancer, vol. 3, Suppl. 2, p. 391.

Tavare et al. (2015) Anti-CD8 ImmunoPET Detection of CD8 + Tumor Infiltrating Lymphcytes! http://www.imaginab.com/WMIC2014%20TIL%20Poster_Tavare%20(Uploaded).pdf.

Tavare et al. (2015) "Immuno-PET of Murine T Cell Reconstitution Postadoptive Stem Cell Transplantation Using Anti-CD4 and Anti-CD8 Cys-Diabodies", The Journal of Nuclear Medicine, 56(8):1258-1264.

Tavare et al. (2015) Supplementary Data p. S14; https://cancerres.aarcrjournals.org/content/canres/suppl/2016/02/04/0008-5472.CAN-15-1707.DC1/151683_2_supp_0_nwnncx.pdf.

Tavare et al. (2016) "An Effective Immuno-PET Imaging Method to Monitor CD8-Dependent Responses to Immunotherapy" Cancer Research 76(1):73-82.

Vajdos et al. (2002) "Comprehensive Functional Maps of the Antigenbinding Site of an Anti-ErbB2 Antibody Obtained withShotgun Scanning Mutagenesis" J. Mol. Biol. 320:415-428.

Van De Watering et al. (2014) "Zirconium-89 Labeled Antibodies: A New Tool for Molecular Imaging in Cancer Patients" Biomed Research international Article ID 203601:1-13.

(56) References Cited

OTHER PUBLICATIONS

Van Dongen et al. (2007) "Immuno-PET: A Navigator in Monoclonal Antibody Development and Applications" The Oncologist 12:1379-1389.
Vosjan et al. (2010) "Conjugation and Radiolabeling of Monoclonal Antibodies with Zirconium-89 for PET Imaging Using the Bifunctional Chelate p-Isothiocyanatobenzyl-desferrioxamine" Nature Protocols 5(4):739.
Vugts et al. (2016) "Comparison of the octadentate bifunctional chelator DFO-pPhe-NCS and the clinically used hexadentate bifunctional chelator DFO-pPhe-NCS for 89Zr-immuno-PET," Eur J Nucl Med Mol Imaging, 44(2):286-295.
Walsh et al. (1994) "Immune Function in Mice Lacking the Perforin Gene" Proc. Natl. Acad. Sci. USA 91(23):10854-58.
Wang et al. (2009) "Conserved Amino Acid Networks Involved in Antibody Variable Domain Interactions" Proteins 76(1):99-114.
Warram et al. (2014) "Antibody-based Imaging Strategies for Cancer", Cancer Metastasis, 33:809-822.
Wu et al. (1987) "Receptor-mediated in VitroGene Transformation by a Soluble DNA Carrier System" J. Biol. Chem. 262:4429-4432.
Zhai et al. (2015) "Novel Bifunctional Cyclic Chelator for (89)Zr Labeling-Radiolabeling and Targeting Properties of RGD Conjugates" Mol. Pharmaceutics 12(6):2142-2150.
Al-Lazikani et al. (1997) "Standard Conformations for the Canonical Structures of Immunoglobulins" J. Mol. Biol. 273:927-948.
Accession# NP_001759.3 alpha.
Accession # NP_004922.1 beta.
Altschul et al. (1990) "Basic Local Alignment Search Tool" J. Mol. Biol. 215:403-410.
Altschul et al. (1997) "Gapped BLAST and PSI-BLAST: a New Generation of Protein Database Search Programs" Nucleic Acids Res. 25:3389-402.
Alzimami et al. (2014) "Comparison of Zr-89, I-124, and F-18 Imaging Characteristics in PET Using Gate Monte Carlo Simulations: Imaging" International Journal of Radiation Oncology 88:502.
Anthony et al. (2012) "Dissecting the T Cell Response: Proliferation Assays vs. Cytokine Signatures by ELISPOT" Cells 1:127-140.
Boerman and Oyen (2011) "Immuno-PET of Cancer: A Revival of Antibody Imaging" Journal of Nuclear Medicine 52(8):1171-1172.
Boster (2014) "Anti-CD8 Alpha Antibody", https://www.bosterbio.com/datshete_new.php?sku=PB9249.
Cantrell et al. (2002) "T cell Antigen Receptor Signal Transduction" Immunology 105(4):369-374.
Chang et al. (2015) "Metabolic Competition in the Tumor Microenvironment Is a Driver of Cancer Progression" Cell 162:1229-1241.
Chatterjee et al. (2016) "A humanized antibody for imaging immune checkpoint ligand PD-L1 expression in tumors" Oncotarget 7(9):10215-10227.
Chen et al. (2013) "Molecular mechanisms of T cell co-stimulation and co-inhibition" Nature Rev. Immunol. 13:227-242.
De Vries (2015) "MPDL3280A-imaging-IST-UMCG", ClinicalTrials.gov Identifier: NCT02453984, University Medical Center Groningen, 10 pages.
De Vries "Antibody immunotherapy imaging." Department of Medical Oncology University Medical Center Groningen, The Netherlands, 16 pages.
Deng et al. (2016) "Preclinical pharmacokinetics, pharmacodynamics, tissue distribution, and tumor penetration of anti-PD-L1 monoclonal antibody, an immune checkpoint inhibitor" mAbs 8(3):593-603.
Denkberg et al. (2001) "Critical Role for CD8 in Binding of MHC Tetramers to TCR: CD8 Antibodies Block Specific Binding of Human Tumor—Specific MHC-Peptide Tetramers to TCR" The Journal of Immunology 167:270-276.
Deri et al. (2015) "p-SCN-Bn-HOPO: A Superior Bifunctional Chelator for (89)Zr ImmunoPET" Bioconjugate Chem. 26(12):2579-2591.

Dijkers et al. (2010) "Biodistribution of 89Zr-trastuzumab and PET Imaging of HER2-Positive Lesions in Patients With Metastatic Breast Cancer" Clinical Pharmacology and Therapeutics 87(5):586-592.
Flies et al. (2011) "Blockade of the B7-H1/PD-1 Pathway for Cancer Immunotherapy" Yale J. Biol. Med. 84:409-421.
Gebhart et al. (2015) "Molecular imaging as a tool to investigate heterogeneity of advanced HER2-positive breast cancer and to predict patient outcome under trastuzumab emtansine (T-DM1); the ZEPHIR trial" Annals of Oncology Advance Access, 22 pages.
Goldrath and Bevan (1999) "Selecting and maintaining a diverse T cell repertoire" Nature 402:255-262.
Gonnet et al. (1992) "Exhaustive Matching of the Entire Protein Sequence Database" Science 256: 1443-1445.
Herbst et al. (2014) "Predictive correlates of response to the anti-PD-L1 antibody MPDL3280A in cancer patients" Nature 515(7528):563-567.
Heskamp et al. (2015) "Noninvasive Imaging of Tumor PD-L1 Expression Using Radiolabeled Anti-PD-L1 Antibodies" Cancer Res. 75(14):2928-2936.
Higashikawa et al. (2014) "64Cu-DOTA-Anti-CTLA-4 mAb Enabled PET Visualization of CTLA-4 on the T-Cell Infiltrating Tumor Tissues" PLoS One 9(11):e109866, 8 pages.
International Search Report from PCT/US2018/043343 dated Oct. 23, 2018.
Jauw et al. (2016) "Immuno-PositronEmission-Rob'sographywithZirconium-89-Labeled Monoclonal Antibodies in Oncology: What Can We Learn from Initial Clinical Trials?" Frontiers in Pharmacology 7:131145.
Jing et al. (2015) "Combined immune checkpoint protein blockade and low dose whole body irradiation as immunotherapy for myeloma" J. for Immuno. Therapy of Cancer 3(2):1-15.
Josefsson et al. (2016) "Imaging Biodistribution, and Dosimetry of Radionuclide-Labeled PD-L1 Antibody in an Immunocompetent Mouse Model of Breast Cancer" Cancer Research 76(2):472-479.
Kabat (1991) "Sequences of Proteins of Immunological Interest," National Institutes of Health, Bethesda, Md.
Krishnaswamy et al. (2014) "Antibody-Derived In Vivo Imaging of Tau Pathology", The Journal of Neuroscience, 34(50):16835-16850.
Knight et al. (2016) "Scaling-down Antibody Radiolabeling Reactions With Zirconium-89", Dalton Trans., 45:6343-6347.
Lamberts et al. (2015) "ImmunoPET with Anti-Mesothelin Antibody in Patients with Pancreatic and Ovarian Cancer Before Anti-Mesothelin Antibody-Drug Conjugate Treatment" Clinical Cancer Research 22(7):1642-1652.
Langer (1990) "New Methods of Drug Delivery" Science 249:1527-1533.
Li and Zhu (2016) "Immuno-PET imagining using 89Zr labeled PD-L1 antibody in non-small cell lung cancer Xenograft" J. Nucl. Med., 57(S2):337.
Lloyd (1999) "The Art, Science and Technology of Pharmaceutical Compounding" International Journal of Pharmaceutical Compounding 8 pages.
Martin et al. (1989) "Modeling Antibody Hypervariable Loops: A Combined Algorithm" Proc Natl Acad Sci 86:9268-9272.
Matano et al. (1998) "Administration of an Anti-Cd8 Monoclonal Antibody Interferes with the Clearance of Chimeric Simian/Human Immunodeficiency Virus during Primary Infections of Rhesus Macaques" J. of Virology p. 164-169.
Maute et al. (2015) "Engineering high-affinity PD-1 variants for optimized immunotherapy and immuno-PET imaging" Proc. Natl. Acad. Sci. USA 112(47):E6506-E6514.
Mindt et al. (2014) "Octadetante bifuntional chelating agent for Zr-89 based Imagining probes" Technology Opportunity Ref. No. UZ-15/736, 1 page.
Moskophidis et al. (1987) "Mechanism of Recovery from Acute Virus Infection: Treatment of Lymphocytic Choriomeningitis Virus-Infected Mice with Monoclonal Antibodies Reveals that Lyt-2+ T Lymphocytes Mediate Clearance of Virus and Regulate the Antiviral Antibody Response" J. Virol. 61(6):1867-74.
Natarajan et al. (2015) "Novel Radiotracer for ImmunoPET Imaging of PD-1 Checkpoint Expression on Tumor Infiltrating Lymphocytes" Bioconjug Chem. 26(10):2062-2069.

(56) References Cited

OTHER PUBLICATIONS

Nijland et al. (2019) "Molecular Imaging Using Radiolabeled Atezolizumab to AssessAtezolizumab Biodistribution in Lymphoma Patients" University Medical Center Groningen, ClinicalTrials.gov Identifier: NCT03850028, 11 pages.
Oosting et al. (2015) "89Zr-Bevacizumab PET Visualizes Heterogeneous Tracer Accumulation in Tumor Lesions of Renal Cell Carcinoma Patients and Differential Effects of Antiangiogenic Treatment", The Journal of Nuclear Medicine 56(1):63-69.
Padlan et al. (1995) "Identification of specificity-dertermining residues in antibodies" FASEB J. 9:133-139.
Pandya et al. (2015) "Di-macrocyclic terephthalamide ligands as chelators for the PET radionuclide zirconium-89" Chem Commun (Camb) 51(12):2301-2303.
Pardoll (2012) "The blockade of immune checkpoints in cancer immunotherapy" Nature Reviews Cancer 12:252-264.
Pearson (1994) "Using the FASTA Program to Search Protein and DNA Sequence Databases" Methods Mol. Biol. 24: 307-331.
Perk et al. (2010) "p-Isothiocyanatobenzyl-desferrioxamine: a new bifunctional chelate for facile radiolabeling of monoclonal antibodies with zirconium-89 for immuno-PET imaging" Eur. J. Nucl. Med. Mol Imaging 37(2):250-259.

FIG. 6A
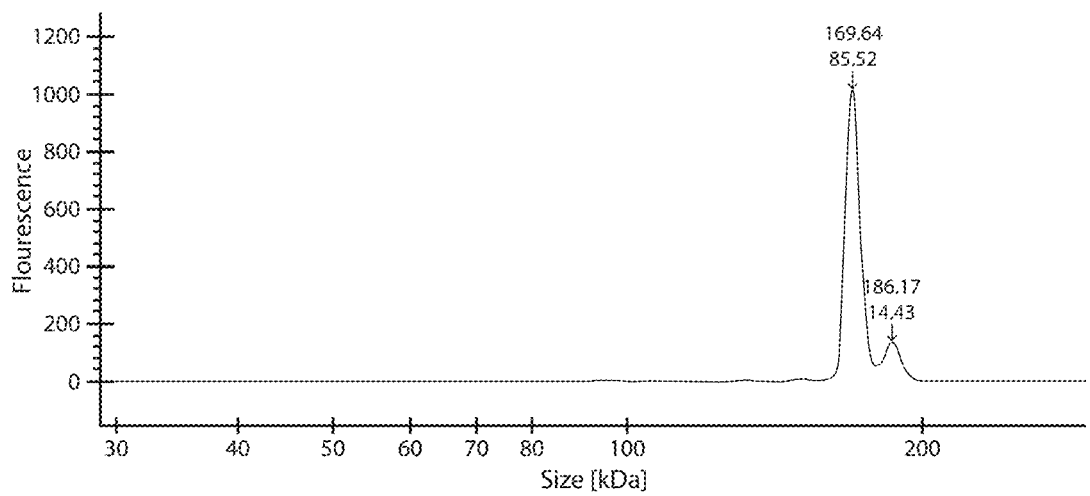
FIG. 6B
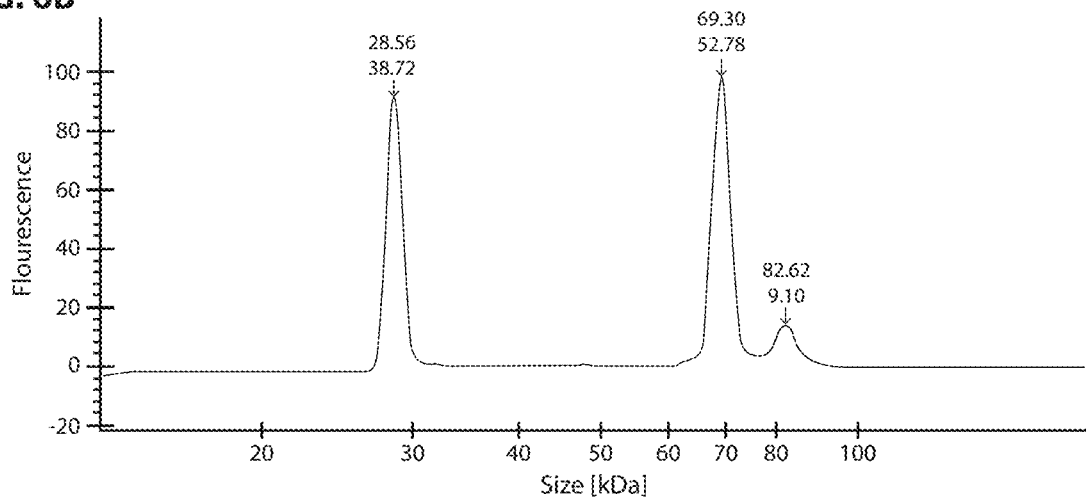
Figure 6

ANTI-CD8 ANTIBODIES AND USES THEREOF

CROSS-REFERENCE TO RELATED APPLICATIONS

This application is a continuation of U.S. patent application Ser. No. 16/914,112, filed Jun. 26, 2020, which is a continuation of U.S. patent application Ser. No. 16/043,048, filed Jul. 23, 2018, which claims the benefit under 35 U.S.C § 119(e) of U.S. Provisional Application Ser. No. 62/536,239, filed Jul. 24, 2017 and U.S. Provisional Application Ser. No. 62/660,902, filed Apr. 20, 2018; all of which are herein specifically incorporated by reference in their entirety.

FIELD

This disclosure relates to antibodies and antigen-binding fragments of antibodies that specifically bind to the glycoprotein CD8, therapeutic and diagnostic methods of using those antibodies, radiolabeled anti-CD8 antibodies, fluorescently labeled anti-CD8 antibodies, and their use in imaging.

SEQUENCE LISTING

An official copy of the sequence listing is submitted concurrently with the specification electronically via Patent Center. The contents of the electronic sequence listing (10357US03-US_Sequence_Listing.xml; Size: 24,961 bytes; and Date of Creation: Oct. 26, 2022) is herein incorporated by reference in its entirety.

BACKGROUND

T cell co-stimulatory and co-inhibitory molecules (collectively named co-signaling molecules) play a crucial role in regulating T cell activation, subset differentiation, effector function and survival (Chen et al 2013, Nature Rev. Immunol. 13: 227-242). Following recognition of cognate peptide-MHC complexes on antigen-presenting cells by the T cell receptor (TCR), co-signaling receptors co-localize with T cell receptors at the immune synapse, where they synergize with TCR signaling to promote or inhibit T cell activation and function (Flies et al 2011, Yale J. Biol. Med. 84: 409-421). The ultimate immune response is regulated by a balance between co-stimulatory and co-inhibitory signals ("immune checkpoints") (Pardoll 2012, Nature Reviews Cancer 12: 252-264). CD8, a cell surface glycoprotein, stabilizes T cell receptor-MHC-I interaction and initiates intracellular signaling via lymphocyte-specific protein tyrosine kinase (Lck) phosphorylation of CD3-associated immunoreceptor tyrosine-based activation motifs (ITAMs) for activation.

In humans, CD8 is predominantly expressed on cytotoxic T lymphocytes, but also expressed on subsets of dendritic cells, natural killer cells, natural killer T cells, and γδT cells. The glycoprotein consists of two isoforms, α and β, which are encoded by different genes and expressed as αα homodimers or αβ heterodimers. αβ heterodimers are more prevalent.

Immuno-positron emission tomography (PET) is a diagnostic imaging tool that utilizes monoclonal antibodies labeled with positron emitters, combining the targeting properties of an antibody with the sensitivity of positron emission tomography cameras. See, e.g., *The Oncologist*, 12: 1379 (2007); *Journal of Nuclear Medicine*, 52(8): 1171 (2011). Immuno-PET enables the visualization and quantification of antigen and antibody accumulation in vivo and, as such, can serve as an important tool for diagnostics and complementing therapy. For example, immuno-PET can aid in the selection of potential subject candidates for a particular therapy, as well as in the monitoring of treatment.

There is a need for diagnostic tools for predicting and monitoring the suitability or responsiveness of a subject to a particular anti-tumor therapy.

BRIEF SUMMARY

Provided herein are monoclonal antibodies and antigen-binding fragments thereof that bind CD8. The antibodies can be useful, inter alia, for targeting immune cells expressing CD8, and for modulating CD8 positive T cell activity. In certain embodiments, the antibodies are useful for inhibiting or neutralizing CD8 positive T cell activity, e.g. inhibiting IFNγ production in CD8 positive T cells and/or inhibiting transcription factor activator-protein (AP-1) in activated T cells. In some embodiments, the antibodies and antigen-binding fragments are useful for binding CD8 in vivo. The antibodies are useful in treating a disease or condition associated with CD8 positive T cell activation.

The antibodies provided herein can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

In a first aspect, provided herein are isolated recombinant monoclonal antibodies or antigen-binding fragments thereof that bind specifically to CD8. In certain embodiments, the antibodies are fully human.

Exemplary anti-CD8 antibodies are listed in Table 1, which provides the amino acid sequence identifiers and nucleic acid sequence identifiers of the heavy and light chain complementarity determining region sequences and heavy and light chain variable region sequences.

Also provided are antibodies, or antigen-binding fragments thereof, comprising an HCVR comprising an amino acid sequence of SEQ ID NO: 2, or a substantially similar sequence thereof having at least 90%, at least 95%, at least 98% or at least 99% sequence identity thereto.

Also provided are antibodies, or antigen-binding fragments thereof, comprising an LCVR comprising an amino acid sequence of SEQ ID NO: 10, or a substantially similar sequence thereof having at least 90%, at least 95%, at least 98% or at least 99% sequence identity thereto.

Also provided are antibodies, or antigen-binding fragments thereof, comprising a heavy chain CDR1 (HCDR1) comprising an amino acid sequence of SEQ ID NO: 4 or a substantially similar sequence thereof having at least 90%, at least 95%, at least 98% or at least 99% sequence identity.

Also provided are antibodies, or antigen-binding fragments thereof, comprising a heavy chain CDR2 (HCDR2) comprising an amino acid sequence of SEQ ID NO: 6 or a substantially similar sequence thereof having at least 90%, at least 95%, at least 98% or at least 99% sequence identity.

Also provided are antibodies, or antigen-binding fragments thereof, comprising a heavy chain CDR3 (HCDR3) comprising an amino acid sequence of SEQ ID NO: 8 or a substantially similar sequence thereof having at least 90%, at least 95%, at least 98% or at least 99% sequence identity.

Also provided are antibodies, or antigen-binding fragments thereof, comprising a light chain CDR1 (LCDR1) comprising an amino acid sequence of SEQ ID NO: 12 or a substantially similar sequence thereof having at least 90%, at least 95%, at least 98% or at least 99% sequence identity.

Also provided are antibodies, or antigen-binding fragments thereof, comprising a light chain CDR2 (LCDR2) comprising an amino acid sequence of SEQ ID NO: 14 or a substantially similar sequence thereof having at least 90%, at least 95%, at least 98% or at least 99% sequence identity.

Also provided are antibodies, or antigen-binding fragments thereof, comprising a light chain CDR3 (LCDR3) comprising an amino acid sequence of SEQ ID NO: 16 or a substantially similar sequence thereof having at least 90%, at least 95%, at least 98% or at least 99% sequence identity.

In some embodiments, the antibody or antigen-binding fragment thereof comprises an HCDR3/LCDR3 amino acid sequence pair comprising SEQ ID NOs: 8/16. In some embodiments, the antibody or antigen-binding fragment thereof comprises an HCVR/LCVR amino acid sequence pair of SEQ ID NOs: 2/10. In some embodiments, the antibody or antigen-binding fragment thereof comprises the CDR amino acid sequences within the HCVR/LCVR amino acid sequence pair of SEQ ID NOs: 2/10. In some embodiments, the antibody or antigen-binding fragment thereof comprises the six CDR amino acid sequence combination (HCDR1/HCDR2/HCDR3/LCDR1/LCDR2/LCDR3) of SEQ ID NOs: 4/6/8/12/14/16.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Provided herein are anti-CD8 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

Provided herein are antibodies and antigen-binding fragments thereof that bind specifically to CD8 from human or other species. In certain embodiments, the antibodies may bind to human CD8 and/or monkey CD8. In certain embodiments, the antibodies bind to human CD8a.

In a second aspect, nucleic acid molecules are provided herein that encode for anti-CD8 antibodies or portions thereof. For example, provided herein are nucleic acid molecules encoding the HCVR amino acid sequence of SEQ ID NO: 2; in certain embodiments the nucleic acid molecule comprises a polynucleotide sequence of SEQ ID NO: 1, or a substantially similar sequence thereof having at least 90%, at least 95%, at least 98% or at least 99% sequence identity thereto. Provided herein are nucleic acid molecules encoding the LCVR amino acid sequence of SEQ ID NO: 10; in certain embodiments the nucleic acid molecule comprises a polynucleotide sequence of SEQ ID NO: 9, or a substantially similar sequence thereof having at least 90%, at least 95%, at least 98% or at least 99% sequence identity thereto. Provided herein are nucleic acid molecules encoding any of the CDR amino acid sequences listed in Table 1; in certain embodiments, the nucleic acid molecule comprises a polynucleotide sequence selected from any of the CDR nucleic acid sequences listed in Table 1, or a substantially similar sequence thereof having at least 90%, at least 95%, at least 98% or at least 99% sequence identity thereto.

In a related aspect, provided herein are recombinant expression vectors capable of expressing a polypeptide comprising a heavy or light chain variable region of an anti-CD8 antibody. For example, provided herein are recombinant expression vectors comprising any of the nucleic acid molecules mentioned above, i.e., nucleic acid molecules encoding any of the HCVR, LCVR, and/or CDR sequences as set forth in Table 1. Also provided are recombinant expression vectors capable of expressing a polypeptide comprising a heavy or light chain of an anti-CD8 antibody. For example, recombinant expression vectors comprising any of the nucleic acid molecules mentioned above, i.e., nucleic acid molecules encoding any of the heavy chain or light chain sequences as set forth in Table 1, are contemplated herein. Also included within the scope of the present disclosure are host cells into which such vectors have been introduced, as well as methods of producing the antibodies or portions thereof by culturing the host cells under conditions permitting production of the antibodies or antibody fragments, and recovering the antibodies and antibody fragments so produced.

In a third aspect, provided herein is a pharmaceutical composition comprising a recombinant human antibody or fragment thereof which specifically binds CD8 and a pharmaceutically acceptable carrier. In a related aspect, the composition is a combination of an anti-CD8 antibody and a second therapeutic agent. In one embodiment, the second therapeutic agent is any agent that is advantageously combined with an anti-CD8 antibody. Exemplary agents that may be advantageously combined with an anti-CD8 antibody include, without limitation, other agents that bind and/or modulate activated T cell signaling (including other antibodies or antigen-binding fragments thereof, etc.) and/or agents which do not directly bind CD8 but nonetheless modulate immune cell activation. Additional combination therapies and co-formulations involving the anti-CD8 antibodies provided herein are provided elsewhere in this disclosure.

In a fourth aspect, methods are provided to modulate the immune response in a subject, the method comprising administering a therapeutically effective amount of an anti-CD8 antibody or antigen-binding fragment thereof to the subject in need thereof. In certain embodiments, the methods diminish immune response in a subject, e.g. decrease production of IFNγ in activated CD8 positive T cells and/or inhibit transcription factor activator-protein (AP-1) in activated T cells. The methods comprise administering to the subject an effective amount of an antibody or fragment thereof that binds CD8. In one embodiment, provided herein is a method to mitigate T cell activation in a subject comprising administering a therapeutically effective amount of an anti-CD8 antibody or antigen-binding fragment thereof to the subject in need thereof. In certain embodiments, the subject in need thereof may suffer from a disease or disorder such as infection or an autoimmune disease.

In a fifth aspect, provided herein are therapeutic methods for treating a disease or disorder such as an infection or an autoimmune disease in a subject using an anti-CD8 antibody or antigen-binding portion of an antibody provided herein, wherein the therapeutic methods comprise administering a therapeutically effective amount of a pharmaceutical composition comprising an antibody or fragment of an antibody provided herein to the subject in need thereof. The disorder treated is any disease or condition which is improved, ameliorated, inhibited or prevented by inhibition of CD8 positive T cell activity or signaling. In certain embodiments, the antibody or antigen-binding fragment thereof is administered in combination with a second therapeutic agent to the subject in need thereof. The second therapeutic agent may be selected from the group consisting of an antibody to another T cell co-inhibitor, an antibody to a tumor cell antigen, an antibody to a T cell receptor, an antibody to an epitope on a virally infected cell, a cytotoxic agent, an anti-cancer drug, an anti-viral drug, an anti-inflammatory drug (e.g., corticosteroids), chemotherapeutic agent, radiation therapy, an immunosuppressant and any other drug or therapy known in the art. In certain embodiments, the second therapeutic agent may be an agent that helps to counteract or reduce any possible side effect(s) associated with an antibody or antigen-binding fragment thereof provided herein, if such side effect(s) should occur.

The antibody or fragment thereof may be administered subcutaneously, intravenously, intradermally, intraperitoneally, orally, intramuscularly, or intracranially. The antibody or fragment thereof may be administered at a dose of about 0.1 mg/kg of body weight to about 100 mg/kg of body weight of the subject.

Also provided herein is the use of an anti-CD8 antibody or antigen-binding fragment thereof in the manufacture of a medicament for the treatment of a disease or disorder that would benefit from the blockade of CD8 binding and/or signaling, or from the mitigation of CD8 positive T cell activation.

In another aspect, provided herein are radiolabeled anti-CD8 antibody conjugates for use in immuno-PET imaging. The conjugate comprises an anti-CD8 antibody or antigen-binding fragment thereof, a chelating moiety, and a positron emitter.

Provided herein are processes for synthesizing said conjugates and synthetic intermediates useful for the same.

Provided herein are methods of imaging a tissue that expresses CD8, the methods comprising administering a radiolabeled anti-CD8 antibody conjugate described herein to the tissue; and visualizing the CD8 expression by positron emission tomography (PET) imaging.

Provided herein are methods of imaging a tissue comprising CD8-expressing cells, for example, CD8-expressing intratumoral lymphocytes, or CD8 positive T cells, the methods comprising administering a radiolabeled anti-CD8 antibody conjugate described herein to the tissue, and visualizing the CD8 expression by PET imaging.

Provided herein are methods for detecting CD8 in a tissue, the methods comprising administering a radiolabeled anti-CD8 antibody conjugate described herein to the tissue; and visualizing the CD8 expression by PET imaging. In one embodiment, the tissue is present in a human subject. In certain embodiments, the subject is a non-human mammal. In certain embodiments, the subject has a disease or disorder such as cancer, an inflammatory disease, or an infection.

Provided herein are methods for detecting CD8 in a tissue, the methods comprising contacting the tissue with an anti-CD8 antibody conjugated to a fluorescent molecule described herein; and visualizing the CD8 expression by fluorescence imaging.

Provided herein are methods for identifying a subject to be suitable for anti-tumor therapy, the methods comprising selecting a subject with a solid tumor, administering a radiolabeled anti-CD8 antibody conjugate described herein, and visualizing the administered radiolabeled antibody conjugate in the tumor by PET imaging wherein presence of the radiolabeled antibody conjugate in the tumor identifies the subject as suitable for anti-tumor therapy.

Provided herein are methods of treating a tumor, the methods comprising selecting a subject with a solid tumor; determining that the solid tumor is CD8 positive; and administering an anti-tumor therapy to the subject in need thereof. In certain embodiments, the anti-tumor therapy comprises an inhibitor of the PD-1/PD-L1 signaling axis (e.g., an anti-PD-1 antibody or an anti-PD-L1 antibody), an example of a checkpoint inhibitor therapy. In certain embodiments, the subject is administered a radiolabeled anti-CD8 antibody conjugate described herein, and localization of the radiolabeled antibody conjugate is imaged via positron emission tomography (PET) imaging to determine if the tumor is CD8 positive. In certain embodiments, the subject is further administered a radiolabeled anti-PD-1 antibody conjugate, and localization of the radiolabeled antibody conjugate is imaged via positron emission tomography (PET) imaging to determine if the tumor is PD-1-positive.

Provided herein are methods for monitoring the efficacy of an anti-tumor therapy in a subject, wherein the methods comprise selecting a subject with a solid tumor wherein the subject is being treated with an anti-tumor therapy; administering a radiolabeled anti-CD8 conjugate described herein to the subject; imaging the localization of the administered radiolabeled conjugate in the tumor by PET imaging; and determining tumor growth, wherein a decrease from the baseline in uptake of the conjugate or radiolabeled signal indicates efficacy of the anti-tumor therapy. In certain embodiments, the anti-tumor therapy comprises a PD-1 inhibitor (e.g., REGN2810, BGB-A317, nivolumab, pidilizumab, and pembrolizumab), a PD-L1 inhibitor (e.g., atezolizumab, avelumab, durvalumab, MDX-1105, and REGN3504, as well as those disclosed in Patent Publication No. US 2015-0203580), CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to LAG3, CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen-binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3xCD20 bispecific antibody, or PSMAxCD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, and an antibody-drug conjugate (ADC) (e.g., anti-CD19-DM4 ADC, and anti-DS6-DM4 ADC).

Provided herein are methods for predicting response of a subject to an anti-tumor therapy, the methods comprising selecting a subject with a solid tumor; and determining if the tumor is CD8 positive, wherein if the tumor is CD8 positive it predicts a positive response of the subject to an anti-tumor therapy. In certain embodiments, the tumor is determined positive by administering a radiolabeled anti-CD8 antibody conjugate of the present disclosure and localizing the radiolabeled antibody conjugate in the tumor by PET imaging wherein presence of the radiolabeled antibody conjugate in the tumor indicates that the tumor is CD8 positive. In some embodiments, the anti-tumor therapy is selected from a PD-1 inhibitor (e.g., REGN2810, BGB-A317, nivolumab, pidilizumab, and pembrolizumab), a PD-L1 inhibitor (e.g., atezolizumab, avelumab, durvalumab, MDX-1105, and REGN3504), CTLA-4 inhibitor (e.g., ipilimumab), a TIM3 inhibitor, a BTLA inhibitor, a TIGIT inhibitor, a CD47 inhibitor, a GITR inhibitor, a LAG3 inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen-binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3xCD20 bispecific antibody, or PSMAxCD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, and an antibody-drug conjugate (ADC) (e.g., anti-CD19-DM4 ADC, and anti-DS6-DM4 ADC).

Provided herein are methods for predicting a positive response to an anti-tumor therapy in a subject with a solid tumor. The methods comprise administering a radiolabeled anti-CD8 antibody conjugate to the subject to determine the presence of CD8 positive cells in the solid tumor; wherein the presence of CD8 positive cells predicts a positive response to an anti-tumor therapy.

Provided herein are methods for monitoring a positive response to an anti-tumor therapy in a subject with a solid tumor. The methods comprise (a) administering one or more doses of an anti-tumor therapy to the subject; and (b) administering a radiolabeled anti-CD8 antibody conjugate to the subject 1 to 20 weeks after administration of the anti-tumor therapy to determine the presence of CD8 positive cells in the solid tumor. The presence of CD8 positive cells indicates a positive response to the anti-tumor therapy.

Provided herein are methods for predicting or monitoring success or efficacy of anti-tumor therapy in a subject with a solid tumor, the method comprising: (a) determining the level of CD8 positive cells in the tumor; and (b) correlating the level of CD8 positive cells with successful anti-tumor therapy. An elevated level of CD8 above a certain threshold is predictive or indicative of successful anti-tumor therapy.

Provided herein are methods for monitoring T-cell presence or T-cell infiltration in a tumor over time, the method comprising: (a) administering a radiolabeled anti-CD8 antibody conjugate at a first timepoint to a subject having the tumor and determining the presence of CD8 positive T-cells in the tumor; (b) administering one or more doses of an anti-tumor therapy to the subject; and (c) administering a radiolabeled anti-CD8 antibody conjugate at a second timepoint to the subject 1 to 20 weeks after administration of the anti-tumor therapy and determining the presence of CD8 positive T-cells in the tumor. The presence of T-cells in the tumor is indicative of a positive response to the anti-tumor therapy.

BRIEF DESCRIPTION OF THE FIGURES

FIG. 6 depicts electropherograms of DFO-mAb1 conjugate. FIG. 6A) represents non-reduced conjugate and FIG. 6B) represents reduced conjugate.

DETAILED DESCRIPTION

I. Definitions

Figure 1:
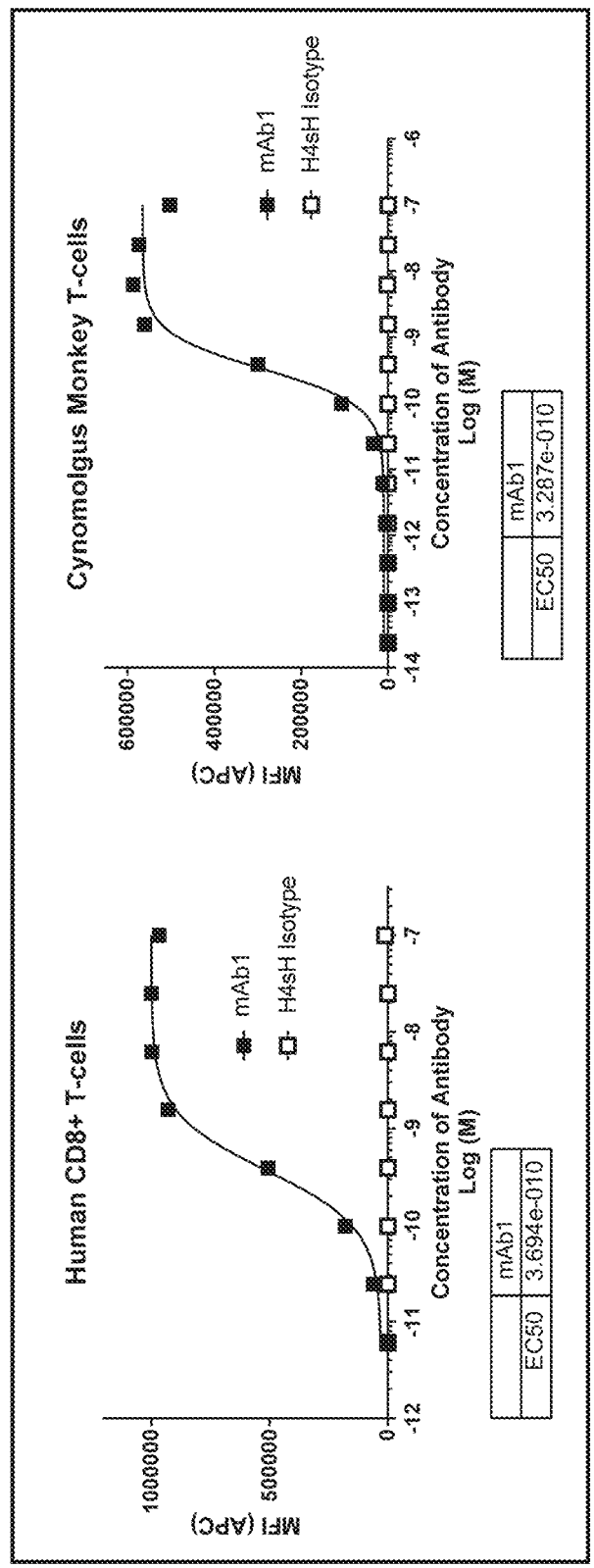
FIG. 1 depicts mAb1 binding to human CD8+ and cynomolgus monkey T-cells.

Unless defined otherwise herein, all technical and scientific terms used herein have the same meaning as commonly understood by one of ordinary skill in the art to which the disclosed subject matter belongs.

The term "CD8" (Cluster of Differentiation 8) refers to a cell surface glycoprotein predominantly expressed on cytotoxic T lymphocytes, but also expressed on subsets of dendritic cells, natural killer cells, natural killer T cells, and γδT cells. The glycoprotein consists of two isoforms, α and β, which are encoded by different genes, and expressed as aa homodimers or as heterodimers, the latter of which is dominant. The CD8 coreceptors stabilize T cell receptor MHC-1 interaction and initiate intracellular signaling via lymphocyte-specific protein tyrosine kinase (Lck) phosphorylation of CD3-associated immunoreceptor tyrosine-based activation motifs (ITAMs) for activation.

The amino acid sequence of full-length CD8α is provided in UniProt as accession number P01732 and is also referred to herein as SEQ ID NO: 18. The amino acid sequence of full-length CD8β is provided in UniProt as accession number 10966 and is also referred to herein as SEQ ID NO: 20. The term "CD8" includes full length CD8α or CD8β, recombinant CD8, fragments thereof, and fusions thereof. The term also encompasses CD8α or CD8β, or a fragment thereof, coupled to, for example, histidine tag, mouse or human Fc, or a signal sequence such as the signal sequence of ROR1. For example, the term includes sequences exemplified by SEQ ID NO: 18 or 20, comprising a mouse Fc (mIgG2a) at the C-terminal, coupled to a fragment of CD8α or CD8β. Other protein variants comprise a histidine tag at the C-terminal coupled to CD8 or a fragment thereof. Unless specified as being from a non-human species, the term "CD8" means human CD8.

CD8 is a member of the immunoglobulin (Ig) superfamily with an immunoglobulin variable (IgV)-like extracellular domain connected to the membrane by a think stalk, and an intracellular tail.

As used herein, the term "T cell co-inhibitor" refers to a ligand and/or receptor which modulates the immune response via T cell activation or suppression. The term "T cell co-inhibitor", also known as T cell co-signaling molecule, includes, but is not limited to, lymphocyte activation gene 3 protein (LAG-3, also known as CD223), programmed death-1 (PD-1), cytotoxic T-lymphocyte antigen-4 (CTLA-4), B and T lymphocyte attenuator (BTLA), CD-28, 2B4, LY108, T cell immunoglobulin and mucin-3 (TIM3), T cell immunoreceptor with immunoglobulin and ITIM domains (TIGIT; also known as VSIG9), leucocyte associated immunoglobulin-like receptor 1 (LAIR1; also known as CD305), inducible T cell costimulator (ICOS; also known as CD278), B7-1 (CD80), and CD160.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments, the FRs of the antibody (or antigen-binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-CD8 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes fully human anti-CD8 monoclonal antibodies comprising variants of any of the HCVR, LCVR, and/or CDR amino acid sequences disclosed herein having one or more conservative substitutions. For example, the present disclosure includes anti-CD8 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include non-naturally occurring human antibodies. The term includes antibodies that are recombinantly produced in a non-human mammal, or in cells of a non-human mammal. The term is not intended to include antibodies isolated from or generated in a human subject.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $5 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to CD8.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to CD8.

An "isolated antibody", as used herein, is intended to refer to an antibody that is substantially free of other antibodies (Abs) having different antigenic specificities (e.g., an isolated antibody that specifically binds CD8, or a fragment thereof, is substantially free of Abs that specifically bind antigens other than CD8.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art.

See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix. Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, in need of amelioration, prevention and/or treatment of a disease or disorder such as chronic infection, cancer or autoimmune disease.

II. General Description

CD8 is expressed on cytotoxic T cells, which are generated in the thymus and express the T cell receptor. CD8 is expressed as a dimeric co-receptor, typically comprising one CD8α protein and one CD8β protein. CD8+ T cells recognize peptides presented by MHC I, and the CD8 heterodimer binds to MHC I α3 during antigen presentation. Activated CD8+ T cells are involved in eliminating infected or malignant cells, and are also implicated in autoimmune disease.

Fully human anti-CD8 antibodies described herein demonstrate specific binding to CD8α and/or CD8β. Such antibodies can be used to treat chronic infection, cancer, or autoimmune disease.

In certain embodiments, the antibodies provided herein are obtained from mice immunized with a primary immunogen, such as human CD8α protein and/or human CD8β protein, which may be purchased commercially, or may be produced recombinantly. The full-length amino acid sequences of human CD8α and human CD8β are shown as SEQ ID NOs: 18 and 20, respectively. In certain embodiments, the antibodies provided herein are obtained from mice immunized with a primary immunogen, such as human CD8α DNA and/or human CD8β DNA. The full-length nucleic acid sequence for human CD8α may be found in SEQ ID NO: 17. The full-length human CD8β nucleic acid sequence may be found in SEQ ID NO: 19.

The immunogen may be a biologically active and/or immunogenic fragment of recombinantly produced CD8, a fusion protein, DNA encoding the active fragment thereof, or DNA encoding the entire CD8α protein or CD8β protein. The fragment may be derived from either the N-terminal or C-terminal of human CD8α and human CD8β, or from any site within the human CD8α and human CD8β amino acid sequences.

Preparation of Human Antibodies

Methods for generating human antibodies in transgenic mice are known in the art. Any such known methods can be used in the context of the present disclosure to make human antibodies that specifically bind to CD8.

Using VELOCIMMUNE™ technology (see, for example, U.S. Pat. No. 6,596,541, Regeneron Pharmaceuticals, VELOCIMMUNE®) or any other known method for generating monoclonal antibodies, high affinity chimeric antibodies to CD8 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody provided herein, for example wild-type or modified IgG1 or IgG4. While the constant region selected may vary according to specific use, high affinity antigen-binding and target specificity characteristics reside in the variable region.

In general, the antibodies provided herein possess very high affinities, typically possessing $K_D$ of from about $10^{-12}$ through about $10^{-8}$ M, when measured by binding to antigen either immobilized on solid phase or in solution phase. The mouse constant regions are replaced with desired human constant regions to generate the fully human antibodies. While the constant region selected may vary according to specific use, high affinity antigen-binding and target specificity characteristics reside in the variable region.

Bioequivalents

The anti-CD8 antibodies and antibody fragments provided herein encompass proteins having amino acid sequences that vary from those of the described antibodies, but that retain the ability to bind CD8. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences provided herein encompass sequences that comprise one or more additions, deletions, or substitutions of nucleotides when compared to the disclosed sequence, but that encode an antibody or antibody fragment that is essentially bioequivalent to an antibody or antibody fragment disclosed herein.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single doses or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a subject can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies provided herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Therapeutic Administration and Formulations

Provided herein are therapeutic compositions comprising the anti-CD8 antibodies or antigen-binding fragments thereof of the present disclosure. The administration of therapeutic compositions in accordance with the present disclosure will be administered via a suitable route including, but not limited to, intravenously, subcutaneously, intramuscularly, intranasally, with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like.

Various delivery systems are known and can be used to administer the pharmaceutical compositions provided herein, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see, for example, Langer, 1990, Science 249: 1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present disclosure include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.) and the HUMIRA™ Pen (Abbott Labs, Abbott Park, IL), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

III. Radiolabeled Immunoconjugates of CD8 Antibodies for Immuno-PET Imaging

Provided herein are radiolabeled antigen-binding proteins that bind CD8. In some embodiments, the radiolabeled antigen-binding proteins comprise an antigen-binding protein covalently linked to a positron emitter. In some embodiments, the radiolabeled antigen-binding proteins comprise an antigen-binding protein covalently linked to one or more chelating moieties, which are chemical moieties that are capable of chelating a positron emitter.

Suitable radiolabeled antigen-binding proteins, e.g., radiolabeled antibodies, include those that do not impair, or do not substantially impair T-cell function upon exposure to the radiolabed antigen-binding protein. In some embodiments, a radiolabeled antigen-binding protein that binds CD8 is a weak blocker of CD8 T-cell function, i.e. T-cell function is unimpaired, or substantially unimpaired, upon exposure to the radiolabeled antibody. Use of a radiolabeled anti-CD8 binding protein having minimal impact on CD8 mediated T-cell function according to methods provided herein ensures a subject treated with the molecule is not disadvantaged by the inability of its T-cells to clear infection.

In some embodiments, antigen-binding proteins that bind CD8, e.g., antibodies, are provided, wherein said antigen-binding proteins that bind CD8 are covalently bonded to one or more moieties having the following structure:

$$-L-M_z$$

wherein L is a chelating moiety; M is a positron emitter; and z, independently at each occurrence, is 0 or 1; and wherein at least one of z is 1.

In some embodiments, the radiolabeled antigen-binding protein is a compound of Formula (I):

$$M-L-A-[L-M_z]_k \qquad (I)$$

A is a protein that binds CD8; L is a chelating moiety; M is a positron emitter; z is 0 or 1; and k is an integer from 0-30. In some embodiments, k is 1. In some embodiments, k is 2.

In certain embodiments, the radiolabeled antigen-binding protein is a compound of Formula (II):

$$A-[L-M]_k \qquad (II)$$

wherein A is a protein that binds CD8; L is a chelating moiety; M is a positron emitter; and k is an integer from 1-30.

In some embodiments, provided herein are compositions comprising a conjugate having the following structure:

$$A-L_k$$

wherein A is a protein that binds CD8; L is a chelating moiety; and k is an integer from 1-30; wherein the conjugate is chelated with a positron emitter in an amount sufficient to provide a specific activity suitable for clinical PET imaging.

Suitable binding proteins, chelating moieties, and positron emitters are provided below.

A. CD8 Binding Proteins

Suitable CD8 binding proteins specifically bind to CD8, and include those described in WO 2014/164553, incorporated herein by reference in its entirety. An exemplary anti-CD8 binding protein provided herein is the monoclonal antibody referred to hereinafter as mAb1 comprising the nucleic acid and amino acid sequence characteristics as set forth in Table 1.

TABLE 1

Nucleic Acid and Amino Acid Sequence Identifiers

| mAb1 | SEQ ID NOs | | | | | | | |
|---|---|---|---|---|---|---|---|---|
|  | HCVR | HCDR1 | HCDR2 | HCDR3 | LCVR | LCDR1 | LCDR2 | LCDR3 |
| Nucleic Acid Sequence Identifiers | 1 | 3 | 5 | 7 | 9 | 11 | 13 | 15 |
| Amino Acid Sequence Identifiers | 2 | 4 | 6 | 8 | 10 | 12 | 14 | 16 |

Table 1 sets forth the nucleic acid sequence identifiers and the amino acid sequence identifiers of the heavy chain variable region (HCVR), light chain variable region (LCVR), heavy chain complementarity determining regions (HCDR1, HCDR2 and HCDR3), and light chain complementarity determining regions (LCDR1, LCDR2 and LCDR3) of the exemplary anti-CD8 antibodies.

In some embodiments, the binding protein is an antibody or antigen-binding fragment comprising an HCVR comprising an amino acid sequence of SEQ ID NO: 2, or a substantially similar sequence thereof having at least 90%, at least 95%, at least 98% or at least 99% sequence identity thereto.

In some embodiments, the binding protein is an antibody or antigen-binding fragment comprising an LCVR comprising an amino acid sequence of SEQ ID NO: 10, or a substantially similar sequence thereof having at least 90%, at least 95%, at least 98% or at least 99% sequence identity thereto.

In some embodiments, the binding protein is an antibody or antigen-binding fragment comprising an HCVR and an LCVR amino acid sequence pair (HCVR/LCVR) of SEQ ID NOs: 2/10, e.g. mAb1.

In some embodiments, the binding protein is an antibody or antigen-binding fragment comprising a heavy chain CDR1 (HCDR1) amino acid sequence of SEQ ID NO: 4, or a substantially similar sequence thereof having at least 90%, at least 95%, at least 98% or at least 99% sequence identity.

In some embodiments, the binding protein is an antibody or antigen-binding fragment comprising a heavy chain CDR2 (HCDR2) amino acid sequence of SEQ ID NO: 6, or a substantially similar sequence thereof having at least 90%, at least 95%, at least 98% or at least 99% sequence identity.

In some embodiments, the binding protein is an antibody or antigen-binding fragment comprising a heavy chain CDR3 (HCDR3) amino acid sequence of SEQ ID NO: 8, or a substantially similar sequence thereof having at least 90%, at least 95%, at least 98% or at least 99% sequence identity.

In some embodiments, the binding protein is an antibody or antigen-binding fragment comprising a light chain CDR1 (LCDR1) amino acid sequence of SEQ ID NO: 12, or a substantially similar sequence thereof having at least 90%, at least 95%, at least 98% or at least 99% sequence identity.

In some embodiments, the binding protein is an antibody or antigen-binding fragment comprising a light chain CDR2 (LCDR2) amino acid sequence of SEQ ID NO: 14, or a substantially similar sequence thereof having at least 90%, at least 95%, at least 98% or at least 99% sequence identity.

In some embodiments, the binding protein is an antibody or antigen-binding fragment comprising a light chain CDR3 (LCDR3) amino acid sequence of SEQ ID NO: 16, or a substantially similar sequence thereof having at least 90%, at least 95%, at least 98% or at least 99% sequence identity.

In some embodiments, the binding protein is an antibody or antigen-binding fragment comprising an HCDR3 and an LCDR3 amino acid sequence pair (HCDR3/LCDR3) comprising of SEQ ID NOs: 8/16.

In some embodiments, the binding protein is an antibody or antigen-binding fragment comprising a set of six CDRs (i.e., HCDR1-HCDR2-HCDR3-LCDR1-LCDR2-LCDR3) contained within the exemplary anti-CD8 antibody provided in Table 1. In certain embodiments, the HCDR1-HCDR2-HCDR3-LCDR1-LCDR2-LCDR3 amino acid sequence combination comprises SEQ ID NOs: 4-6-8-12-14-16.

In some embodiments, the binding protein is an antibody or antigen-binding fragment comprising a set of six CDRs (i.e., HCDR1-HCDR2-HCDR3-LCDR1-LCDR2-LCDR3) contained within an HCVR/LCVR amino acid sequence pair of SEQ ID NOs: 2/10. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In some embodiments, binding proteins are antibodies and antigen-binding fragments thereof that compete for specific binding to CD8 with an antibody or antigen-binding fragment thereof comprising the CDRs of a HCVR and the CDRs of a LCVR, wherein the HCVR and LCVR amino acid sequence pair comprises SEQ ID NOs: 2/10.

Also provided herein are isolated antibodies and antigen-binding fragments thereof that bind CD8 and inhibit IFNγ production in activated CD8 positive T cells. In certain embodiments, the antibodies of the disclosure that bind CD8 and inhibit IFNγ production in activated CD8 positive T cells comprise the CDRs of an HCVR having an amino acid sequence of SEQ ID NO: 2; and the CDRs of a LCVR having an amino acid sequence of SEQ ID NO: 10.

Also provided herein are isolated antibodies and antigen-binding fragments thereof that bind CD8 and inhibit transcription factor activator-protein (AP-1) in activated T cells. In certain embodiments, the antibodies of the disclosure that bind CD8 and inhibit AP-1 in activated T cells comprise the CDRs of an HCVR having an amino acid sequence of SEQ ID NO: 2; and the CDRs of a LCVR having an amino acid sequence of SEQ ID NO: 10.

In some embodiments, the binding proteins are antibodies and antigen-binding fragments thereof that bind specifically to CD8 from human or other species. In certain embodiments, the antibodies may bind to human CD8 and/or to cynomolgus CD8.

In some embodiments, the binding proteins are antibodies and antigen-binding fragments thereof that cross-compete for binding to CD8 with a reference antibody or antigen-binding fragment thereof comprising the CDRs of a HCVR and the CDRs of a LCVR, wherein the HCVR and LCVR each has an amino acid sequence pair of SEQ ID NOs: 2/10.

In one embodiment, the binding protein is an isolated antibody or antigen-binding fragment that has one or more of the following characteristics: (a) is a fully human monoclonal antibody; (b) binds to CD8 with a $K_D$ equal to or less than $3.5 \times 10^{-8}$ M as measured by surface plasmon resonance; (c) binds to human CD8a; (d) inhibits IFNγ production in activated CD8 T cells; (e) inhibits transcription factor activator-protein (AP-1) in activated T cells; (f) cross-reacts with human and monkey CD8; (g) comprises the three heavy chain CDRs (HCDR1, HCDR2, and HCDR3) contained within the heavy chain variable region (HCVR) amino acid sequence of SEQ ID NO: 2; and (h) comprises the three light chain CDRs (LCDR1, LCDR2, and LCDR3) contained within the light chain variable region (LCVR) amino acid sequence of SEQ ID NO: 10.

In some embodiments, the antibody or antigen-binding fragment thereof may bind specifically to CD8 in an agonist manner, i.e., it may enhance or stimulate CD8 binding and/or activity; in other embodiments, the antibody may bind specifically to CD8 in an antagonist manner, i.e., it may block CD8 from binding to a natural CD8 binding partner.

In some embodiments, the antibody or antigen-binding fragment thereof may bind specifically to CD8 in an neutral manner, i.e., it binds but does not block or enhance or stimulate CD8 binding and/or activity.

In some embodiments, the antibodies and antigen-binding fragments thereof bind CD8, for example, CD8α or CD8β, with a dissociative half-life (t½) of greater than about 2.0 minutes as measured by surface plasmon resonance at 25° C. or 37° C., e.g., using an assay format as defined in Example 2, or a substantially similar assay. In certain embodiments, the antibodies or antigen-binding fragments bind CD8 with a t½ of greater than about 5 minutes, greater than about 10 minutes, greater than about 30 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, or greater than about 1100 minutes, as measured by surface plasmon resonance at 25° C. or 37° C., e.g., using an assay format as defined in Example 2 (e.g., mAb-capture or antigen-capture format), or a substantially similar assay.

In some embodiments, antibodies or antigen-binding fragments thereof bind to a human CD8-expressing cell with an $EC_{50}$ less than about 1 nM as measured by a flow cytometry assay as defined in Example 6, or a substantially similar assay. In certain embodiments, the antibodies or antigen-binding fragments thereof bind to a hCD8-expressing cell with an $EC_{50}$ less than about 0.9 nM, less than about 0.8 nM, less than about 0.7 nM, less than about 0.6 nM, less than about 0.5 nM, or less than about 0.4 nm, as measured by a flow cytometry assay, e.g., using the assay format in Example 6, or a substantially similar assay.

In some embodiments, antibodies or antigen-binding fragments thereof bind to a cynomolgus monkey CD8-expressing cell with an $EC_{50}$ less than about 1 nM as measured by a flow cytometry assay as defined in Example 6, or a substantially similar assay. In certain embodiments, the antibodies or antigen-binding fragments thereof bind to a monkey CD8-expressing cell with an $EC_{50}$ less than about 0.9 nM, less than about 0.8 nM, less than about 0.7 nM, less than about 0.6 nM, less than about 0.5 nM, or less than about 0.4 nm, as measured by a flow cytometry assay, e.g., using the assay format in Example 6, or a substantially similar assay.

In some embodiments, the antibodies or antigen-binding fragments thereof mitigate or block CD8 positive T cell activation with an $EC_{50}$ less than 1.2E-09 M as measured by a T cell/APC luciferase reporter assay as defined in Example 8, or a substantially similar assay. In certain embodiments, the antibodies or antigen-binding fragments thereof block CD8 positive T cell activation with an $EC_{50}$ by at least about 85%, or about 89%, as measured by a T cell/APC luciferase reporter assay, e.g., using the assay format as defined in Example 8, or a substantially similar assay.

In one embodiment, the antibody or fragment thereof is a fully human monoclonal antibody or antigen-binding fragment thereof that binds to CD8, wherein the antibody or fragment thereof exhibits one or more of the following characteristics: (i) comprises a HCVR amino acid sequence of SEQ ID NO: 2, or a substantially similar sequence thereof having at least 90%, at least 95%, at least 98% or at least 99% sequence identity; (ii) comprises a LCVR amino acid sequence selected of SEQ ID NO: 10, or a substantially similar sequence thereof having at least 90%, at least 95%, at least 98% or at least 99% sequence identity; (iii) comprises a HCDR3/LCDR3 amino acid sequence pair of SEQ ID NOs: 8/16, or a substantially similar sequence thereof having at least 90%, at least 95%, at least 98% or at least 99% sequence identity; (iv) comprises a HCDR1/LCDR1 amino acid sequence pair of SEQ ID NOs: 4/12, or a substantially similar sequence thereof having at least 90%, at least 95%, at least 98% or at least 99% sequence identity; a HCDR2/LCDR2 amino acid sequence pair of SEQ ID NOs: 6/14, or a substantially similar sequence thereof having at least 90%, at least 95%, at least 98% or at least 99% sequence identity; a HCDR3/LCDR3 amino acid sequence pair of SEQ ID NOs: 8/16, or a substantially similar sequence thereof having at least 90%, at least 95%, at least 98% or at least 99% sequence identity; (v) binds human CD8 with a binding dissociation equilibrium constant ($K_D$) of less than about $3.5 \times 10^{-8}$ M as measured in a surface plasmon resonance assay (vi) inhibits IFNγ production in activated CD8 positive T cells; and (vii) inhibits transcription factor activator-protein (AP-1) in activated T cells.

In certain embodiments, the antibodies may function by blocking or inhibiting the MHC class I-binding activity associated with CD8α by binding to any region or fragment of the full length protein, the amino acid sequence of which is shown in SEQ ID NO: 18. In certain embodiments, the antibodies may function by blocking or inhibiting the MHC class I-binding activity associated with CD8β by binding to any region or fragment of the full length protein, the amino acid sequence of which is shown in SEQ ID NO: 20.

In certain embodiments, the anti-CD8 antibodies or antigen-binding fragments thereof bind an epitope within any one or more of the regions exemplified in CD8α, either in natural form, as exemplified in SEQ ID NO: 18, or recombinantly produced, or to a fragment thereof. In some embodiments, the antibodies bind to an extracellular region comprising one or more amino acids selected from the group consisting of amino acid residues 22 to 182 of CD8α. In certain embodiments, the anti-CD8 antibodies or antigen-binding fragments thereof bind an epitope within any one or more of the regions exemplified in CD8β, either in natural form, as exemplified in SEQ ID NO: 20, or recombinantly produced, or to a fragment thereof. In some embodiments, the antibodies bind to an extracellular region comprising one or more amino acids selected from the group consisting of amino acid residues 22 to 170 of CD8β.

In certain embodiments, anti-CD8 antibodies and antigen-binding fragments thereof interact with one or more epitopes found within the extracellular region of CD8α (SEQ ID NO: 18) or CD8β (SEQ ID NO: 20). The epitope(s) may consist of one or more contiguous sequences of 3 or more (e.g., 3, 4, 5, 6, 7, 8, 9, 10, 11, 12, 13, 14, 15, 16, 17, 18, 19, 20 or more) amino acids located within the extracellular region of CD8α or CD8β. Alternatively, the epitope may consist of a plurality of non-contiguous amino acids (or amino acid sequences) located within the extracellular region of CD8α or CD8β.

The present disclosure includes anti-CD8 antibodies that bind to the same epitope, or a portion of the epitope, as the specific exemplary antibody described herein in Table 1, or an antibody having the CDR sequences of the exemplary antibody described in Table 1. Likewise, also included are anti-CD8 antibodies that compete for binding to CD8 or a CD8 fragment with the specific exemplary antibody described herein in Table 1, or an antibody having the CDR sequences of the exemplary antibody described in Table 1. For example, the present disclosure includes anti-CD8 antibodies that cross-compete for binding to CD8 with one or more antibodies provided herein (e.g., mAb1).

The antibodies and antigen-binding fragments described herein specifically bind to CD8 and modulate the interaction of CD8 with MHC class I. The anti-CD8 antibodies may bind to CD8 with high affinity or with low affinity. In certain embodiments, the antibodies are blocking antibodies wherein the antibodies bind to CD8 and block the interaction of CD8 with MHC class I. In some embodiments, the blocking antibodies of the disclosure block the binding of CD8 to MHC class I and/or mitigate T cell activation. In some embodiments, the blocking antibodies are useful for inhibiting the immune response and/or for treating an infection or autoimmune disease or disorder.

In some embodiments, the antibodies bind to CD8 and inhibits IFNγ production in activated CD8 positive T cells. In certain embodiments, the antibodies bind to CD8 and inhibit regulatory T cell activity, e.g. inhibit the transcription factor AP-1 in CD8 positive T cells.

Certain anti-CD8 antibodies are able to bind to and neutralize the activity of CD8, as determined by in vitro or in vivo assays. The ability of the antibodies to bind to and neutralize the activity of CD8 may be measured using any standard method known to those skilled in the art, including binding assays, or activity assays, as described herein.

Non-limiting, exemplary in vitro assays for measuring binding activity are illustrated in Examples provided herein: in Example 2, the binding affinities and kinetic constants of an exemplary human anti-CD8 antibody for human CD8 were determined by surface plasmon resonance and the measurements were conducted on a Biacore 4000 or T200 instrument; in Example 6, a fluorescence assay was used to determine the ability of anti-CD8 antibodies to bind to CD8 positive T cells and cynomolgus monkey T cells; in Example 7, binding assays were used to determine the ability of anti-CD8 antibodies to decrease IFNγ production in CD8 positive T cells; and in Example 8, binding assays were used to determine the ability of the anti-CD8 antibodies to alter T cell transcriptional activity.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to CD8. An antibody fragment may include a Fab fragment, a F(ab')$_2$ fragment, a Fv fragment, a dAb fragment, a fragment containing a CDR, or an isolated CDR. In certain embodiments, the term "antigen-binding fragment" refers to a polypeptide or fragment thereof of a multi-specific antigen-binding molecule. In such embodiments, the term "antigen-binding fragment" includes, e.g., MHC class II molecule which binds specifically to CD8. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H^2$—$C_H^3$; (vii) $V_H$-$C_L$; (viii) $V_L$-$C_H$1; (ix) $V_L$-$C_H$2; (X) $V_L$-$C_H$3; (Xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The anti-CD8 antibodies and antibody fragments of the present disclosure encompass proteins having amino acid sequences that vary from those of the described antibodies, but that retain the ability to bind CD8. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment of the disclosure.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a subject can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-CD8 Antibodies Comprising Fc Variants

According to certain embodiments of the present disclosure, anti-CD8 antibodies comprise an Fc domain comprising one or more mutations which enhance or diminish antibody binding to the FcRn receptor, e.g., at acidic pH as compared to neutral pH. For example, the present disclosure includes anti-CD8 antibodies comprising a mutation in the $C_H$2 or a $C_H$3 region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present disclosure includes anti-CD8 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q31 1I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). In one embodiment, the present disclosure includes anti-CD8 antibodies comprising an Fc domain comprising a S108P mutation in the hinge region of IgG4 to promote dimer stabilization. All possible combinations of the foregoing Fc domain mutations, and other mutations within the antibody variable domains disclosed herein, are contemplated within the scope of the present disclosure.

The present disclosure also includes anti-CD8 antibodies comprising a chimeric heavy chain constant ($C_H$) region, wherein the chimeric $C_H$ region comprises segments derived from the $C_H$ regions of more than one immunoglobulin isotype. For example, the antibodies of the disclosure may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the disclosure comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., US Patent Publication No. 20140243504, the disclosure of which is hereby incorporated by reference in its entirety).

B. Positron Emitters and Chelating Moieties

Suitable positron emitters include, but are not limited to, those that form stable complexes with the chelating moiety and have physical half-lives suitable for immuno-PET imaging purposes. Illustrative positron emitters include, but are not limited to, $^{89}$Zr, $^{68}$Ga, $^{64}$CU, $^{44}$Sc, and $^{86}$Y. Suitable positron emitters also include those that directly bond with the CD8 binding protein, including, but not limited to, $^{76}$Br and $^{124}$I, and those that are introduced via prosthetic group, e.g., $^{18}$F.

The chelating moieties described herein are chemical moieties that are covalently linked to the CD8 binding protein, e.g., anti-CD8 antibody and comprise a portion capable of chelating a positron emitter, i.e., capable of reacting with a positron emitter to form a coordinated chelate complex. Suitable moieties include those that allow efficient loading of the particular metal and form metal-chelator complexes that are sufficiently stable in vivo for diagnostic uses, e.g., immuno-PET imaging. Illustrative chelating moieties include those that minimize dissociation of the positron emitter and accumulation in mineral bone, plasma proteins, and/or bone marrow depositing to an extent suitable for diagnostic uses.

Examples of chelating moieties include, but are not limited to, those that form stable complexes with positron emitters $^{89}$Zr, $^{68}$Ga, $^{64}$Cu, $^{44}$Sc, and/or $^{86}$Y. Illustrative chelating moieties include, but are not limited to, those described in *Nature Protocols*, 5(4): 739, 2010; *Bioconjugate Chem.*, 26(12): 2579 (2015); *Chem Commun (Camb)*, 51(12): 2301 (2015); *Mol. Pharmaceutics*, 12: 2142 (2015); *Mol. Imaging Biol.*, 18: 344 (2015); *Eur. J. Nucl. Med. Mol. Imaging*, 37:250 (2010); *Eur. J. Nucl. Med. Mol. Imaging* (2016). doi:10.1007/s00259-016-3499-x; Bioconjugate Chem., 26(12): 2579 (2015); WO 2015/140212A1; and U.S. Pat. No. 5,639,879, incorporated by reference in their entireties.

Illustrative chelating moieties also include, but are not limited to, those that comprise desferrioxamine (DFO), 1,4,7,10-tetraacetic acid (DOTA), diethylenetriaminepentaacetic acid (DTPA), ethylenediaminetetraacetic acid (EDTA), (1,4,7,10-Tetraazacyclododecane-1,4,7,10-tetra (methylene phosphonic) acid (DOTP), 1R, 4R, 7R, 10R)-α'α"α'"-Tetramethyl-1,4,7,10-tetraazacyclododecane-1,4,7,10-tetraacetic acid (DOTMA), 1,4,8,11-Tetraazacyclotetradecane-1,4,8,11-tetraacetic acid (TETA), H$_4$octapa, H$_6$phospa, H$_2$dedpa, H$_5$decapa, H$_2$azapa, HOPO, DO2A, 1,4,7,10-Tetrakis(carbamoylmethyl)-1,4,7,10-tetraazacyclododecane (DOTAM), 1,4,7-triazacyclononane-N,N',N"-triacetic acid (NOTA), 1,4,7,10-Tetrakis(carbamoylmethyl)-1,4,7,10-tetraazacyclododecane (DOTAM), 1,4,8,11-tetraazabicyclo[6.6.2]hexadecane-4,11-dicetic acid (CB-TE2A), 1,4,7,10-Tetraazacyclododecane (Cyclen), 1,4,8,11-Tetraazacyclotetradecane (Cyclam), octadentate chelators, hexadentate chelators, phosphonate-based chelators, macrocyclic chelators, chelators comprising macrocyclic terephthalamide ligands, bifunctional chelators, fusarinine C and fusarinine C derivative chelators, triacetylfusarinine C (TAFC), ferrioxamine E (FOXE), ferrioxamine B (FOXB), ferrichrome A (FCHA), and the like.

In some embodiments, the chelating moieties are covalently bonded to the CD8 binding protein, e.g., antibody or antigen-binding fragment thereof, via a linker moiety, which covalently attaches the chelating portion of the chelating moiety to the binding protein. In some embodiments, these linker moieties are formed from a reaction between a reactive moiety of the CD8 binding protein, e.g., cysteine or lysine of an antibody, and reactive moiety that is attached to a chelator, including, for example, a p-isothiocyanatobenyl group and the reactive moieties provided in the conjugation methods below. In addition, such linker moieties optionally comprise chemical groups used for purposes of adjusting polarity, solubility, steric interactions, rigidity, and/or the length between the chelating portion and the CD8 binding protein.

C. Preparation of Radiolabeled Anti-CD8 Conjugates

The radiolabeled anti-CD8 protein conjugates can be prepared by (1) reacting a CD8 binding protein, e.g., antibody, with a molecule comprising a positron emitter chelator and a moiety reactive to the desirable conjugation site of the CD8 binding protein and (2) loading the desirable positron emitter.

Suitable conjugation sites include, but are not limited to, lysine and cysteine, both of which can be, for example, native or engineered, and can be, for example, present on the heavy or light chain of an antibody. Cysteine conjugation sites include, but are not limited to, those obtained from mutation, insertion, or reduction of antibody disulfide bonds. Methods for making cysteine engineered antibodies include, but are not limited to, those disclosed in WO2011/056983. Site-specific conjugation methods can also be used to direct the conjugation reaction to specific sites of an antibody, achieve desirable stoichiometry, and/or achieve desirable chelator-to-antibody ratios. Such conjugation methods are known to those of ordinary skill in the art and include, but are not limited to cysteine engineering and enzymatic and chemo-enzymatic methods, including, but not limited to, glutamine conjugation, Q295 conjugation, and transglutaminase-mediated conjugation, as well as those described in *J. Clin. Immunol.*, 36: 100 (2016), incorporated herein by reference in its entirety. Suitable moieties reactive to the desirable conjugation site generally enable efficient and facile coupling of the CD8 binding protein, e.g., antibody and positron emitter chelator. Moieties reactive to lysine and cysteine sites include electrophilic groups, which are known to those of ordinary skill. In certain aspects, when the desired conjugation site is lysine, the reactive moiety is an isothiocyanate, e.g., p-isothiocyanatobenyl group or reactive ester. In certain aspects, when the desired conjugation site is cysteine, the reactive moiety is a maleimide.

When the chelator is desferrioxamine (DFO), suitable reactive moieties include, but are not limited to, an isothiocyantatobenzyl group, an n-hydroxysuccinimide ester, 2,3, 5,6 tetrafluorophenol ester, n-succinimidyl-S-acetylthioacetate, and those described in *BioMed Research International*, Vol 2014, Article ID 203601, incorporated herein by reference in its entirety. In certain embodiments, the CD8 binding protein is an antibody and the molecule comprising a positron emitter chelator and moiety reactive to the conjugation site is p-isothiocyantatobenzyl-desferrioxamine (p-SCN-Bn-DFO):

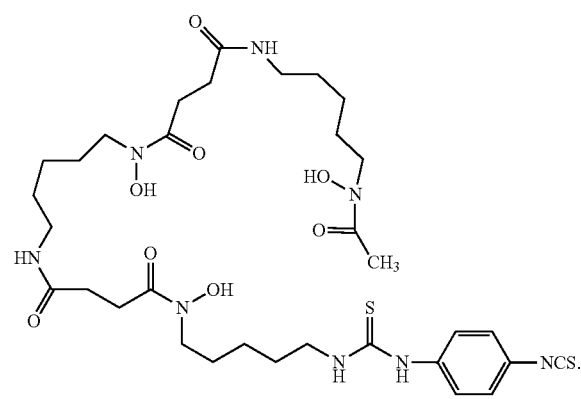

Positron emitter loading is accomplished by incubating the CD8 binding protein chelator conjugate with the positron emitter for a time sufficient to allow coordination of said positron emitter to the chelator, e.g., by performing the methods described in the examples provided herein, or substantially similar method.

D. Illustrative Embodiments of Conjugates

Included in the instant disclosure are radiolabeled antibody conjugates comprising an antibody or antigen-binding fragment thereof that binds human CD8 and a positron emitter. Also included in the instant disclosure are radiolabeled antibody conjugates comprising an antibody or antigen-binding fragment thereof that binds human CD8, a chelating moiety, and a positron emitter.

In some embodiments, the chelating moiety comprises a chelator capable of forming a complex with $^{89}$Zr. In certain embodiments, the chelating moiety comprises desferrioxamine. In certain embodiments, the chelating moiety is p-isothiocyanatobenzyl-desferrioxamine.

In some embodiments, the positron emitter is $^{89}$Zr. In some embodiments, less than 1.0% of the anti-CD8 antibody is conjugated with the positron emitter, less than 0.9% of the anti-CD8 antibody is conjugated with the positron emitter, less than 0.8% of the anti-CD8 antibody is conjugated with the positron emitter, less than 0.7% of the anti-CD8 antibody is conjugated with the positron emitter, less than 0.6% of the anti-CD8 antibody is conjugated with the positron emitter, less than 0.5% of the anti-CD8 antibody is conjugated with the positron emitter, less than 0.4% of the anti-CD8 antibody is conjugated with the positron emitter, less than 0.3% of the anti-CD8 antibody is conjugated with the positron emitter, less than 0.2% of the anti-CD8 antibody is conjugated with the positron emitter, or less than 0.1% of the anti-CD8 antibody is conjugated with the positron emitter.

In some embodiments, the chelating moiety-to-antibody ratio of the conjugate is from 1.0 to 2.0. As used herein, "chelating moiety-to-antibody ratio" is the average chelator moiety to antibody ratio and is a measure of chelator load per antibody. This ratio is analogous to "DAR", i.e., drug-antibody ratio, which is used by those skilled in the art to measure drug load per antibody for antibody-drug conjugates (ADCs); in the context of the conjugates described herein for iPET imaging, the chelating moiety-to-antibody ratio can be ascertained using methods described herein and others known in the art for the determination of DAR, e.g. those described in Wang et al., Antibody-Drug Conjugates, The 21$^{st}$ Century Magic Bullets for Cancer (2015). In some embodiments, the chelating moiety-to-antibody ratio is about 1.7. In some embodiments, the chelating moiety-to-antibody ratio is from 1.0 to 2.0. In some embodiments, the chelating moiety-to-antibody ratio is about 1.7.

In a particular embodiment, the chelating moiety is p-isothiocyanatobenzyl-desferrioxamine and the positron emitter is $^{89}$Zr. In another particular embodiment, the chelating moiety is p-isothiocyanatobenzyl-desferrioxamine and the positron emitter is $^{89}$Zr, and the chelating moiety-to-antibody ratio of the conjugate is from 1 to 2.

In some embodiments, provided herein are antigen-binding proteins that bind CD8, wherein said antigen-binding proteins that bind CD8 are covalently bonded to one or more moieties having the following structure:

$$-L-M_Z$$

wherein L is a chelating moiety; M is a positron emitter; and z, independently at each occurrence, is 0 or 1; and wherein at least one of z is 1. In certain embodiments, the radiolabeled antigen-binding protein is a compound of Formula (I):

$$M-L-A-[L-M_Z]_k \quad (I)$$

A is a protein that binds CD8; L is a chelating moiety; M is a positron emitter; z is 0 or 1; and k is an integer from 0-30. In some embodiments, k is 1. In some embodiments, k is 2.

In some embodiments, L is:

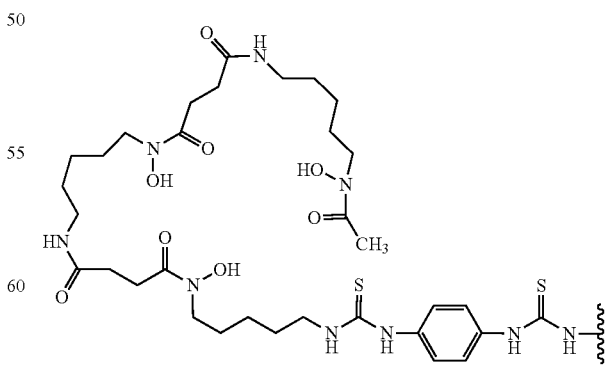

In some embodiments, M is $^{89}$Zr.

In some embodiments, k is an integer from 1 to 2. In some embodiments, k is 1. In some embodiments, k is 2.

In some embodiments, -L-M is

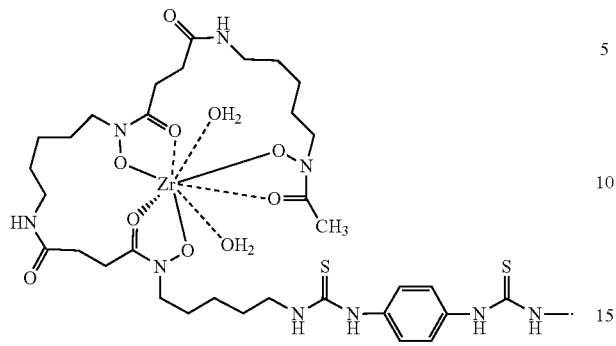

Included in the instant disclosure are also methods of synthesizing a radiolabeled antibody conjugate comprising contacting a compound of Formula (III):

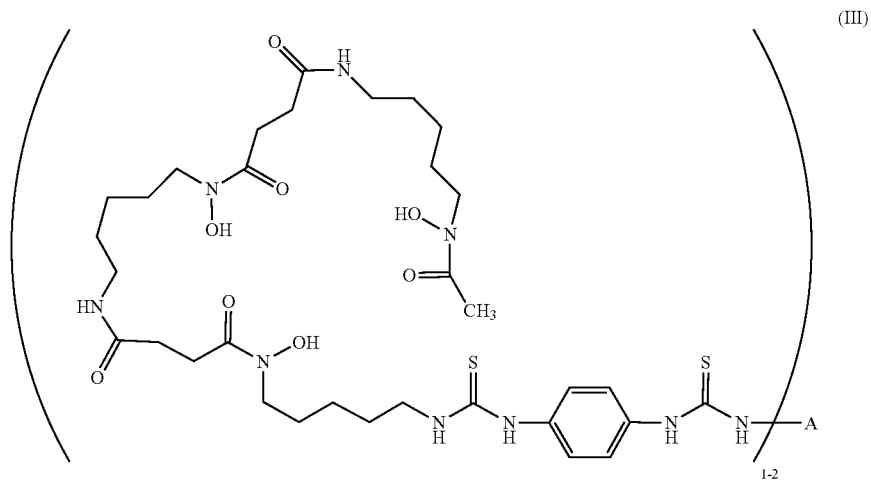

with $^{89}$Zr, wherein A is an antibody or antigen-binding fragment thereof that binds CD8. In certain embodiments, the compound of Formula (III) is synthesized by contacting an antibody, or antigen-binding fragment thereof, that binds CD8, with p-SCN-Bn-DFO.

Provided herein is also the product of the reaction between a compound of Formula (III) with $^{89}$Zr.

Provided herein are compounds of Formula (III):

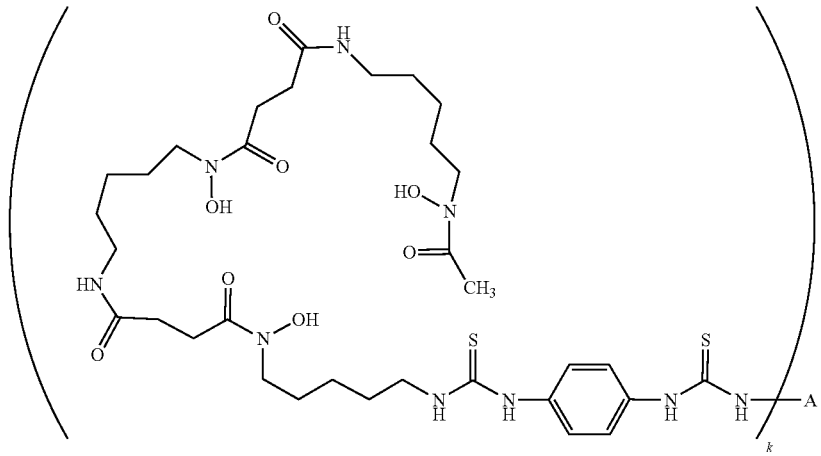

wherein A is an antibody or antigen-binding fragment thereof that binds CD8 and k is an integer from 1-30. In some embodiments, k is 1 or 2.

Provided herein are antibody conjugates comprising (i) an antibody or antigen-binding fragment thereof that binds CD8 and (ii) one or more chelating moieties.

In some embodiments, the chelating moiety comprises:

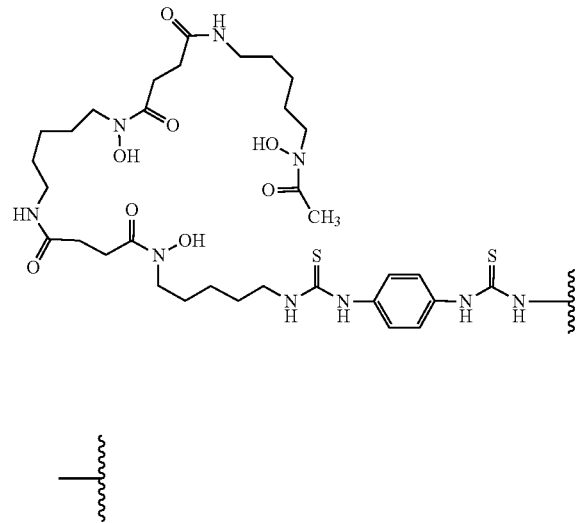

is a covalent bond to the antibody or antigen-binding fragment thereof.

In some aspects, the antibody conjugate has a chelating moiety-to-antibody ratio of from about 1.0 to about 2.0. In some aspects, the antibody conjugate has a chelating moiety-to-antibody ratio of about 1.7.

In some embodiments, provided herein are compositions comprising a conjugate having the following structure:

A-L$_k$ wherein A is a protein that binds CD8; L is a chelating moiety; and k is an integer from 1-30; the conjugate is chelated with a positron emitter in an amount sufficient to provide a specific activity suitable for clinical PET imaging. In some embodiments, the amount of chelated positron emitter is an amount sufficient to provide a specific activity of about 1 to about 50 mCi per 1-50 mg of the protein that binds CD8.

In some embodiments, the amount of chelated positron emitter is an amount sufficient to provide a specific activity of up to 50 mCi, up to 45 mCi, up to 40 mCi, up to 35 mCi, up to 30 mCi, up to 25 mCi, or up to 10 mCi per 1-50 mg of the protein that binds CD8, for example, in a range of about 5 to about 50 mCi, about 10 to about 40 mCi, about 15 to about 30 mCi, about 7 to about 25 mCi, about 20 to about 50 mCi, or about 5 to about 10 mCi.

In some embodiments, the antibody or antigen-binding fragment thereof binds human CD8 with a binding dissociation equilibrium constant ($K_D$) of less than about $3.5 \times 10^{-8}$ M as measured in a surface plasmon resonance assay.

In some embodiments, the antibody or antigen-binding fragment thereof binds human CD8α with a $K_D$ less than about $3.5 \times 10^{-8}$ in a surface plasmon resonance assay.

In some embodiments, the antibody or antigen-binding fragment thereof binds human CD8 with a $K_D$ of less than about $3.3 \times 10^{-8}$ M as measured in a surface plasmon resonance assay.

In some embodiments, the antibody or antigen-binding fragment thereof competes for binding to human CD8 with a reference antibody comprising the complementarity determining regions (CDRs) of a HCVR, wherein the HCVR has an amino acid sequence of SEQ ID NO: 2; and the CDRs of a LCVR, wherein the LCVR has an amino acid sequence of SEQ ID NO: 10. In some embodiments, the reference antibody or antigen-binding fragment thereof comprises an HCVR/LCVR amino acid sequence pair of SEQ ID NOs: 2/10.

In some embodiments, the antibody or antigen-binding fragment thereof inhibits CD8 binding to MHC class I. In some embodiments, the antibody or antigen-binding fragment thereof inhibits IFNγ production in activated CD8 T cells. In some embodiments, the antibody or antigen-binding fragment thereof inhibits transcription factor activator-protein (AP-1) in activated T cells.

In some embodiments, the antibody or antigen-binding fragment thereof comprises the complementarity determining regions (CDRs) of a HCVR, wherein the HCVR has an amino acid sequence of SEQ ID NO: 2; and the CDRs of a LCVR, wherein the LCVR has an amino acid sequence of SEQ ID NO: 10. In certain embodiments, the isolated antibody comprises an HCVR/LCVR amino acid sequence pair of SEQ ID NOs: 2/10.

In some embodiments, the antibody is a human monoclonal antibody or antigen-binding fragment thereof that binds specifically to human CD8, wherein the antibody or antigen-binding fragment thereof comprises a heavy chain variable region (HCVR) having an amino acid sequence of SEQ ID NO: 2.

In some embodiments, the antibody is a human monoclonal antibody or antigen-binding fragment thereof that binds specifically to human CD8, wherein the antibody or antigen-binding fragment thereof comprises a light chain variable region (LCVR) having an amino acid sequence of SEQ ID NO: 10.

In some embodiments, the antibody is a human monoclonal antibody or antigen-binding fragment thereof that binds specifically to human CD8, wherein the antibody or antigen-binding fragment thereof comprises (a) a HCVR having an amino acid sequence of SEQ ID NO: 2; and (b) a LCVR having an amino acid sequence of SEQ ID NO: 10.

In some embodiments, the antibody or antigen-binding fragment thereof comprises three heavy chain complementarity determining regions (CDRs) (HCDR1, HCDR2 and HCDR3) contained within the heavy chain variable region (HCVR) of SEQ ID NO: 2; and three light chain CDRs (LCDR1, LCDR2 and LCDR3) contained within the light chain variable region (LCVR) of SEQ ID NO: 10.

In some embodiments, the antibody or antigen-binding fragment thereof comprises a six CDR amino acid sequence combination of SEQ ID NOs: 4/6/8/12/14/16.

In some embodiments, the antibody or antigen-binding fragment comprises a HCVR/LCVR amino acid sequence pair of SEQ ID NOs: 2/10.

IV. Methods of Using Radiolabeled Immunoconjugates

In certain aspects, the present disclosure provides diagnostic and therapeutic methods of use of the radiolabeled antibody conjugates of the present disclosure.

According to one aspect, the present disclosure provides methods of detecting CD8 in a tissue, the methods comprising administering a radiolabeled anti-CD8 antibody conjugate of the provided herein to the tissue; and visualizing the CD8 expression by positron emission tomography (PET) imaging. In certain embodiments, the tissue comprises cells or cell lines. In certain embodiments, the tissue is present in a subject, wherein the subject is a mammal. In certain embodiments, the subject is a human subject. In certain embodiments, the subject has a disease or disorder selected from the group consisting of cancer, infectious disease, autoimmune disease, and inflammatory disease. In one embodiment, the subject has cancer. In certain embodiments, the infectious disease is a bacterial infection caused by, for example, rickettsial bacteria, bacilli, klebsiella, meningococci and gonococci, proteus, pneumonococci, pseudomonas, streptococci, staphylococci, serratia, Borriella, Bacillus anthricis, Chlamydia, Clostridium, Corynebacterium diphtheriae, Legionella, Mycobacterium leprae, Mycobacterium lepromatosis, Salmonella, Vibrio cholerae, and Yersinia pestis. In certain embodiments, the infectious disease is a viral infection caused by, for example, human immunodeficiency virus (HIV), hepatitis C virus (HCV), hepatitis B virus (HBV), herpes virus (e.g., VZV, HSV-1, HAV-6, HSV-II, CMV, and Epstein Barr virus), human papilloma virus (HPV), lymphocytic choriomeningitis virus (LCMV), and simian immunodeficiency virus (SIV). In certain embodiments, the infectious disease is a parasitic infection caused by, for example, Entamoeba spp., Enterobius vermicularis, Leishmania spp., Toxocara spp., Plasmodium spp., Schistosoma spp., Taenia solium, Toxoplasma gondii, and Trypanosoma cruzi. In certain embodiments, the infectious disease is a fungal infection caused by, for example, Aspergillus (fumigatus, niger, etc.), Blastomyces dermatitidis, Candida (albicans, krusei, glabrata, tropicalis, etc.), Coccidioides immitis, Cryptococcus neoformans, Genus Mucorales (mucor, absidia, rhizopus, etc.), Histoplasma capsulatum, Paracoccidioides brasiliensis, and *Sporothrix schenkii*.

According to one aspect, the present disclosure provides methods of imaging a tissue that expresses CD8 comprising administering a radiolabeled anti-CD8 antibody conjugate of the present disclosure to the tissue; and visualizing the CD8 expression by positron emission tomography (PET) imaging. In one embodiment, the tissue is comprised in a tumor. In one embodiment, the tissue is comprised in a tumor cell culture or tumor cell line. In one embodiment, the tissue is comprised in a tumor lesion in a subject. In one embodiment, the tissue is intratumoral lymphocytes in a tissue. In one embodiment, the tissue comprises CD8-expressing cells.

According to one aspect, the present disclosure provides methods for measuring response to a therapy, wherein the response to a therapy is correlated with an increase in CD8 positive T cells relative to baseline levels. The methods, according to this aspect, comprise administering a radiolabeled antibody conjugate provided herein to a subject in need thereof and visualizing the CD8 expression by positron emission tomography (PET) imaging. In certain embodiments, the CD8 positive T cells are present in a tumor in the subject. In certain embodiments, an increase in CD8 expression correlates to increase in inflammation in a tumor. In certain embodiments, the inflammation is present in an infected tissue in the subject. In certain embodiments, a decrease in CD8 expression correlates to a decrease in inflammation in an infected tissue.

According to one aspect, the present disclosure provides methods for measuring response to a therapy, wherein the response to a therapy is correlated with increased CD8 positive T cells relative to baseline levels. The methods, according to this aspect, comprise (i) administering a radiolabeled antibody conjugate provided herein to a subject in need thereof and visualizing the CD8 expression by positron emission tomography (PET) imaging, and (ii) repeating step (i) one or more times after initiation of therapy. In certain embodiments, the CD8 positive T cells are present in a tissue in the subject. In certain embodiments, an increase in CD8 expression correlates to increase in inflammation in the tissue. In certain embodiments, a decrease in CD8 expression correlates to a decrease in inflammation in the tissue. In certain embodiments, CD8 expression visualized in step (i) is compared to CD8 expression visualized in step (ii).

According to one aspect, the present disclosure provides methods for predicting a response to anti-tumor therapy. The method comprises administering radiolabeled anti-CD8 antibody conjugate to a subject in need thereof, and determining that the subject's solid tumor comprises CD8 positive T cells. If the subject's tumors are infiltrated with CD8 positive T cells, or immunologically 'hot,' the subject will likely respond to anti-tumor therapy. The presence of CD8 positive T cells can be a predictive marker of response or a prognostic marker for survival. For example, baseline tumor infiltration with CD8 positive cells is prognostic of survival in breast, head/neck, and ovarian cancer. In addition, tumor infiltration of CD8 positive cells detected during anti-PD-1 therapy or anti-PDL-1 therapy is a predictive marker of response to treatment.

According to one aspect, the present disclosure provides methods for determining if a subject having a tumor is suitable for anti-tumor therapy, the methods comprising administering a radiolabeled antibody conjugate of the present disclosure, and localizing the administered radiolabeled antibody conjugate in the tumor by PET imaging wherein presence of the radiolabeled antibody conjugate in the tumor identifies the subject as suitable for anti-tumor therapy.

According to one aspect, the present disclosure provides methods for identifying a subject having a tumor for anti-tumor therapy comprising an inhibitor of the PD-1/PD-L1 signaling axis, the methods comprising administering a radiolabeled antibody conjugate of the present disclosure to the subject, and localizing the administered radiolabeled antibody conjugate in the tumor by PET imaging wherein presence of the radiolabeled antibody conjugate in the tumor identifies the subject as suitable for anti-tumor therapy. In some embodiments, the subject is further administered a radiolabeled anti-PD-1 conjugate and the administered radiolabeled anti-PD-1 conjugate is localized in the tumor by PET imaging, wherein presence of the radiolabeled antibody conjugate in the tumor identifies the subject as suitable for anti-tumor therapy comprising an inhibitor of the PD-1/PD-L1 signaling axis.

Another aspect of the present disclosure provides methods for monitoring T-cell presence and/or infiltration in a tumor over time. In some embodiments, the method comprises (a) administering a radiolabeled anti-CD8 antibody conjugate at a first timepoint to a subject having the tumor and determining the presence of CD8 positive T-cells in the tumor; (b) administering one or more doses of an anti-tumor therapy to the subject; and (c) administering a radiolabeled anti-CD8 antibody conjugate at a second timepoint to the subject 1 to 20 weeks after administration of the anti-tumor therapy and determining the presence of CD8 positive T-cells in the tumor. The presence of T-cells in the tumor indicates a positive response to the anti-tumor therapy. Step (c) can be repeated over the course of treatment with the anti-tumor therapy. The first timepoint can occur prior to (b) or can occur after (b).

Determining the presence of T-cells in a tumor may involve quantifying the levels of T-cells by methods known to one of skill in the art. In some aspects, baseline levels of CD8 positive T-cells are compared to the levels CD8 positive T-cells measured after or during a course of anti-tumor therapy. Maintaining CD8 positive T-cell levels relative to baseline, or an increase in CD8 positive T-cells over time, indicates a positive response to the anti-tumor therapy.

Determining the presence of T-cells in a tumor may involve a simple determination—the tumor is T-cell positive or the tumor is T-cell negative.

Provided herein are also methods for predicting response of a subject to an anti-tumor therapy, the methods comprising determining if the tumor is CD8 positive, wherein if the tumor is CD8 positive, i.e. the tumor contains T-cells, it predicts a positive response of the subject to an anti-tumor therapy. In certain embodiments, the tumor is determined positive by administering a radiolabeled anti-CD8 antibody conjugate of the present disclosure and localizing the radiolabeled antibody conjugate in the tumor by PET imaging wherein presence of the radiolabeled antibody conjugate in the tumor indicates that the tumor is CD8 positive. In some embodiments, the anti-tumor therapy is a checkpoint inhibitor therapy. In some embodiments, the anti-tumor therapy is selected from a PD-1 inhibitor (e.g., REGN2810, BGB-A317, nivolumab, pidilizumab, and pembrolizumab), a PD-L1 inhibitor (e.g., atezolizumab, avelumab, durvalumab, MDX-1105, and REGN3504, as well as those disclosed in Patent Publication No. US 2015-0203580), CTLA-4 inhibitor (e.g., ipilimumab), a TIM3 inhibitor, a BTLA inhibitor, a TIGIT inhibitor, a CD47 inhibitor, a GITR inhibitor, a LAG3 inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen-binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3xCD20 bispecific antibody, or PSMAxCD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, and an antibody-drug conjugate (ADC) (e.g., anti-CD19-DM4 ADC, and anti-DS6-DM4 ADC).

According to one aspect, the present disclosure provides methods for predicting response of a subject having a solid tumor to an anti-tumor therapy, the methods comprising determining if the tumor is CD8 positive, wherein a positive response of the subject is predicted if the tumor is CD8 positive. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is CD8 positive.

According to one aspect, the present disclosure provides methods for detecting a CD8 positive tumor in a subject. The methods, according to this aspect, comprise administering a radiolabeled antibody conjugate of the present disclosure to the subject; and determining localization of the radiolabeled antibody conjugate by PET imaging, wherein presence of the radiolabeled antibody conjugate in a tumor indicates that the tumor is CD8 positive.

Provided herein are methods for predicting a positive response to an anti-tumor therapy comprising: administering a radiolabeled anti-CD8 antibody conjugate to the subject determine the presence of CD8-positive T-cells in the solid tumor. The presence of CD8-positive T-cells predicts a positive response to an anti-tumor therapy.

Provided herein are methods for monitoring a positive response to an anti-tumor therapy in a subject comprising: (a) administering one or more doses of an anti-tumor therapy to the subject; and (b) administering a radiolabeled anti-CD8 antibody conjugate to the subject 1 to 20 weeks after administration of the anti-tumor therapy to determine the presence of CD8-positive cells in the solid tumor. The presence of CD8-positive T-cells indicates a positive response to the anti-tumor therapy.

Provided herein are methods for predicting or monitoring success or efficacy of anti-tumor therapy in a subject having a solid tumor, the method comprising: (a) determining the level of CD8 positive cells in the tumor; and (b) correlating the level of CD8 positive cells with successful anti-tumor therapy. An elevated level above a certain threshold is predictive or indicative of successful anti-tumor therapy.

As used herein, the expression "a subject in need thereof" means a human or non-human mammal that exhibits one or more symptoms or indications of cancer, and/or who has been diagnosed with cancer, including a solid tumor and who needs treatment for the same. In many embodiments, the term "subject" may be interchangeably used with the term "patient". For example, a human subject may be diagnosed with a primary or a metastatic tumor and/or with one or more symptoms or indications including, but not limited to, unexplained weight loss, general weakness, persistent fatigue, loss of appetite, fever, night sweats, bone pain, shortness of breath, swollen abdomen, chest pain/pressure, enlargement of spleen, and elevation in the level of a cancer-related biomarker (e.g., CA125). The expression includes subjects with primary or established tumors. In specific embodiments, the expression includes human subjects that have and/or need treatment for a solid tumor, e.g., colon cancer, breast cancer, lung cancer, prostate cancer, skin cancer, liver cancer, bone cancer, ovarian cancer, cervical cancer, pancreatic cancer, head and neck cancer, and brain cancer. The term includes subjects with primary or metastatic tumors (advanced malignancies). In certain embodiments, the expression "a subject in need thereof" includes subjects with a solid tumor that is resistant to or refractory to or is inadequately controlled by prior therapy (e.g., treatment with an anti-cancer agent). For example, the expression includes subjects who have been treated with one or more lines of prior therapy such as treatment with chemotherapy (e.g., carboplatin or docetaxel). In certain embodiments, the expression "a subject in need thereof" includes subjects with a solid tumor which has been treated with one or more lines of prior therapy but which has subsequently relapsed or metastasized. In certain embodiments, the term includes subjects having an inflammatory disease or disorder including, but not limited to, cancer, rheumatoid arthritis, atherosclerosis, periodontitis, hay fever, heart disease, coronary artery disease, infectious disease, bronchitis, dermatitis, meningitis, asthma, tuberculosis, ulcerative colitis, Crohn's disease, inflammatory bowel disease, hepatitis, sinusitis, psoriasis, allergy, fibrosis, lupus, vasculitis, ankylosing spondylitis, Graves' disease, Celiac disease, fibromyalgia, and transplant rejection.

In certain embodiments, the methods of the present disclosure are used in a subject with a solid tumor. The terms "tumor", "cancer" and "malignancy" are interchangeably used herein. As used herein, the term "solid tumor" refers to an abnormal mass of tissue that usually does not contain cysts or liquid areas. Solid tumors may be benign (not cancer) or malignant (cancer). For the purposes of the present disclosure, the term "solid tumor" means malignant solid tumors. The term includes different types of solid tumors named for the cell types that form them, viz. sarcomas, carcinomas and lymphomas. In certain embodiments, the term "solid tumor" includes cancers including, but not limited to, colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, and myeloma.

According to one aspect, the present disclosure provides methods of treating a solid tumor in a subject. The methods, according to this aspect, comprise determining that the tumor is CD8 positive, i.e. the tumor comprises CD8 positive T-cells; and administering one or more doses of an anti-tumor therapy. The anti-tumor therapy can be a checkpoint inhibitor therapy. In certain embodiments, the tumor is determined to be CD8 positive by administering a radiolabeled antibody conjugate of the present disclosure to the subject; and visualizing the radiolabeled antibody conjugate in the tumor by PET imaging. Presence of the radiolabeled antibody conjugate in the tumor indicates that the tumor is CD8 positive.

A radiolabeled anti-CD8 antibody disclosed herein can be used to assess whether a subject is suitable for checkpoint inhibitor therapy. In some aspects, a radiolabeled anti-CD8 antibody can be used to monitor T-cell infiltration in a tumor, including for example, monitoring without the need to do a biopsy of the tumor. In certain embodiments, sufficient T-cell infiltration is indicative that the tumor will respond to checkpoint inhibitor therapy. A radiolabeled anti-CD8 antibody disclosed herein can also be used to monitor T-cell infiltration over the course of or after checkpoint inhibitor treatment, e.g., by measuring the change in extent of T-cell infiltration at time points before and/or over the course of treatment.

The presence of CD8 positive T-cells in a tumor is indicative that the tumor will respond better to treatment, for example, treatment with a checkpoint inhibitor therapy. In addition, the presence of CD8 positive T-cells in a tumor after treatment with an anti-tumor therapy is indicative that the therapy is working, and the greater the increase in T-cells, the more effective the treatment is.

In a further aspect, the methods of treating can further comprise administering one or more doses of a CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen-binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3xCD20 bispecific antibody, or PSMAxCD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as anti-oxidants or any other therapy care to treat cancer. In certain embodiments, the anti-tumor therapy may be used in combination with cancer vaccines including dendritic cell vaccines, oncolytic viruses, tumor cell vaccines, etc. to augment the anti-tumor response. Examples of cancer vaccines that can be used in combination with an anti-tumor therapy include MAGE3 vaccine for melanoma and bladder cancer, MUC1 vaccine for breast cancer, EGFRv3 (e.g., Rindopepimut) for brain cancer (including glioblastoma multiforme), or ALVAC-CEA (for CEA+ cancers).

In certain embodiments, the anti-tumor therapy may be used in combination with radiation therapy in methods to generate long-term durable anti-tumor responses and/or enhance survival of subjects with cancer. In some embodiments, an inhibitor of PD-1 or PDL-1, e.g. an anti-PD-1 antibody, may be administered prior to, concomitantly or after administering radiation therapy to a cancer subject. For example, radiation therapy may be administered in one or more doses to tumor lesions followed by administration of one or more doses of anti-PD-1 antibodies. In some embodiments, radiation therapy may be administered locally to a tumor lesion to enhance the local immunogenicity of a subject's tumor (adjuvinating radiation) and/or to kill tumor cells (ablative radiation) followed by systemic administration of an anti-PD-1 antibody. For example, intracranial radiation may be administered to a subject with brain cancer (e.g., glioblastoma multiforme) in combination with systemic administration of an anti-PD-1 antibody. In certain embodiments, the anti-PD-1 antibodies may be administered in combination with radiation therapy and a chemotherapeutic agent (e.g., temozolomide) or a VEGF antagonist (e.g., aflibercept).

In certain embodiments, the subject in need thereof can be administered anti-viral drugs to treat viral infection caused by, for example, LCMV, HIV, HPV, HBV or HCV. Examples of anti-viral drugs include, but are not limited to, zidovudine, lamivudine, abacavir, ribavirin, lopinavir, efavirenz, cobicistat, tenofovir, rilpivirine and corticosteroids.

In certain embodiments, the subject in need thereof can be administered one or more anti-bacterial drugs to treat bacterial infection caused by, for example, rickettsial bacteria, bacilli, klebsiella, meningococci and gonococci, proteus, pneumonococci, pseudomonas, streptococci, staphylococci, serratia, Borriella, Bacillus anthricis, Chlamydia, Clostridium, Corynebacterium diphtheriae, Legionella, Mycobacterium leprae, Mycobacterium lepromatosis, Salmonella, Vibrio cholerae, and Yersinia pestis. Examples of anti-bacterial drugs include, but are not limited to, penicillins, tetracyclines, cephalosporins, quinolones, lincomycins, macrolides, ketolides, sulfonamides, glycopeptides, aminoglycosides, and carbapenems.

In certain embodiments, the subject in need thereof can be administered one or more anti-fungal drugs to treat fungal infection caused by, for example, Aspergillus (fumigatus, niger, etc.), Blastomyces dermatitidis, Candida (albicans, krusei, glabrata, tropicalis, etc.), Coccidioides immitis, Cryptococcus neoformans, Genus Mucorales (mucor, absidia, rhizopus, etc.), Histoplasma capsulatum, Paracoccidioides brasiliensis, and Sporothrix schenkii. Examples of anti-fungal drugs include, but are not limited to, amphotericin B, fluconazole, vorixonazole, posaconazole, itraconazole, voriconazole, anidulafungin, caspofungin, micafungin, and flucytosine.

In certain embodiments, the subject in need thereof can be administered one or more anti-parasitic drugs to treat parasitic infection caused by, for example, *Entamoeba* spp., *Enterobius vermicularis, Leishmania* spp., *Toxocara* spp., *Plasmodium* spp., *Schistosoma* spp., *Taenia solium, Toxoplasma gondii*, and *Trypanosoma cruzi*. Examples of anti-parasitic drugs include, but are not limited to, praziquantel, oxamniquine, metronidazole, tinidazole, nitazoxanide, dehydroemetine or chloroquine, diloxanide furoate, iodoquinoline, chloroquine, paromomycin, pyrantel pamoate, albendazole, nifurtimox, and benznidazole.

The additional therapeutically active agent(s)/component(s) may be administered prior to, concurrent with, or after the administration of the inhibitor of CD8. For purposes of the present disclosure, such administration regimens are considered the administration of a CD8 inhibitor "in combination with" a second therapeutically active component.

In some aspects, the methods of treating comprise selecting a subject with a bacterial infection, a viral infection, a fungal infection, or a parasitic infection; determining that an affected tissue in the subject is CD8 positive; and administering one or more doses of a therapeutic agent appropriate to the infection. In certain embodiments, the affected tissue is determined to be CD8 positive by administering a radiolabeled anti-CD8 conjugate of the present disclosure to the subject; and visualizing the radiolabeled antibody conjugate in the subject by PET imaging, wherein presence of the radiolabeled antibody conjugate in a tissue indicates that the tissue is CD8 positive. In certain embodiments, the steps of administering and visualizing are performed one or more times in order to monitor the effectiveness of the therapeutic agent in treating the infection.

In some aspects, the methods of treating comprise selecting a subject with a solid tumor; determining that the tumor is CD8 positive and PD-1-positive; and administering one or more doses of an inhibitor of the PD-1/PD-L1 signaling axis (e.g., an anti-PD-1 antibody or an anti-PD-L1 antibody). In certain embodiments, the tumor is determined to be CD8 positive by administering a radiolabeled anti-CD8 conjugate of the present disclosure to the subject; and visualizing the radiolabeled antibody conjugate in the tumor by PET imaging, wherein presence of the radiolabeled antibody conjugate in the tumor indicates that the tumor is CD8 positive. In certain embodiments, the tumor is determined to be PD-1-positive by administering a radiolabeled anti-PD-1 conjugate of the present disclosure to the subject; and visualizing the radiolabeled anti-PD-1 conjugate in the tumor by PET imaging, wherein presence of the radiolabeled anti-PD-1 conjugate in the tumor indicates that the tumor is PD-1-positive.

Exemplary anti-PD-1 antibodies include REGN2810, BGB-A317, nivolumab, pidilizumab, and pembrolizumab.

Exemplary anti-PD-L1 antibodies include atezolizumab, avelumab, durvalumab, MDX-1105, and REGN3504, as well as those disclosed in Patent Publication No. US 2015-0203580.

As used herein, the terms "treat", "treating", or the like, mean to alleviate symptoms, eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, to prevent or inhibit metastasis, to inhibit metastatic tumor growth, and/or to increase duration of survival of the subject.

According to one aspect, the present disclosure provides methods for monitoring the efficacy of an anti-tumor therapy in a subject, wherein the methods comprise selecting a subject with a solid tumor wherein the subject is being treated with an anti-tumor therapy; administering a radiolabeled anti-CD8 conjugate of the present disclosure to the subject; imaging the localization of the administered radiolabeled conjugate in the tumor by PET imaging; and determining tumor growth, wherein a decrease from the baseline in radiolabeled signal indicates efficacy of the anti-tumor therapy. In certain embodiments, the anti-tumor therapy comprises an inhibitor of the PD-1/PD-L1 signaling axis (e.g., an anti-PD-1 antibody or an anti-PD-L1 antibody).

In certain embodiments, the present disclosure provides methods to assess changes in the inflammatory state of a tumor, the methods comprising selecting a subject with a solid tumor wherein the subject is being treated with an anti-tumor therapy; administering a radiolabeled anti-CD8 conjugate provided herein to the subject; and imaging the localization of the administered radiolabeled conjugate in the tumor by PET imaging, wherein an increase from the baseline in radiolabeled signal indicates increase in inflammation and efficacy of the anti-tumor therapy. In certain embodiments, the anti-tumor therapy comprises an inhibitor of the PD-1/PD-L1 signaling axis (e.g., an anti-PD-1 antibody or an anti-PD-L1 antibody). In certain embodiments, the anti-tumor therapy comprises a PD-1 inhibitor (e.g., REGN2810, BGB-A317, nivolumab, pidilizumab, and pembrolizumab), a PD-L1 inhibitor (e.g., atezolizumab, avelumab, durvalumab, MDX-1105, and REGN3504), CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen-binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3xCD20 bispecific antibody, or PSMAxCD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, and an antibody-drug conjugate (ADC) (e.g., anti-CD19-DM4 ADC, and anti-DS6-DM4 ADC).

As used herein, the term "baseline," with respect to CD8 expression in the tumor, means the numerical value of uptake of the radiolabeled conjugate for a subject prior to or at the time of administration of a dose of anti-tumor therapy. The uptake of the radiolabeled conjugate is determined using methods known in the art (see, for example, Oosting et al 2015, J. Nucl. Med. 56: 63-69). In certain embodiments, the anti-tumor therapy comprises an inhibitor of the PD-1/PD-L1 signaling axis.

To determine whether there is efficacy in anti-tumor therapy, the uptake of the radiolabeled conjugate is quantified at baseline and at one or more time points after administration of the CD8 inhibitor. For example, the uptake of the administered radiolabeled antibody conjugate (e.g., radiolabeled anti-CD8 antibody conjugate) may be measured at day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with the PD-1/PD-L1 signaling axis (e.g., an anti-PD-1 antibody). The difference between the value of the uptake at a particular time point following initiation of treatment and the value of the uptake at baseline is used to establish whether anti-tumor therapy is efficacious (tumor regression or progression).

In certain embodiments, the radiolabeled antibody conjugate is administered intravenously or subcutaneously to the subject. In certain embodiments, the radiolabeled antibody conjugate is administered intra-tumorally. Upon administration, the radiolabeled antibody conjugate is localized in the tumor. The localized radiolabeled antibody conjugate is imaged by PET imaging and the uptake of the radiolabeled antibody conjugate by the tumor is measured by methods known in the art. In certain embodiments, the imaging is carried out 1, 2, 3, 4, 5, 6 or 7 days after administration of the radiolabeled conjugate. In certain embodiments, the imaging is carried out on the same day upon administration of the radiolabeled antibody conjugate.

In certain embodiments, the radiolabeled anti-CD8 conjugate can be administered at a dose of about 0.1 mg/kg of body weight to about 100 mg/kg of body weight of the subject, for example, about 0.1 mg/kg to about 50 mg/kg, or about 0.5 mg/kg to about 25 mg/kg, or about 0.1 mg/kg to about 1.0 mg/kg of body weight.

In certain embodiments, the antibody or antigen-binding fragment thereof binds specifically to CD8. In certain embodiments, the anti-CD8 antibody comprises the CDRs of a HCVR, wherein the HCVR has an amino acid sequence of SEQ ID NO: 2 and the CDRs of a LCVR, wherein the LCVR has an amino acid sequence of SEQ ID NO: 10.

V. Diagnostic Uses of the Antibodies

The anti-CD8 antibody of the present disclosure may also be used to detect and/or measure CD8, or CD8-expressing cells in a sample, e.g., for diagnostic purposes. For example, an anti-CD8 antibody, or fragment thereof, may be used to diagnose a condition or disease characterized by aberrant expression (e.g., over-expression, under-expression, lack of expression, etc.) of CD8. Exemplary diagnostic assays for CD8 may comprise, e.g., contacting a sample, obtained from a subject, with an anti-CD8 antibody, wherein the antibody is labeled with a detectable label or reporter molecule. Alternatively, an unlabeled anti-CD8 antibody can be used in diagnostic applications in combination with a secondary antibody which is itself detectably labeled. The detectable label or reporter molecule can be a radioisotope, such as $^3$H, $^{14}$C $^{32}$P, $^{35}$S, or $^{125}$I; a fluorescent or chemiluminescent moiety such as fluorescein, or rhodamine; or an enzyme such as alkaline phosphatase, beta-galactosidase, horseradish peroxidase, or luciferase. Specific exemplary assays that can be used to detect or measure CD8 in a sample include enzyme-linked immunosorbent assay (ELISA), radioimmunoassay (RIA), immuno-PET (e.g., $^{89}$Zr, $^{64}$Cu, etc.), and fluorescence-activated cell sorting (FACS).

Samples that can be used in CD8 diagnostic assays according to the present disclosure include any tissue or fluid sample obtainable from a subject. Generally, levels of CD8 in a particular sample obtained from a healthy subject (e.g., a subject not afflicted with a disease or condition associated with abnormal CD8 levels or activity) will be measured to initially establish a baseline, or standard, level of CD8. This baseline level of CD8 can then be compared against the levels of CD8 measured in samples obtained from individuals suspected of having a CD8-related disease or condition.

In some embodiments, an anti-CD8 antibody is labeled with a radioisotope, a fluorescent moiety, a chemiluminescent moiety, or an enzyme. The radioisotope can be selected from the group consisting of $^3$H, $^{14}$C $^{32}$P, $^{35}$S, or $^{125}$I. The fluorescent or chemiluminescent moiety can be selected from the group consisting of fluorescein or rhodamine. The enzyme can be selected from the group consisting of alkaline phosphatase, beta-galactosidase, horseradish peroxidase, or luciferase.

In some embodiments, an assay comprises an anti-CD8 antibody described herein detectably labeled with a fluorescent moiety or a chemiluminescent moiety.

In some embodiments, an anti-CD8 antibody is conjugated with a fluorescent dye. In some embodiments, the anti-CD8 antibody is conjugated to a near-infrared (NIR) fluorescent dye. Suitable dyes include those that provide high sensitivity for low expressing targets under the fluorescence molecular tomography application. In some embodiments, the dye is BODIPY-X630/650®, VivoTag®645, Alexa Fluor*647, VivoTag680®, AlexaFluor680®, AlexaFluor750®, IRDye800CW®, DyLight800, CF®660C, CF®660R, CF®790, and CF®800. In some embodiments, the dye is IRDye 800CW. In some embodiments the dye is Vivotag680XL. In some embodiments, the dye is IRDye 800CW and the DAR is 0.10-1.00. In some embodiments, the dye is Vivotag680XL and the DAR is 1-2. In some embodiments, the dye is IRDye 800CW or Vivotag680XL, and the monomeric purity is >90, 95, 96, or 97% as determined by SE-HPLC based on methods described in Example 13.

Provided herein are also compounds having the following formula: Ab-[D]$_n$, wherein Ab is an anti-CD8 antibody described herein or antigen-binding fragment thereof and D is a fluorescent dye, and n is an integer from 1-4. In some embodiments, n is 1-2. In some embodiments, n is 1. In some embodiments, D is:

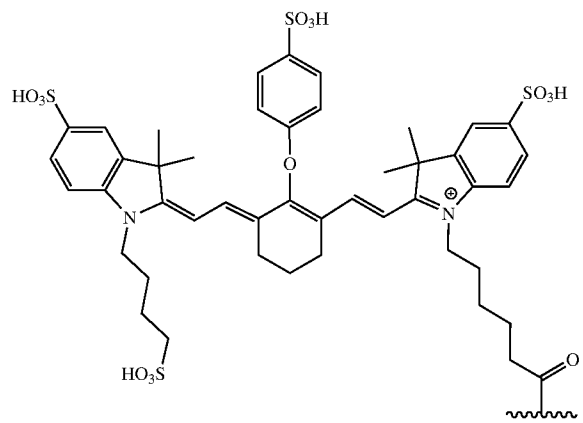 [SMILES: *C(=O)CCCCC[N+]1=C(/C=C/C2=C(Oc3ccc(S(=O)(=O)O)cc3)C(=C/C=C3/N(CCCCS(=O)(=O)O)c4ccc(S(=O)(=O)O)cc4C3(C)C)/CCC2)C(C)(C)c2cc(S(=O)(=O)O)ccc21]

or a pharmaceutically acceptable salt thereof.

VI. EXAMPLES

Certain embodiments of the disclosure are illustrated by the following non-limiting examples.

Example 1: Generation of Human Antibodies to CD8

An immunogen comprising CD8α DNA and/or CD8β DNA can be used to generate antibodies to CD8. Likewise, an immunogen comprising CD8α protein and/or CD8β protein can be used to generate antibodies to CD8. In certain embodiments, the antibodies are obtained from mice immunized with full length CD8α DNA (for example, SEQ ID NO: 17) and/or CD8β DNA (for example, SEQ ID NO: 19), full length CD8α protein (for example, SEQ ID NO: 18) and/or CD8β protein (for example, SEQ ID NO: 20), or a fragment of CD8α protein and/or CD8β protein. In some embodiments, the antibodies are obtained from mice immunized with a fusion peptide containing full length CD8α and CD8β, or a fusion peptide containing fragments of both CD8α and CD8β.

An exemplary anti-CD8 antibody was obtained by injecting a VELOCIMMUNE® mouse (i.e., an engineered mouse comprising DNA encoding human immunoglobulin heavy and kappa light chain variable regions) with full length CD8α DNA (SEQ ID NO: 17) and full length CD8β DNA (SEQ ID NO: 19). The DNA sequences cause expression of the CD8 protein in the mouse, and may produce more structurally accurate protein targets in vivo to which antibodies are generated. The antibody immune response was monitored by a CD8-specific immunoassay. When a desired immune response was achieved splenocytes were harvested and fused with mouse myeloma cells to preserve their viability and form hybridoma cell lines. The hybridoma cell lines were screened and selected to identify cell lines that produce CD8-specific antibodies. Using this technique, an anti-CD8 chimeric antibody (i.e., an antibody possessing human variable domains and mouse constant domains) was obtained. A fully human version of the antibody can be made by replacing the mouse constant region with the human constant region. The variable region nucleic acid and amino acid sequences of the exemplary antibody are provided in Table 1 above. The exemplary anti-CD8 antibody generated according to the methods described above is the antibody designated "mAb1".

The biological properties of the exemplary antibodies generated in accordance with the methods of this Example are described in detail in the Examples set forth below.

Example 2: Antibody Binding to CD8 as Determined by Surface Plasmon Resonance Equilibrium dissociation constants ($K_D$ values) for hCD8α-mmh binding to purified anti-CD8 mAbs were determined using a real-time surface plasmon resonance biosensor using a Sierra Sensors MASS-1 high-capacity amine sensor surface was derivatized by amine coupling with a polyclonal goat anti-mouse Fc antibody (GE, #BR-1008-38) to capture purified anti-CD8 mAbs. SPR binding studies were performed in a buffer composed of 0.01M HEPES pH 7.4, 0.15M NaCl, 3 mM EDTA, 0.05% v/v Surfactant P20 (HBS-ET running buffer). Different concentrations of hCD8α with a C-terminal myc-myc-polyhistidine tag (hCD8α-mmh, REGN3940) prepared in HBS-ET running buffer (ranging from 300 nM to 3.7 nM, 3-fold dilutions) were injected over the anti-CD8 mAb captured surface at a flow rate of 50 μL/minute. Association of hCD8α-mmh to the captured monoclonal antibody was monitored for 4 minutes and the dissociation of hCD8α-mmh in HBS-ET running buffer was monitored for 10 minutes. All of the binding kinetics experiments were performed at 25° C. Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D = \frac{kd}{ka}, \text{ and } t^{1/2} = \frac{\ln(2)}{kd}$$

Binding kinetic parameters for hCD8α-mmh binding to purified anti-CD8 monoclonal antibody at 25° C. are shown in Table 2.

TABLE 2

| | Antibody Binding Characteristics | | | |
|---|---|---|---|---|
| REGN #/Ab PID # | $k_a$ (1/Ms) | $k_d$ (1/s) | $K_D$ (M) | $t_{1/2}$ (min) |
| H2aM25428N | 1.59E+05 | 5.19E−03 | 3.26E−08 | 2.2 |

Example 3: Cell Binding by FACS Analysis

Flow Cytometry was performed in order to evaluate the binding of CD8 antibodies or isotype control antibodies to primary human CD8 positive T cells and cynomolgus monkey T cells.

Characterization of CD8 Antibody Binding to Human and Monkey T Cells:

PBMCs were isolated from human leukocyte packs or cynomolgus monkey whole blood. Subsequently CD8 positive T cells were isolated from human PBMCs and from cynomolgus monkey PBMCs, T cells that were either CD4 and CD8 positive were isolated.

a) Isolation of Human CD8 Positive T Cells from Human Leukocyte Packs:

Human CD8 positive T cells were isolated from a leuko-pak of peripheral blood from one healthy donor for testing binding of mAb1. Human leukocyte packs were obtained from NY Blood Center. PBMC isolation was accomplished by density gradient centrifugation using 50 ml SepMate™ tubes and following the manufacturers recommended protocol. Briefly, 15 ml of Ficoll-Paque PLUS was layered into 50 ml SepMate™ tubes, followed by addition of 30 ml of leukocytes diluted 1:2 with PBS. Subsequent steps were followed according to SepMate's™ manufacturer protocol. Following PBMC isolation, CD8 positive T cells were enriched using human CD8 Microbead kits from Miltenyi Biotec following the manufacturer's protocol. CD8 positive T cells were expanded by incubating cells with Human T-Activator CD3/CD28 Dynabeads® in human primary culture medium (X-Vivo 15 medium supplemented with 10% fetal bovine serum and 0.01 mM beta-mercaptoethanol). Recombinant human IL-2 (501 U/ml) was supplemented into culture media 72 hours post CD3/CD28 Dynabead incubation. When cells had expanded to the necessary cell number for flow cytometry analysis, the Dynabeads were removed by magnetic separation and cells were immediately used to determine the binding of CD8 antibodies or isotype controls.

b) Cynomolgus Monkey T Cell Isolation

Cynomolgus whole blood from BioreclamationIVT was used for isolating monkey T cells for antibody binding analysis. PBMC's were isolated using SepMate™ 15 tubes and density gradient centrifugation following the manufacturer's protocol. Subsequently, T cells were enriched using the Pan T-isolation Kit for non-human primates (Miltenyi Biotech) following the manufacturers recommended protocol. Enriched T cells were then activated and expanded using the T cell Activation/Expansion kit (Miltenyi Biotech) for non-human primates in monkey primary culture medium (X-Vivo 15 medium supplemented with 10% fetal bovine serum and 0.01 mM beta-mercaptoethanol). After 72 hours recombinant human IL-2 (100 IU/ml) was supplemented into the primary culture media and T cells were expanded for one week. Magnetic beads used for T cell activation and expansion were magnetically removed immediately prior to staining cells with CD8 or isotype control antibodies.

c) Flow Cytometry Analysis of mAb1 Antibody Binding to Human CD8 Positive and Cynomolgus Monkey T Cells.

mAb1 and isotype control antibodies were 4 fold serially diluted in stain buffer (PBS containing 2% FBS) in either an 8-point titration for human CD8 positive T cells or 11 point titration for cynomolgus monkey T cells, starting at a concentration of 200 nM. A sample without primary antibody, stain buffer only, was also included as a control. Antibody titrations were plated out, 50 ul/well, into V-bottom microplates. Primary human and cynomolgus monkey T cells were stained for 15 minutes with LIVE/DEAD™ Fixable Violet Dead Cell Stain (Invitrogen) diluted 1:1000 in PBS. Cells were washed twice, and resuspended in PBS containing 2% FBS. To gate out CD4+ monkey T cells a CD4 antibody from BD Biosciences, that reacts with cynomolgus CD4+ T cells, was incubated with monkey T cells for 30 min on ice and cells were subsequently washed once with stain buffer. Human CD8 positive and monkey T cells in stain buffer were plated such that 50 ul of cell suspension, containing approximately 150,000 T cells, were added into wells of the 96-well V-bottom microplate containing the titrated antibodies. Antibodies were therefore diluted 2 fold, accordingly final concentrations ranged from 100 nM to 24 pM for antibodies incubated with human CD8 positive T cells or 100 nM to 0.10 pM for antibodies incubated with monkey T cells. Cells were incubated with primary antibody for 30 minutes on ice, washed twice with staining buffer (PBS supplemented with 2% FBS) and secondary allophycocyanin (APC) goat anti-mouse IgG antibody was added to all wells at a concentration of 2 µg/mL and incubated on ice for 30 minutes. Samples were then washed once with stain buffer and subsequently fixed in BD Cytofix diluted with staining buffer 1:1. After removal of the fixation buffer, cells were resuspended in staining buffer and filtered prior to analysis on the Beckman Coulter Cytoflex flow cytometry instrument. Samples were analyzed with the FlowJo10 software such that only viable, CD8 positive, single cells were evaluated for antibody binding. Geometric MFI of APC was determined and plotted against antibody concentrations and EC50 values were determined based on 8 data points for human CD8 positive T cells or 12 points for monkey T cells, starting with 100 nM using a four-parameter logistic equation in GraphPad Prism™.

Results:

Flow Cytometry Analysis of mAb1 Antibody Binding to Human CD8 Positive and Cynomolgus Monkey T Cells.

The ability of mAb1 to bind human and monkey CD8 was assessed by flow cytometry (FIG. 1). An irrelevant isotype matched antibody was used as a negative control in these experiments. Dose-dependent binding of mAb1 was observed on both human and monkey CD8 positive T cells. mAb1 displayed an EC50 value of 0.37 nM for human CD8 positive T cells with an approximate 2,778-fold increase in MFI compared to isotype control antibody at 25 nM. mAb1 bound cynomolgus monkey T cells with an EC50 value of 0.33 nM and an approximate 1,475-fold increase in MFI compared to the isotype control at 25 nM. See Table 3. The isotype control did not demonstrate dose-dependent binding to either human or monkey T cells. These results indicate that mAb1 cross-reacts with human and monkey CD8 and binds CD8 of both species with similar EC50 values.

$$\text{Fold change} = \frac{\text{Geometric } MFI \text{ at 25 nM } mAB1}{\text{Geometric } MFI \text{ at 25 nM Isotype}}$$

TABLE 3

Flow cytometry analysis of mAb1 binding to human CD8 positive T cells and cynomolgus monkey T cells.

| | mAb1 cell binding | |
|---|---|---|
| | Human | Monkey |
| EC50 [nM] | 0.37 | 0.33 |
| Fold Change | 2778 | 1475 |

Example 4: Altered IFNγ Production by Activated T Cells in the Presence of mAb1

T cells are activated when their T cell receptor (TCR) specifically recognizes foreign antigen presented by MHC molecules on target cells. This interaction can be strengthened by the presence of co-receptors, such as CD4 and CD8, on T cells that bind non-variable regions of MHCII or MHCI, respectively, on the interacting target cells. Additionally, these co-receptors have a direct role in modulating T cell activity through the association of their cytoplasmic domain with the tyrosine protein kinase Lck. Interfering with the interaction between co-receptors and MHC molecules could impact T cell activity. In order to discern whether CD8 specific antibodies alter T cell activity a mixed lymphocyte reaction (MLR) assay was employed. An MLR assay is an in-vitro, physiologically relevant means of activating T cells. In a one-way MLR, leukocytes from one individual are co-cultured with proliferation-arrested leukocytes of another, genetically distinct, individual. Incompatibility of allogeneic determinants leads to T cell activation, which can be evaluated by cytokine production and/or proliferation. Cytokines IFNγ and IL-2, as well as proliferation, are commonly used as readouts for CD4+ T cell activity. However, it has been observed that CD8 positive effector T cell activity is reflected best by their production of IFNγ, while IL-2 and proliferation may be the result of bystander effects and are not directly related to the proportion of activated CD8 positive T cells (Anthony et al. 2012—Dissecting the T Cell Response: Proliferation Assays vs. Cytokine Signatures by ELISPOT—Cells, 1, 127-140).

Human CD8 Positive T Cell MLR Assay:

PBMCs were isolated from human leukocyte packs and subsequently processed by negative isolation to obtain untouched CD8 positive T cells. A one-way MLR assay was performed using CD8 positive T cells to evaluate whether mAb1 impacts T cell activity, indicated by IFNγ production.

Isolation of PBMCs and Human CD8 Positive T Cells from Human Leukocyte Packs:

Human PBMC's were isolated from four leukopaks of peripheral blood from healthy donors obtained from NY Blood Center. PBMC isolation was accomplished by density gradient centrifugation using 50 ml SepMate™ tubes and following the manufacturers recommended protocol. Briefly, 15 ml of Ficoll-Paque PLUS was layered into 50 ml SepMate™ tubes, followed by addition of 30 ml of leukocytes diluted 1:2 with PBS. Subsequent steps were followed according to SepMate's™ manufacturer protocol. A fraction of the isolated PBMC's (>300×10^6) were frozen down in FBS containing 10% DMSO at a concentration of 50 million cells per vial. With the remainder of PBMCs, CD8 positive T cells were enriched using human CD8 T Cell Isolation kits from Miltenyi Biotec following the manufacturer's protocol. Isolated CD8 positive T cells were subsequently frozen down in FBS containing 10% DMSO at a concentration of 50 million cells per vial. PBMCs and CD8 positive T cells were thawed the day of the MLR assay set-up in primary culture medium (X-Vivo 15 medium supplemented with 10% fetal bovine serum and 0.01 mM beta-mercaptoethanol) containing Benzonase Nuclease, at a concentration of 50 million cells per 10 ml of primary culture media containing 500 U of Benzonase Nuclease.

MLR Assay Set-Up

Primary cell culture media (125 ul/well) was plated into each well of a round bottom microtiter plate. A three point, 10 fold, serial dilution of mAb1 and isotype control antibody was performed in primary culture media starting at a concentration of 400 nM. From this 25 ul of antibody was plated out in triplicate into wells of round bottom microplates. The antibody was $\frac{1}{8}^{th}$ the total volume in each well making the final antibody concentrations 50 nM, 5 nM, and 0.5 nM. Wells without antibody, primary culture media only, were also included as controls. Negatively isolated CD8 positive T cells from 3 donors and PBMC's from these same 3 donors, as well as an additional donor were used in the MLR assay. PBMC's were treated with mitomycin C diluted to 50 ug/mL in primary stimulation media at a concentration of $12\times10 \neq cells/ml$. After incubation at 37° C./5% $CO_2$ for 1 hour PBMC's were collected into 50 ml conical tubes and washed a total of 3 times with primary cell culture media. These cells were resuspended to a final concentration of $12\times10^{\wedge}6$ cell/ml in primary culture media and 25 ul was added to wells of the round bottom microtiter plate, leading to a final concentration of 300,000 PBMC's per well. Additionally, wells without PBMCs, media and T cells only, were also included as a control to determine whether T cells alone could produce IFNγ. T cells were prepared at a concentration of $7\times10^{\wedge}6$ cells/ml in primary culture media and 25 ul was plated out into wells of the round bottom microtiter plate, thus the final concentration of T cells in each well was 175,000. Wells without T cells, media only, were also included to serve as controls to verify PBMC's alone were not contributing to IFNγ production. Only one donor's T cells and one donor's mitomycin C treated PBMCs were included per well. Each of the three donor T cells were paired with its own or a different donors PBMCs. After 72 hour incubation at 37° C./5% $CO_2$, microtiter plates were centrifuged to pellet the cells and 20 ul of media supernatant was collected. From the collected supernatant 5 ul was tested in a human IFNγ alphalisa assay according to the manufacturer's protocol. The measurements were acquired on the multilabel plate reader Envision (PerkinElmer). Raw RLU values were plotted in bar graphs in GraphPad Prism™ and the amount of IFNγ production in wells containing antibody was compared to wells containing PBMCs and T cells only, and calculated as percent inhibition of IFNγ production.

Figure 2:
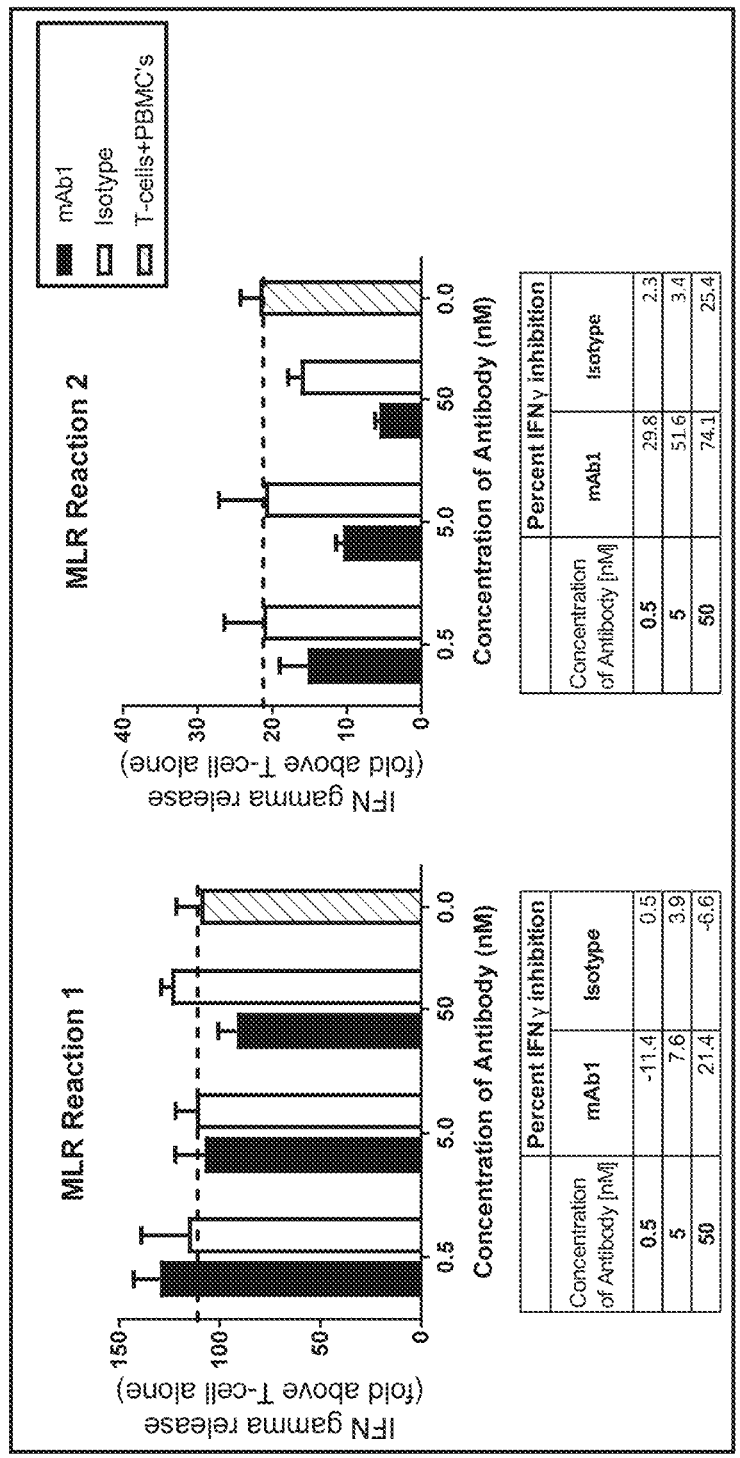
FIG. 2 depicts modulation of human CD8 T cell activity through inhibition of IFNγ production by mAb1.

Results:

The ability of mAb1 to impact CD8 T cell activity was measured by IFNγ production in a one-way MLR (FIG. 2). An irrelevant isotype matched antibody, was used as a control in these experiments. Results and representative images below, for two different T cell/PBMC pairs, indicate that mAb1 is able to dose dependently decrease IFNγ production. The extent of this inhibition appears to be donor dependent as one donor/PBMC pair (MLR reaction 1) exhibits <10% inhibition of IFNγ at 5 nM mAb1 treatment, while another donor/PBMC pair (MLR reaction 2) exhibits >50% inhibition of IFNγ. In both reactions the isotype control had minimal impact at 5 nM on IFNγ production. See Table 4.

Calculation for% $IFN_\gamma$ Inhibition:

$$IFN_\gamma \text{ Inhibition} = \left(1 - \frac{RLU \text{ Signal of } PBMC/T\text{-cell mix incubated with 5 nM antibody}}{RLU \text{ Signal of } PBMC/T \text{ cell mix with no antibody}}\right) \times 100$$

TABLE 4

| | Percent Inhibition of IFNγ Production | | | |
|---|---|---|---|---|
| Antibody | MLR Reaction 1 | | MLR Reaction 2 | |
| Concentration | mAb1 | Isotype | mAb1 | Isotype |
| 0.5 nM | −11.4 | 0.5 | 29.8 | 2.3 |
| 5 nM | 7.6 | 3.9 | 51.6 | 3.4 |
| 50 nM | 21.4 | −6.6 | 74.1 | 25.4 |

Example 5: Altered T Cell Activity in the Presence of mAb1

T cells are activated when their T cell receptor (TCR) specifically recognizes foreign antigen presented by Major Histocompatibility Complex (MHC) molecules also known as Human Leukocyte Antigens (HLA) on antigen-presenting cells (APC). This interaction can be strengthened by the presence of co-receptors, such as CD4 and CD8, on T cells that bind non-variable regions of MHCII or MHCI, respectively, on the interacting APC. Additionally, these co-receptors have a direct role in modulating T cell activity through the association of their cytoplasmic domain with the tyrosine protein kinase Lck (Goldrath et al., Selecting and maintaining a diverse T cell repertoire, Nature 402: 255-262, 1999; Denkberg et al. Critical Role for CD8 in Binding of MHC Tetramers to TCR: CD8 Antibodies Block Specific Binding of Human Tumor-Specific MHC-Peptide Tetramers to TCR, The Journal of Immunology, 2001, 167: 270-276; Cantrell et al., T cell Antigen Receptor Signal Transduction, Immunology, 2002, 105.4: 369-374; and Wang et al. 2009).

The CD8 molecule exists as a homodimer (CD8αα) or heterodimer (CD8αβ) on the surface of subsets of cells of the immune system. In TCRαβ T cells, the CD8αβ heteromeric form is expressed. Interfering with the interaction between co-receptors and MHC molecules could impact T cell activity.

In order to discern whether CD8 specific antibodies alter T cell activity, a T cell/APC based bioassay was employed.

Reporter T Cell Engineering:

TCR signaling events can be monitored by reporter genes, driven by various transcription factors such as activator-protein 1 (AP-1), Nuclear Factor of Activated T cells (NFAT) or Nuclear factor kappa-light-chain-enhancer of activated B cells (NFκB) (Shapiro et al., Cutting Edge: Nuclear Factor of Activated T Cells and AP-1 Are Insufficient for IL-2 Promoter Activation: Requirement for CD28 Up-Regulation of RE/AP, The Journal of Immunology, 1998, 161 (12): 6455-6458).

The human T cell clone, JRT3.T3.5 was engineered to express the reporter gene, firefly luciferase, under the control of the transcription factor AP-1. Antibiotic resistant cells were further manipulated by transduction with human CD28, (NP_006130.1), 1G4 TCR alpha and beta subunit (Chen et al. 2000) and human CD8 alpha and beta subunit (alpha accession #NP_001759.3 and beta accession #NP_004922.1). A single clone was generated (JRT3.T3/AP1-Luc/CD28/CD8AB/1G4AB clone 18) and used in T cell/APC reporter bioassay experiments. The established T cell reporter line was maintained in RPMI +10% FBS+ penicillin/streptomycin/glutamine (P/S/G) supplemented with 100 ug/mL hygromycin+500 ug/mL G418+1 ug/mL puromycin.

Apc Engineering:

The mouse fibroblast 3T3 cell line was engineered to stably over-express the HLA-A*02 allele (accession #P01892-1) and human P2-microglobulin (hβ2M; accession #NP_004039.1) along with NY-ESO-1 157-165, an HLA-A2*02-restricted peptide derived from cancer-testis antigen NY-ESO-1 (accession #NP_001318.1).

The established APC line was maintained in DME+10% BCS+P/S/G supplemented with 100 ug/mL hygromycin+ 500 ug/mL G418+1 ug/mL puromycin.

T Cell/APC Stimulation:

In the developed bioassay HLA-A2/NYESO1(157-165) MHCI/peptide complex on engineered APC binds and stimulates the 1G4 TCR (Robbins et al., Single and Dual Amino Acid Substitutions in TCR CDRs Can Enhance Antigen-Specific T Cell Functions, J. Immunol. 2008; 180 (9): 6116-6131) and leads to increased transcriptional activity of AP-1 in the engineered reporter T cell line. AP-1 in turn activates the transcription of the luciferase reporter gene, which is used as the as the readout of the assay. In this bioassay, CD8 monoclonal antibodies were tested to assess their blocking activity.

Luciferase Assay Set Up:

RPMI1640 supplemented with 10% FBS and P/S/G was used as assay medium to prepare cell suspensions and antibody dilutions to carry out the screening of anti-CD8 antibodies on the day of the experiment.

A day before the experiment, engineered reporter T cells were cultured in selection media at 5×10^5 cells/mL. A 10-point 1:3 serial dilution of anti-CD8 monoclonal antibodies and isotype matched negative controls was prepared. The dilution of the monoclonal antibodies ranged between 15 pM to 100 nM. The last dilution point did not contain an antibody. Overnight cultured reporter T cells and APC cells were re-suspended in assay media at 2×10^6/mL and 4×10^5/mL, respectively. Reagents were added in following order to 96 well white flat bottom plates: serial dilutions of monoclonal antibodies were pipetted to corresponding wells, followed by 1×10^4 cells/well APC cells. Plates were incubated for 15-30 minutes at room temperature. Then 5×10^4 reporter T cells were added on top of the APC and samples were incubated for another 4-6 hours at 37° C./5% CO₂, before the addition of 100 uL ONE-Glo™ (Promega) reagent to detect the AP1-Luc activity. The emitted light was captured in relative light units (RLU) on the multilabel plate reader Envision (PerkinElmer). All serial dilutions were tested in duplicates.

The $EC_{50}$ values of the CD8 monoclonal antibodies were determined from a four-parameter logistic equation over a 10-point dose-response curve using GraphPad Prism software. Percent reduction of T cell response in the bioassay was calculated as shown below:

% Reduction=100%−[Mean RLU mAb at 100 nM×100/Mean RLU at 0 nM]

Figure 3:
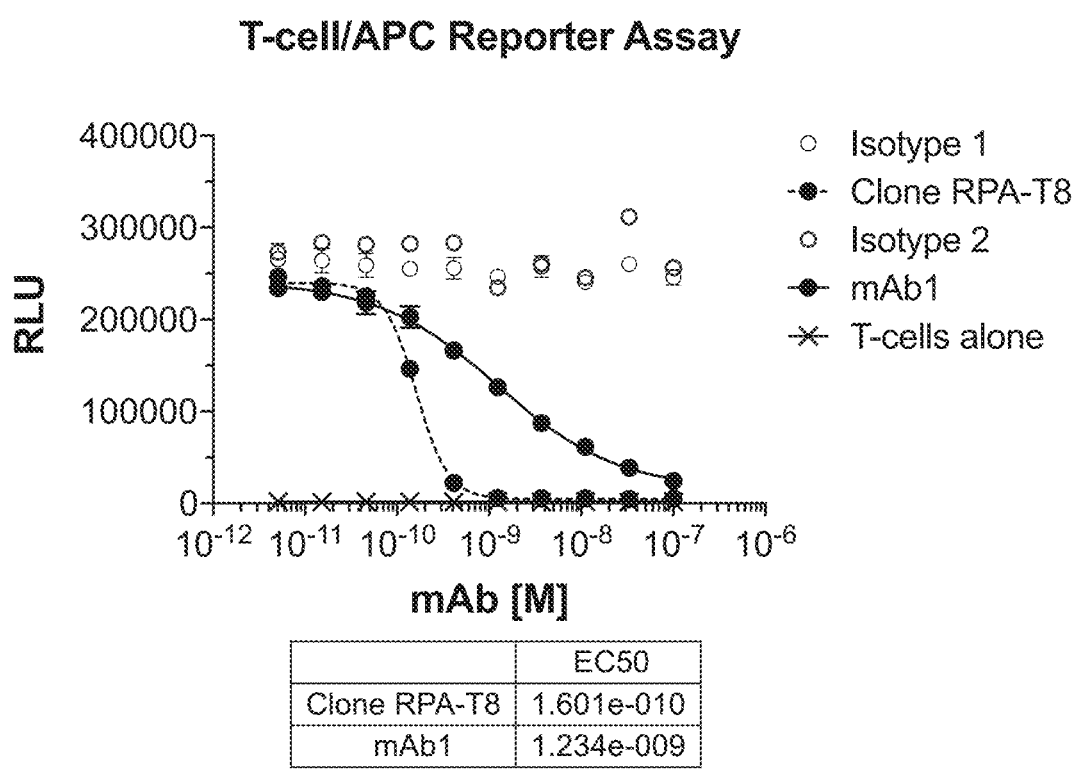
FIG. 3 depicts data from a CD8 T cell/APC luciferase assay demonstrating mAb1 inhibition of CD8 transcription activity.

Results:

Table 5 and FIG. 3 show that mAb1 and the commercially available Clone RPA-T8, reduce luciferase activity in engineered T cells with an $IC_{50}$ of 1.2 nM and 161 pM, respectively. Isotype 1 and Isotype 2 do not show a dose-dependent inhibition as expected. At 100 nM mAb1 reduces the T cell activity around 89.7%, whereas Clone RPA-T8 blocks 97.9%. Compared to Clone RPA-T8, mAb1 blocks weaker CD8/MHCI interaction. Both antibodies were shown to bind to human CD8α subunit in Biacore and ELISA experiments.

TABLE 5

IC$_{50}$ and % Inhibition of T cell response by CD8 monoclonal antibodies in CD8 T cell/APC luciferase assay

| Antibody | IC$_{50}$ [M] | Reduction of T cell response at 100 nM [%] |
|---|---|---|
| Isotype 1 | — | 7.4 |
| Isotype 2 | — | 6.2 |
| Clone RPA-T8 | 1.61E−10 | 97.9 |
| mAb1 | 1.2E−09 | 89.7 |

Example 6: LC-MS Quantitation of CD8 in Raji/PBMC Xenografts and Clinical Samples Frozen tissue samples (Raji/PBMC tumors, mouse spleens, and melanoma tissue) were lysed in 1× RIPA lysis buffer with protease inhibitors (Thermo Fisher Scientific). Tissues were cut into small pieces and were homogenized with 1 mL lysis buffer in a tight fitting dounce homogenizer. The lysate was incubated on ice for 30 mins with sonication for 30 secs every 10 mins to achieve complete protein extraction. The lysate was centrifuged at 14,000 g for 10 mins. Protein concentration was measured by BCA assay. Each sample was diluted into 1 mg/mL, centrifuged at 14,000 g for 10 mins and stored in aliquots at −80° C.

One hundred μL of Biotinylated anti-CD8α binding protein (2 μg/mL) was added to each well of a streptavidin coated 96 well plate (Thermo Fisher Scientific). The plate was then incubated at room temperature for 2 hours followed by being washed for 3 times with PBST (pH7.4, 0.05% Tween-20). Mouse spleen lysate was used as the surrogate matrices to generate the standard curve for CD8 quantitation. Recombinant CD8α·mmh was spiked into each of 100 μg of mouse spleen lysate at a final concentration ranging from 0.39 to 100 ng/mg protein (1:2 serial dilution). A hundred L of tested sample was applied to each well and was incubated at R.T. for 2 hours. Each well was then washed with 200 μL of PBST for 3 times and with 200 μL of ddH$_2$O for once. The captured CD8 was eluted with 100 μL of elution buffer (3% formic acid in 50% ACN) and was completely dried after transferring into a new 96 well plate.

Each sample was denatured in 10 μL of 8M Urea/TCEP buffer at 37° C. for 1 hr. A signature peptide (AAE-GLDTQR) from CD8α was selectively monitored and the corresponding heavy isotope labeled peptide (same AA sequence with Arg-$^{13}C_6^{15}N_4$/Lys-$^{13}C_6^{15}N_2$) was spiked into each sample as an internal standard. The standards and test samples were alkylated with 5 μM of IAA at R.T. for 30 min and digested by lys-C (1:100 w/w) for 4 hours then by trypsin (1:20 w/w) overnight at 37° C. The digestion was quenched by adding 10% formic acid to each sample.

Each processed sample (15 μL) was injected onto a pre-equilibrated nano C18 trap column and the peptides were separated by an easy nano C18 separation column followed by parallel reaction monitoring (PRM) analysis using a Q Exactive plus mass spectrometer. The calibration curve of each protein was established by plotting the L/H peak area ratio against concentration of the spike-in peptide. The abundance of the endogenous CD8α in each tissue sample was calculated based on the calibration curves. The lowest concentration of CD8α·mmh reference standard (equivalent to 0.96 ng/mg of endogenous CD8α) was within the dynamic range of the assay and was defined as the assay's LLOQ (lower limit of quantitation).

Results:

CD8α expression was analyzed in 5 of tumors and spleens from PBMC/Raji implanted mice, 2 tumors and spleens of Raji only implanted mice, 10 melanoma clinical samples and 5 melanoma normal adjacent tissues (NAT). The tissue weights, protein amounts, extraction yield and CD8 expression were listed in Table 6. Bmax was calculated based on the following equation with an estimation of tumor density at 1 g/mL.

$$Bmax\ (nM) = \frac{CD8\ (\text{ng/mg protein}) \times \text{Total Protein Amount (mg)} \times 10E6}{2.57^* \ 10E4 \times \text{Tumor Weight (mg)}}$$

TABLE 6

Tissue Weights, Protein Amounts, Extraction Yield and CD8 Expression

| Tissue Type | Sample | Tumor weight (mg) | Protein (mg) | Protein yield (%) | CD8α (ng/mg protein) | CD8_Bmax (nM) |
|---|---|---|---|---|---|---|
| Melanoma | 131778T2(5) | 250 | 24.1 | 9.6 | 29.4 | 55.2 |
| Melanoma | 13841T2(1) | 220 | 20.1 | 9.1 | 37.2 | 66.1 |
| Melanoma | 13765T2(2) | 250 | 19.4 | 7.8 | 4.5 | 6.8 |
| Melanoma | 13524T2(7) | 200 | 13.0 | 6.5 | 36.9 | 46.6 |
| Melanoma | 13547T2(1) | 220 | 16.1 | 7.3 | 32.9 | 46.8 |
| Melanoma | 131086T6(1) | 180 | 9.3 | 5.2 | 11.1 | 11.2 |
| Melanoma | 131719T2(3) | 230 | 17.6 | 7.7 | 9.3 | 13.9 |
| Melanoma | 131291T2(1) | 240 | 17.4 | 7.3 | 30.5 | 43.1 |
| Melanoma | 131815T2(3) | 290 | 9.1 | 3.1 | 29.0 | 17.7 |
| Melanoma | 131778T2(5) | 180 | 9.2 | 5.1 | 2.5 | 2.5 |
| NAT | 131291T1(1) | 270 | 8.9 | 3.3 | 1.6 | 1.1 |
| NAT | 131086T1(1) | 280 | 5.9 | 2.1 | 1.5 | 0.6 |
| NAT | 131719T1(2) | 250 | 4.1 | 1.6 | 2.3 | 0.7 |
| NAT | 13841T1(1) | 250 | 6.6 | 2.6 | 1.9 | 1.0 |
| NAT | 13788T1(2) | 170 | 10.9 | 6.4 | 1.9 | 2.4 |
| Raji only Tumor | M6T | 140 | 7.2 | 5.2 | 0.1 | 0.1 |
| Raji only Tumor | M7T | 290 | 13.1 | 4.5 | 0.1 | 0.1 |
| Raji/PBMC Tumor | M13T | 320 | 12.7 | 4.0 | 15.0 | 11.6 |
| Raji/PBMC Tumor | M14T | 310 | 14.4 | 4.7 | 10.6 | 9.6 |
| Raji/PBMC Tumor | M19T | 370 | 17.0 | 4.6 | 6.1 | 5.5 |
| Raji only Spleen | M6S | 31 | 2.1 | 6.7 | 0.0 | 0.0 |
| Raji only Spleen | M7S | 28 | 2.0 | 7.2 | 0.0 | 0.0 |
| Raji/PBMC Spleen | M13S | 20 | 1.3 | 6.7 | 6.2 | 8.0 |
| Raji/PBMC Spleen | M14S | 16 | 1.3 | 7.9 | 0.6 | 0.9 |

TABLE 6-continued

Tissue Weights, Protein Amounts, Extraction Yield and CD8 Expression

| Tissue Type | Sample | Tumor weight (mg) | Protein (mg) | Protein yield (%) | CD8α (ng/mg protein) | CD8_Bmax (nM) |
|---|---|---|---|---|---|---|
| Raji/PBMC Spleen | M19S | 27 | 1.9 | 7.0 | 1.8 | 2.5 |
| Raji/PBMC Spleen | M21S | 29 | 1.8 | 6.3 | 2.0 | 2.5 |

Example 7: Conjugation of Anti-CD8 Antibody mAb1 with p-SCN-Bn-DFO

To modify the parental anti-CD8 antibody, mAb1 (having an HCVR/LCVR sequence pair of SEQ ID NOs: 2/10), and an isotype control antibody to be suitable for ImmunoPET studies with radiolabeling, a chelator, p-SCN-bn-Deferoxamine (DFO; Macrocylics, Cat #: B-705), was attached to the antibodies.

For the modification, mAb1 was concentrated to approximately 29 mg/mL in in PBS +5% glycerol with a 10K MWCO spin concentrator (Amicon Ultra-15 Centrifugal Filter Unit, EMD Millipore, Cat #: UFC901024). The concentration was determined by a Nanodrop 2000 UV/VIS spectrometer (Thermo Scientific) using the MacVector sequence based extinction coefficient of 212,400 $M^{-1}$ $cm^{-1}$ and molecular weight 145,654 g/mol. Five milligrams of the concentrated antibody was diluted to 10 mg/mL with 100 mM $NaCO_3$, pH 9.0 (final pH was confirmed to be 9.0).

In a separate vial, DFO was prepared in neat dimethyl sulfoxide (DMSO) at a DFO concentration of 50 mM. This DFO solution was added to the antibody solution in ¼ increments such that the final solution makeup was 10 mg/mL mAb1 in conjugation buffer, 2% DMSO with 3-fold mole-to-mole excess of DFO. This solution was allowed to incubate in a 37° C. water bath with no additional stirring. After 30 minutes at 37° C., the solution was promptly passed through a NAP-5 desalting column (GE Healthcare, Cat. #17-0853-02), pre-equilibrated with a buffer containing 10 mM histidine at pH 5.5 (formulation buffer). The final solution was sterile-filtered via a syringe filter (Acrodisc 13 mm syringe filter, Pall Corporation, Cat #: 4602).

Figure 4:
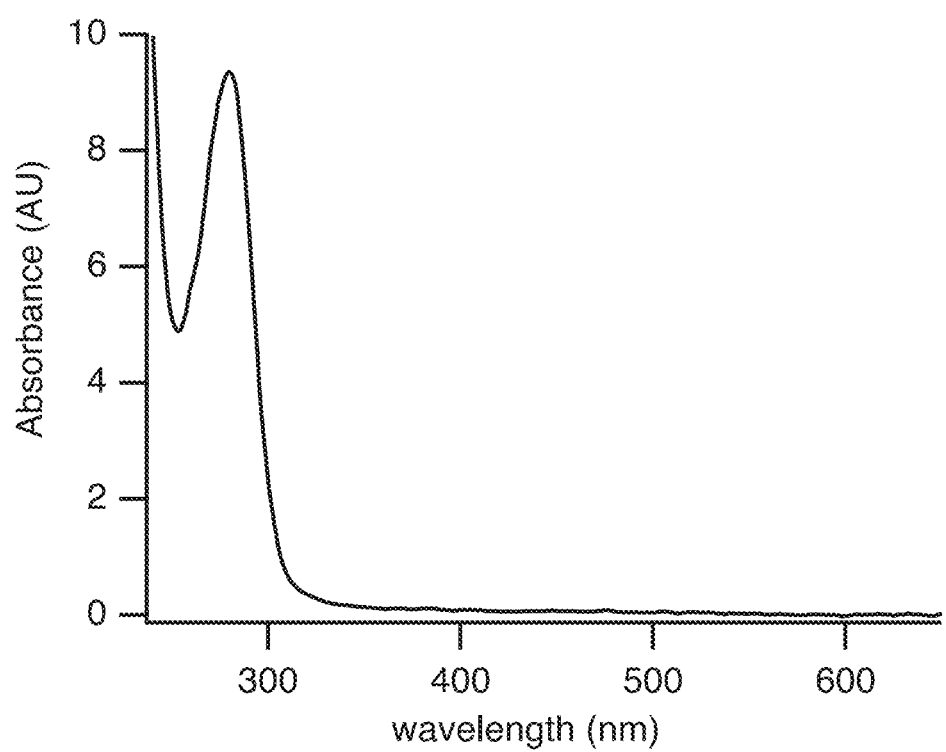
FIG. 4 depicts UV/VIS spectrum of DFO-mAb1 conjugate.

The antibody concentration and DFO-to-Antibody Ratio (chelating moiety-to-antibody ratio) was subsequently measured by UV/VIS spectroscopy. See FIG. 4. For the absorbance measurement, the DFO-conjugated antibody was measured against the formulation buffer at 252 nm (A252), 280 nm (A280) and 600 nm (A600). For the calculation, the background was corrected at each absorbance value using the equation:

$$A'_\lambda = A_\lambda - A_{600}$$

The antibody concentration, conjugate concentration, and chelating moiety-to-antibody ratio were calculated using the equations below:

Antibody Concentration Calculation $$Conc\ mAb\ (\text{mg/mL}) = \frac{A'_{280}}{\epsilon_{280}} * MW$$

Conjugate Concentration Calculation $$Conc\ \text{conjugate}\ (\text{mg/mL}) = \frac{A'_{252} - 1.53 A'_{280}}{\epsilon_{252} - 1.53 \epsilon_{280}} * MW$$

Chelating Moiety-to-Antibody Ratio Calculation $$DAR = \frac{\epsilon_{252} A'_{280} - \epsilon_{280} A'_{252}}{18800 A'_{252} - 28700 A'_{280}}$$

Figure 5:
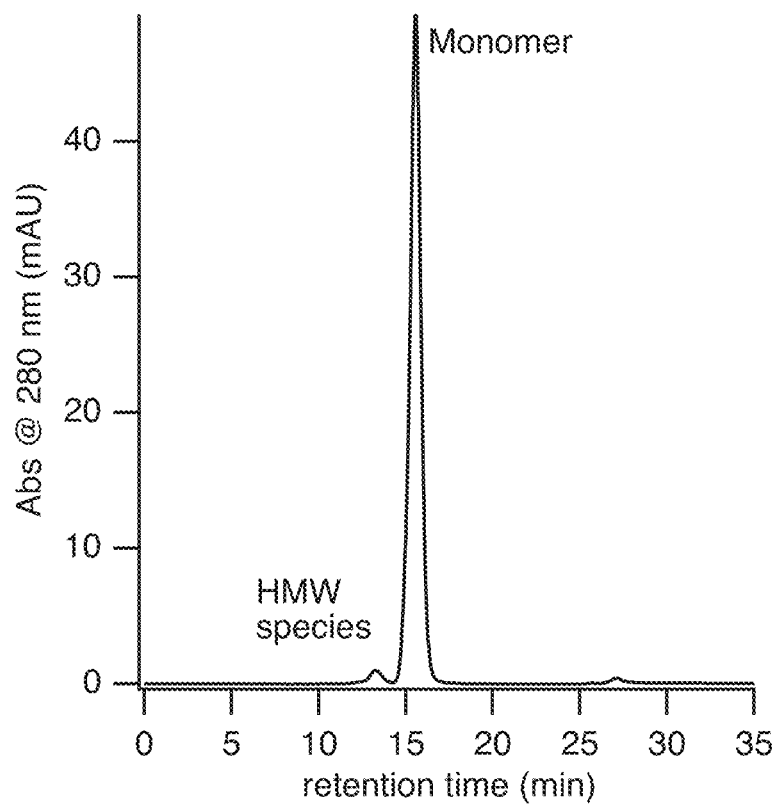
FIG. 5 depicts HPLC-SEC of a 25 ug injection of DFO-mAb1 conjugate on Superdex 200 Increase column with UV 280 nm absorbance detection. Monomeric (97.5%) and high molecular weight (HMW) species (2.5%) are indicated.

The antibody conjugate was tested for aggregation using size-exclusion high performance liquid chromatography (SE-HPLC), with 25 ug of the sample injected onto a Superdex 200 Increase 10/300 GL column (GE Healthcare, Cat. No. 28990944) monitored at 280 nm with a PBS mobile phase (0.75 mL/min). See FIG. 5. The antibody integrity was evaluated by GXII microfluidics electropherograms (Caliper, Chip ID: P099P-0563N-03) and was set up according to the manufacturer's instructions. See FIG. 6.

Results:

mAb1 was successfully conjugated via lysine with DFO as shown by UV/VIS spectroscopy. The calculated chelating moiety-to-antibody ratio of 1.7 was within the expected range of 1.0 to 2.0. SEC traces show 97.5% monomeric product with no detectable lower molecular weight species. This result is corroborated by electropherograms of both reduced and non-reduced state.

TABLE 7

Extinction Coefficients and Molecular Weight of Naked Antibody.

| Parent mAb Lot | MW (gmol$^{-1}$) | $\epsilon_{280}$ ($M^{-1}cm^{-1}$) | $\epsilon_{252}$ ($M^{-1}cm^{-1}$) |
|---|---|---|---|
| mAb1-L1 | 145654 | 212400 | 80493 |

TABLE 8

Chelating Moiety-to-Antibody Ratio, Concentration and Monomeric Purity of Conjugate.

| Conjugate Lot | UV Chelating Moiety-to-Antibody Ratio | Concentration (mg/mL) | % Monomeric |
|---|---|---|---|
| mAb1-L2 | 1.68 | 5.57 | 97.5% |

Example 8: $^{89}$Zr Chelation of DFO Conjugated Monoclonal Antibodies

For usage in ImmunoPET in vivo studies, the DFO-conjugated anti-CD8 antibody, mAb1-L2, was radiolabeled with $^{89}$Zr.

The DFO-Ab immunoconjugate solutions were formulated prior to chelation in identical fashion for both Study numbers 1 and 2. The formulation composition is listed in Table 9. In short, DFO-Ab immunoconjugate (212 ug) was first brought to 1.06 mg/mL in 1 M HEPES, pH 7.2. Separately, $^{89}$Zr solution was prepared using the compositions for each corresponding study shown in Table 10. Stock $^{89}$Zr-oxalic acid solution was obtained from 3D Imaging. The final radioactivity of the solution was first confirmed using a Capintec CRC-25R dose calibrator (Capintec #502), then immediately combined with the DFO-Ab immunoconjugate solution, gently mixed (pipetting up-and-down) and subsequently incubated for 45 minutes at room temperature. Total reaction volume was 1200 uL.

After the incubation, the mixtures were transferred to desalting columns, PD-10 (GE Healthcare, Cat. #: 17-0851-01) pre-equilibrated with 250 mM sodium acetate at pH 5.4 for gravity-fed desalting. After the contents of the reaction entered the column bed, the flow through was discarded. The product was eluted with 250 mM sodium acetate at pH 5.4

(formulation buffer) and eluate was collected as per manufacturer's instructions. The concentration of the product, now referred to as DFO-Ab radioimmunoconjugate, was subsequently measured by UV/VIS spectroscopy, and calculated using the appropriate extinction coefficient and the absorption at 280 nm using the equation:

Concentration in mg/mL=Absorption at 280 nm÷Extinction coefficient at 280 nm

See Table 11.

The final mass measured in grams was recorded in Table 12. The radioactivity was then measured using the dose calibrator (Capintec, CRC-25R) and reported in Table 12. The final material (5 ug) was analyzed using a SEC-HPLC with UV 280 and radioisotope detector (gamma emission) connected in series (Agilent 1260 with Lablogic Radio-TLC/HPLC Detector, SCAN-RAM) using a Superdex 200 Increase 10/300 GL column (GE Healthcare, Cat. No. 28990944) with PBS mobile phase at a flow rate of 0.75 mL/min. The radiotrace was used for determining radiochemical purity (100%—percent of unlabeled $^{89}$Zr) by comparing the integration of the total protein peak (~10 to ~18 min) and unlabeled $^{89}$Zr peak (~ 25 min). The percent monomeric purity was determined by the UV 280 trace by comparing the integration of the high molecular weight (HMW) species peak (~10 min to 15 min) to the monomer (~15 to ~18 min).

Figure 7:
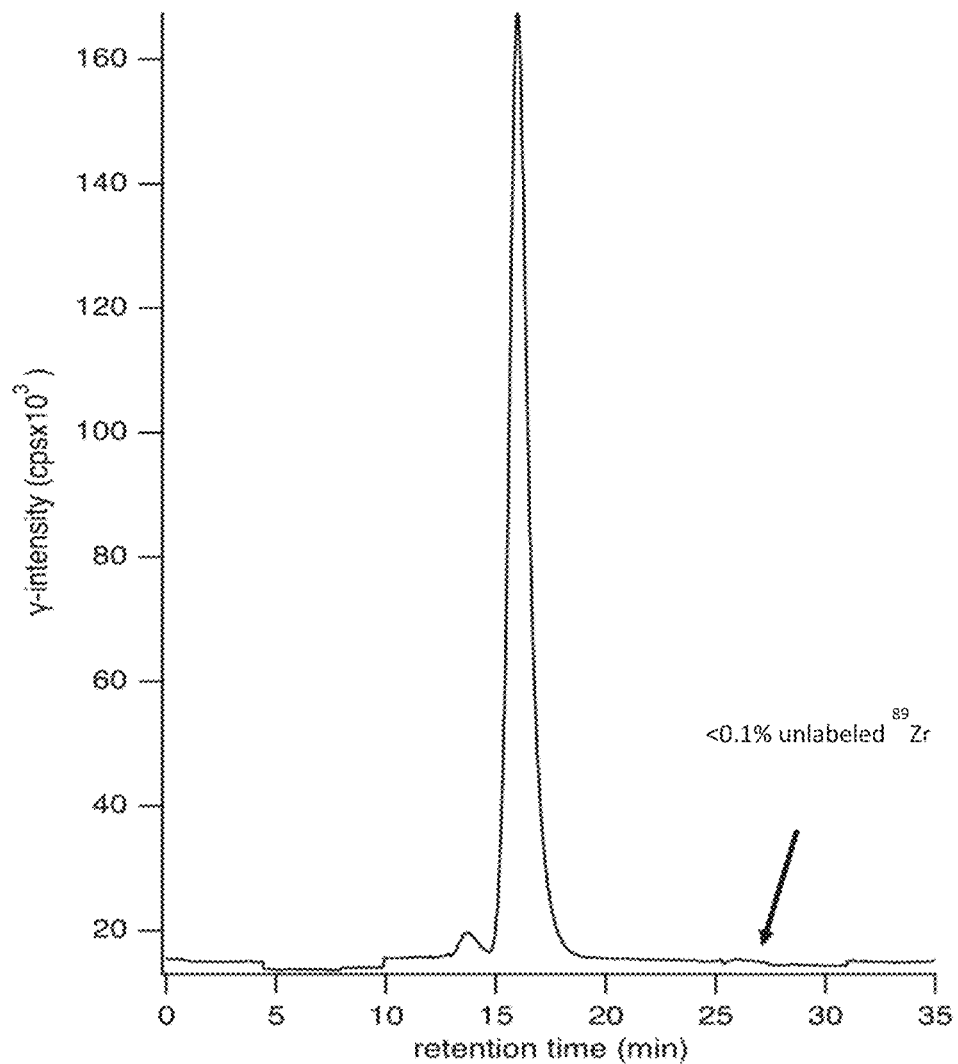
FIG. 7 depicts SEC-HPLC chromatogram of mAb1-L2-111016 radioimmunoconjugate on Superdex 200 Increase column with gamma emission detection. Unlabeled $^{89}$Zr makes up less than 0.1% of total integrated activity.
Figure 8:
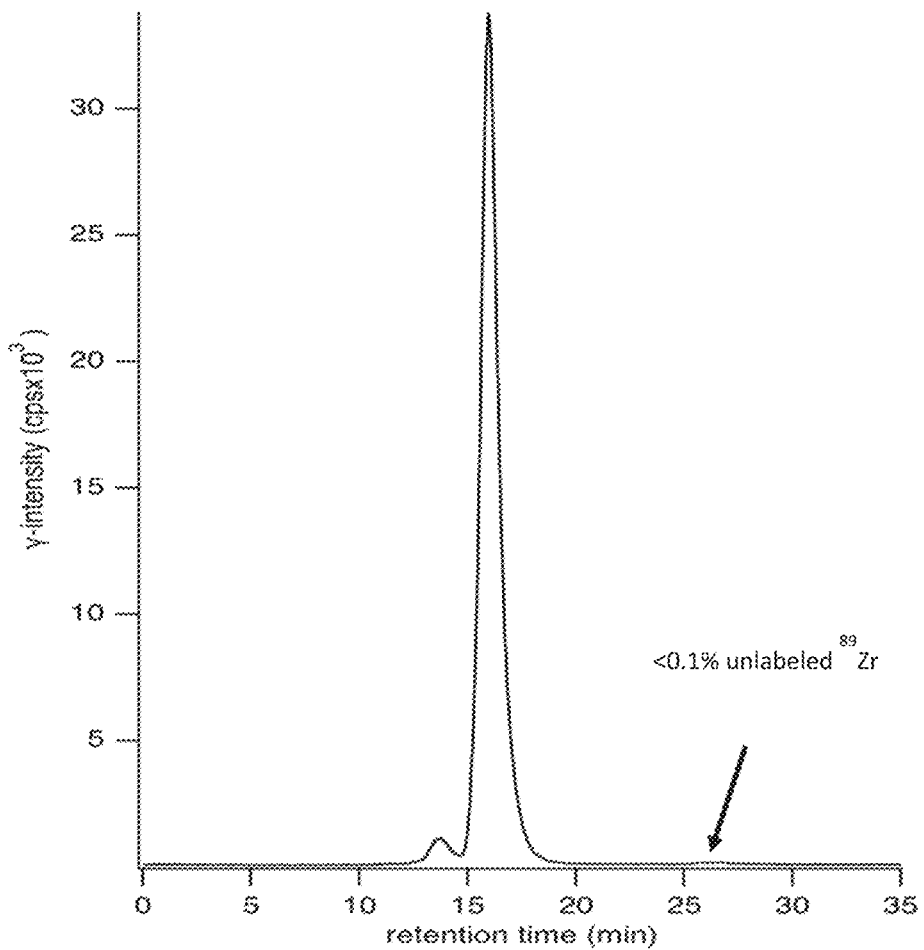
FIG. 8 depicts SEC-HPLC chromatogram of mAb1-L2-111516 radioimmunoconjugate on Superdex 200 Increase column with gamma emission detection. Unlabeled $^{89}$Zr makes up less than 0.1% of total integrated activity.
Figure 9:
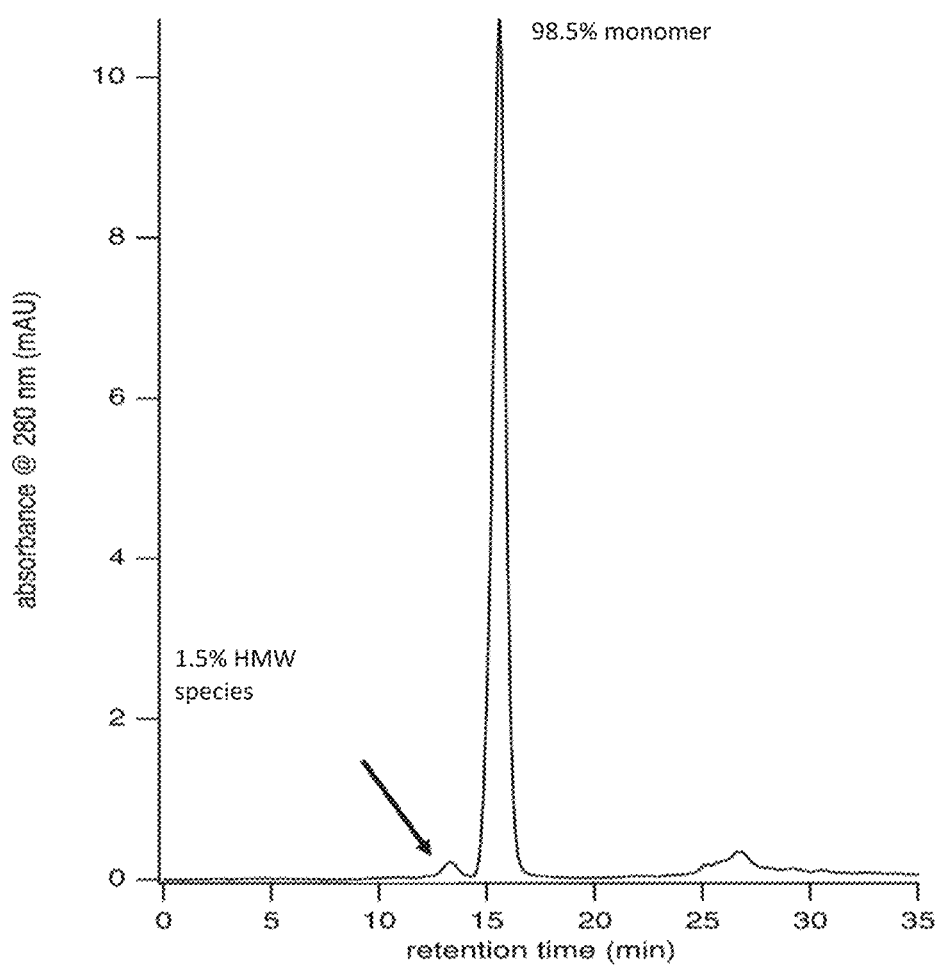
FIG. 9 depicts SEC-HPLC chromatogram of mAb1-L2-111016 radioimmunoconjugate on Superdex 200 Increase column with UV 280 nm absorbance detection. Monomeric (98.5%) and high molecular weight (HMW) species (1.5%) are indicated.
Figure 10:
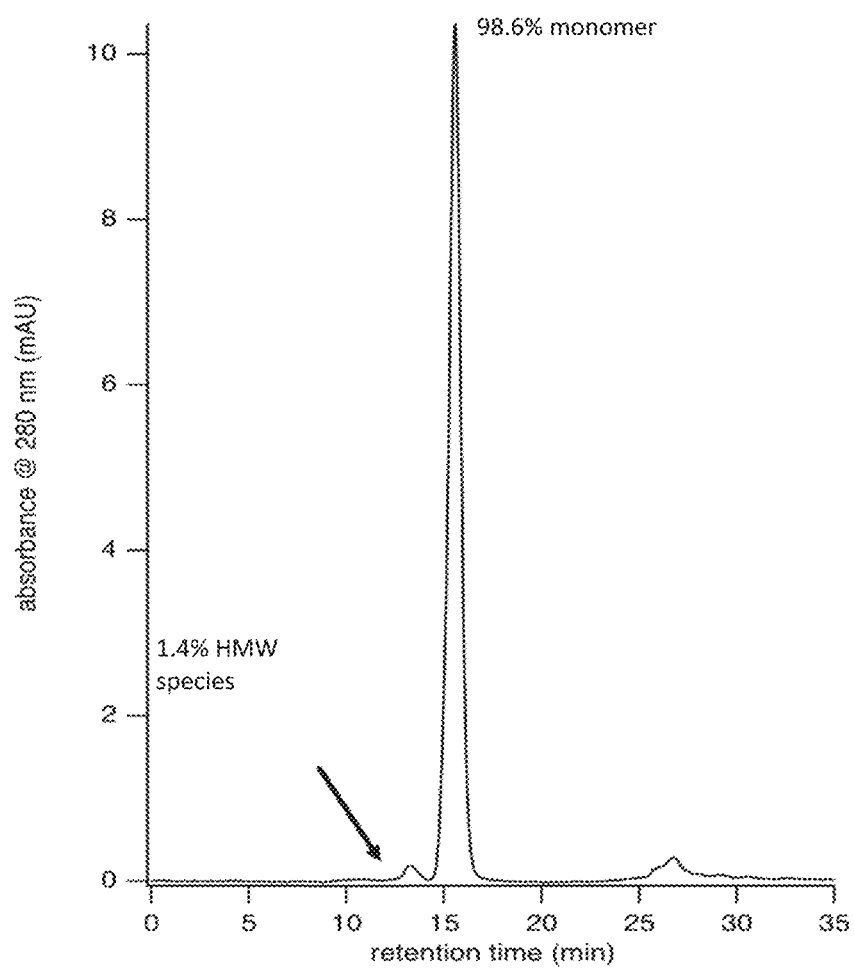
FIG. 10 depicts SEC-HPLC chromatogram of mAb1-L2-111516 radioimmunoconjugate on Superdex 200 Increase column with UV 280 nm absorbance detection. Monomeric (98.6%) and high molecular weight (HMW) species (1.4%) are indicated.

The specific activity and protein recovery (%) of each DFO-Ab radioimmunoconjugate was determined using the following equations:

a. Mass of conjugate in mg=concentration in mg/mL× mass of solution in grams
b. Specific activity in mCi/mg=activity of vial in mCi÷mass of conjugate in mg
c. Protein recovery=starting conjugate mass (mg)÷Mass of conjugate in mg Finally, the appearance was noted and recorded in Table 12. The results are consolidated in Table 12. The radio-SEC-HPLC chromatograms, shown in FIGS. 7 and 8, confirm at least 99.9% radiochemical purity. The UV280-HPLC SEC chromatograms shown in FIGS. 9 and 10 confirm the highly monomeric product (>90%).

The data demonstrate the DFO-radioimmunoconjugate was successfully and consistently radiolabeled with $^{89}$Zr in both studies.

TABLE 9

DFO-antibody Conjugate Preparation for Radiolabeling

| Radio-labeling # | Study # | DFO-Ab immune-conjugate Lot# | Concentration (mg/mL) | Chelating Moiety-to-Antibody Ratio | Conjugate mass (mg) | Total volume (uL) | Final Concentration (mg/mL) |
|---|---|---|---|---|---|---|---|
| 1 & 2 | 1 & 2 | mAb1-L2 | 5.57 | 1.68 | 212 | 200 | 1.06 |

TABLE 10

$^{89}$Zr Reaction Solution Preparation for Radiolabeling

| Radio-labeling | Study # | $^{89}$Zr-oxalate (uL) | 1M HEPES, pH 7.2 (uL) | Final Vol (uL) | Final Activity (uCi) | Specific Activity (uCi/uL) |
|---|---|---|---|---|---|---|
| 1 | 1 | 8.0 | 992.0 | 1000 | 5220 | 5.220 |
| 2 | 2 | 6.8 | 993.2 | 1000 | 1607 | 1.607 |

TABLE 11

Extinction Coefficients for Conjugate Lots

| DFO-Ab conjugate | $\varepsilon_{280}$ (AU ml mg$^{-1}$ cm$^{-1}$) |
|---|---|
| mAb1-L2 | 1.68 |

TABLE 12

Summary of $^{89}$Zr labeled DFO-Ab immunoconjugates for in vivo imaging and biodistribution studies

| Radio-labeling | Study # | Radioimmuno conjugate Lots | Appearance | Radio-chemical Purity* (%) | Monomeric Purity** (%) | Protein Recovery (%) | Conc. (mg/mL) | Specific Activity (mCi/mg) |
|---|---|---|---|---|---|---|---|---|
| 1 | 1 | mAb1-L2-111016 | Clear | >99.9 | 98.5 | 71 | 0.085 | 24.8 |
| 2 | 2 | mAb1-L2-111516 | Clear | >99.9 | 98.6 | 72 | 0.087 | 7.19 |

*by radio-SEC-HPLC,
**by UV-SEC-HPLC

Example 9: Immunoreactivity

The immunoreactivity (IR) of the radiolabeled anti-CD8 antibody prepared according to Examples 7 and 8 was determined as follows. All solutions buffers/rinses were made up with PBS and 10% fetal bovine serum (Seradigm, Cat #1500-500). Table 13 provides the number of cells used for each IR assay. For each assay, ~107 JRT3.T3/AP1-luc/hCD28/hCD8AB 1G4 cells were brought to a final volume of 0.5 mL. Twenty ng of the respective DFO-Ab radioimmunoconjugate was added to this solution and incubated 45 minutes at 37° C., 5% $CO_2$ in an incubator (ThermoScientific, Forma Steri-Cycle CO2) with continuous mixing on a tube rotator. The cells were then spun down at 1500 rpm for 5 minutes, creating "cell pellet A". The supernatant (~0.5 mL) was removed and introduced to another pellet of naïve cells, called "cell pellet B", and allowed to incubate at 37° C., 5% $CO_2$ for 45 minutes again. While cell pellet B was incubating, cell pellet A was rinsed three times with 1 mL fresh media, spinning at 1500 rpm for 5 minutes. Each rinse was collected and saved for later analysis. After the 45-minute cell pellet B incubation time, it was subsequently rinsed three times with 1 mL fresh media, spinning at 1500 rpm for 5 minutes. Again, each rinse was collected for analysis.

The radioactivity of the cell pellets, all rinses and the supernatant were counted in an automatic gamma counter (2470 Wizard2, Perkin Elmer) for each immuno-radioimmunoconjugate. The percentage IR was determined by equation 1 and recorded in Table 14:

$$IR(\%) = \frac{\text{Cell Pellet } A + \text{Cell Pellet } B(CPM)}{\text{Cell Pellet } A + \text{Cell Pellet } B + \text{Rinse } 1 + \text{Rinse } 2 + \text{Rinse } 3 + \text{Supernatant}[CPM]}$$

As seen in Table 14, antibody radioimmunoconjugates retained at least 55% immunoreactivity following conjugation and radiolabeling.

TABLE 13

Cell Numbers Used Per Pellet for Each Radioimmunoconjugate Lot

| Radioimmunoconjugate Lot# | Cell Number Pellet A | Cell Number Pellet B |
|---|---|---|
| mAb1-L2-111016 | 2.25 *$10^7$ cells | 2.25*$10^7$ cells |
| mAb1-L2-111516 | 1.5*$10^7$ cells | 1.5*$10^7$ cells |

TABLE 14

Immunoreactivity of $^{89}$Zr chelated DFO-conjugates

| Samples | mAb1-L2-111016 | mAb1-L2-111516 |
|---|---|---|
| Immunoreactivity | 57% | 55% |

Example 10: Selective Localization of Radiolabeled Anti-CD8 Antibody In Vivo in Mice Expressing hCD8

Dosing and PET/CT Imaging of $^{89}$Zr-DFO-mAb1:

16 week-old mice expressing hCD8 were injected with $^{89}$Zr-DFO-mAb1 at a protein dose of 0.5 or 1.5 mg/kg. The mice injected with a 0.5 mg/kg dose received 7 µg of radiolabeled mAb1-L2-20161115 (~48 µCi) and additional 8 µg non-DFO conjugated mAb1 (L1) as supplement to yield the final total injected protein dose. The mice injected with a 1.5 mg/kg dose received 7 µg of radiolabeled mAb1-L2-20161115 (~48 µCi) and additional 38 µg non-DFO conjugated mAb1 (L1) as supplement to yield the final total injected protein dose.

PET imaging of antibody localization was assessed 6 days after administration of $^{89}$Zr-DFO-mAb1. A Sofie Biosciences G8 PET/CT was used to acquire PET/CT images (Sofie Biosciences and Perkin Elmer). The instrument was pre-calibrated for detection of $^{89}$Zr prior to image acquisition. The energy window ranged from 150 to 650 keV with a reconstructed resolution of 1.4 mm at the center of the field of view. Mice underwent induction anesthesia using isoflurane and were kept under continuous flow of isoflurane during imaging. Static 10-minute images were acquired using the G8 acquisition software and subsequently reconstructed using the pre-configured settings. Image data was corrected for decay and other parameters. CT images were acquired following PET acquisition and subsequently co-registered with the PET images. Images were prepared using VivoQuant post-processing software (inviCRO Imaging Services).

Biodistribution of $^{89}$Zr-DFO-mAb1:

For biodistribution studies, mice were euthanized at the final time-point (6 days post-$^{89}$Zr-DFO-mAb1 administration) and blood was collected via cardiac puncture. Tissues were excised, placed in counting tubes, and weighed. Count data for $^{89}$Zr in counts per minute (CPM) was acquired using an automatic gamma counter (Wizard 2470, Perkin Elmer). The percent-injected dose per gram (% ID/g) was calculated for each sample using standards prepared from the injected material.

Figure 11:
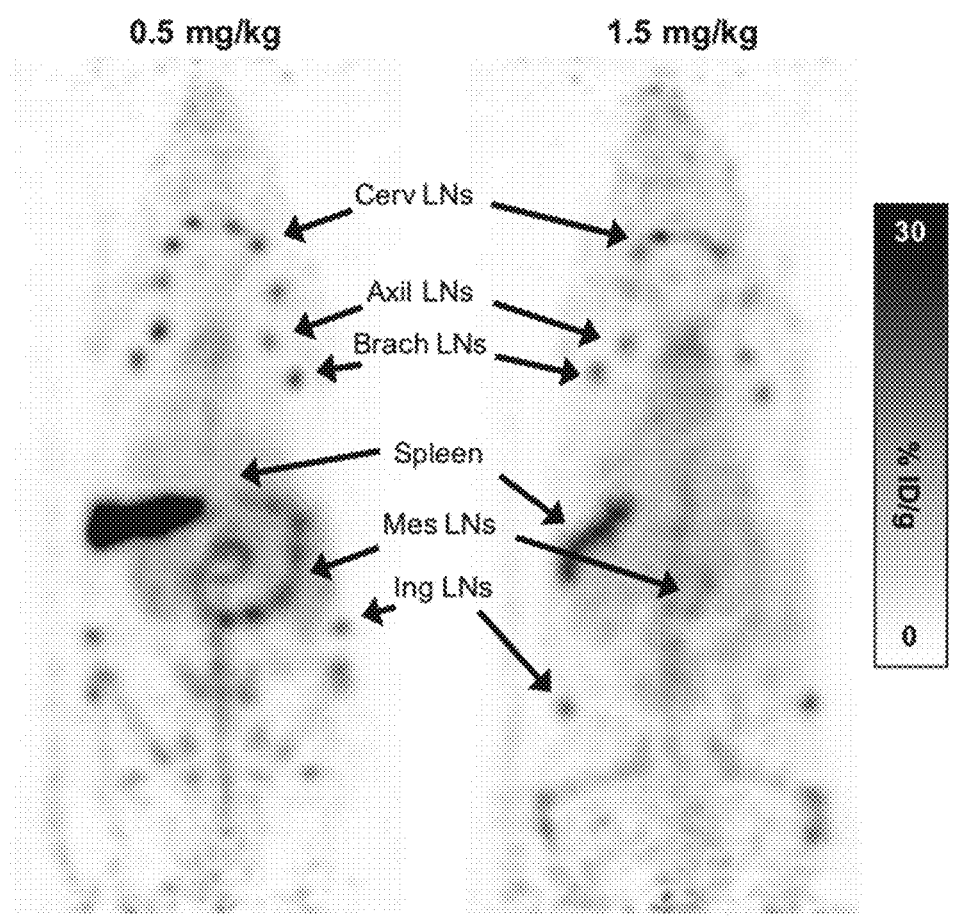
FIG. 11 provides representative PET images of $^{89}$Zr-DFO-mAb1 injected at protein doses of 0.5 or 1.5 mg/kg in mice expressing hCD8. Specific uptake of $^{89}$Zr-DFO-mAb1 is detected in the spleen and lymph nodes of mice expressing hCD8 at both doses administered. A reduction of uptake is detected in the spleen and lymph nodes at the higher protein dose of 1.5 mg/kg, indicating targeting specificity to lymphoid organs. Abbreviations: Cerv LNs—cervical lymph nodes; Axil LNs—axillary lymph nodes; Brach LNs—brachial lymph nodes; Mes LNs—mesenteric lymph nodes; Ing LNs—inguinal lymph nodes.

Results:

This experiment demonstrated the ability of $^{89}$Zr-DFO-mAb1 to target human CD8 expressed on endogenous T cells in the spleen and lymph nodes of mice expressing hCD8. The lower administered protein dose of 0.5 mg/kg demonstrated faster antigen-mediated clearance from the blood at day 6 post-radiotracer injection (3.57±1.50% ID/g) compared to the higher administered protein dose of 1.5 mg/kg (10.32±1.54% ID/g). This faster clearance from the blood in mice injected with the lower administered protein dose can be attributed to higher uptake in secondary lymphoid organs than the mice injected with the higher administered protein dose, demonstrating antigen-specific targeting to CD8 expressed in the spleen and lymph nodes. The % ID/g values from the biodistribution at day 6 post-$^{89}$Zr-DFO-mAb1 injection in mice expressing hCD8 are shown in Table 15. Representative iPET images of 0.5 and 1.5 mg/kg $^{89}$Zr-DFO-mAb1 at day 6 post-injection in mice expressing hCD8 are shown in FIG. 11.

TABLE 15

Ex vivo biodistribution at day 6 after administration of $^{89}$Zr-DFO-mAb1 injected at a protein doses of 0.5 or 1.5 mg/kg to mice expressing hCD8.

| | 0.5 mg/kg (n = 3) | | 1.5 mg/kg (n = 3) | |
|---|---|---|---|---|
| SAMPLE | Average % ID/g | STDEV % ID/g | Average % ID/g | STDEV % ID/g |
| Blood | 3.57 | 1.50 | 10.32 | 1.54 |
| Ing LNs | 85.30 | 24.35 | 71.00 | 17.83 |
| Axil LNs | 103.56 | 7.00 | 65.71 | 12.13 |
| Spleen | 105.51 | 18.60 | 37.07 | 4.80 |
| Thymus | 9.63 | 0.93 | 13.83 | 0.53 |

TABLE 15-continued

Ex vivo biodistribution at day 6 after administration of $^{89}$Zr-DFO-mAb1 injected at a protein doses of 0.5 or 1.5 mg/kg to mice expressing hCD8.

| SAMPLE | 0.5 mg/kg (n = 3) | | 1.5 mg/kg (n = 3) | |
|---|---|---|---|---|
| | Average % ID/g | STDEV % ID/g | Average % ID/g | STDEV % ID/g |
| Heart | 1.28 | 0.23 | 2.81 | 0.46 |
| Lungs | 4.11 | 2.68 | 6.63 | 0.94 |
| Stomach | 0.64 | 0.17 | 0.70 | 0.20 |
| S Intestine | 6.28 | 2.42 | 4.78 | 1.06 |
| Liver | 5.05 | 1.92 | 3.97 | 0.44 |
| Kidneys | 10.00 | 0.96 | 6.44 | 0.69 |
| Muscle | 0.47 | 0.21 | 0.84 | 0.20 |
| Bone | 3.73 | 0.55 | 4.16 | 0.51 |
| Axil LNs-to-blood ratio | 32.67 | 14.15 | 6.35 | 0.39 |
| Spleen-to-blood ratio | 31.93 | 8.72 | 3.6 | 0.14 |

Values are shown as averages and standard deviations of percent injected dose per gram tissue (% ID/g) and tissue-to-blood ratios. (n = 3 for both 0.5 and 1.5 mg/kg protein doses). Abbreviations: Ing LNs-inguinal lymph nodes; Axil LNs-axillary lymph nodes; S Intestine-small intestine.

Example 11: Selective Localization of Radiolabeled Anti-CD8 Antibody to Raji/PBMC Tumors in Mice This Example describes the in vivo imaging and ex vivo biodistribution of a Zirconium$^{-89}$ labeled DFO-anti-CD8 antibody conjugate in female NSG mice co-implanted with Raji cells and human PBMC.

Implantation of Tumors and Allocation of Dosing Groups:

To demonstrate specificity of the radiolabeled antibody for CD8 targeting, 2×10$^6$ Raji cells were implanted alone or co-implanted with 5×10$^5$ human PBMCs (Lot 0160614, ReachBio Research Labs) into the right flank of female NSG mice (8-10 weeks old; NOD.Cg-Prkdc$^{scid}$ Il2rg$^{tmWjil}$/SzJ; Jackson Labs). Tumor growth was monitored and 13-14 days post-tumor implantation mice were randomized into groups of 4 for $^{89}$Zr-DFO-mAb1 dosing. Raji and Raji/hPBMC tumors were ~335±68 mm$^3$ and ~371±40 mm$^3$, respectively, when administered with $^{89}$Zr-DFO-mAb1.

Dosing and PET/CT Imaging of $^{89}$Zr-DFO-mAb1:

Mice bearing subcutaneous Raji or Raji/hPBMC tumors were injected with a 0.1 mg/kg dose of $^{89}$Zr-DFO-mAb1 (~66 µCi and 2.8 µg protein).

PET imaging of antibody localization was assessed 6 days after administration of $^{89}$Zr-DFO-mAb1. A Sofie Biosciences G8 PET/CT was used to acquire PET/CT images (Sofie Biosciences and Perkin Elmer). The instrument was pre-calibrated for detection of $^{89}$Zr prior to image acquisition. The energy window ranged from 150 to 650 keV with a reconstructed resolution of 1.4 mm at the center of the field of view. Mice underwent induction anesthesia using isoflurane and were kept under continuous flow of isoflurane during imaging. Static 10-minute images were acquired using the G8 acquisition software and subsequently reconstructed using the pre-configured settings. Image data was corrected for decay and other parameters. CT images were acquired following PET acquisition and subsequently co-registered with the PET images. Images were prepared using VivoQuant post-processing software (inviCRO Imaging Services).

Biodistribution of $^{89}$Zr-DFO-mAb1:

For biodistribution studies, blood was collected via cardiac puncture after the final PET scan at 6 days post-$^{89}$Zr-DFO-mAb1 administration). Mice were euthanized and Raji or Raji/hPBMC tumors, along with other normal tissues, were then excised, placed in counting tubes, and weighed. Count data for $^{89}$Zr in counts per minute (CPM) was acquired using an automatic gamma counter (Wizard 2470, Perkin Elmer). The percent-injected dose per gram (% ID/g) was calculated for each sample using standards prepared from the injected material.

Figure 12:
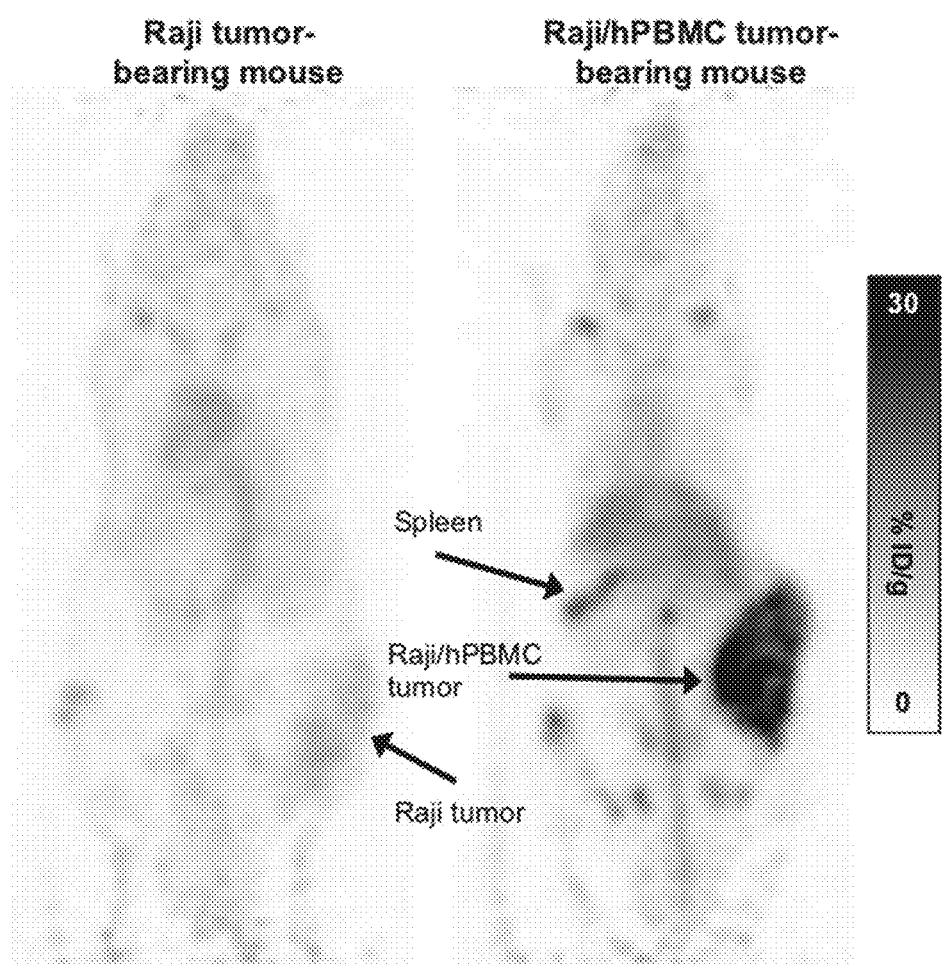
FIG. 12 shows representative PET images of $^{89}$Zr-DFO-mAb1 injected at a protein dose of 0.1 mg/kg in Raji and Raji/hPBMC tumor-bearing mice. Specific uptake of 89Zr-DFO-mAb1 is detected in the spleen and tumor of Raji/hPBMC tumor-bearing mice.

Results:

This study demonstrates antigen-specific targeting of $^{89}$Zr-DFO-mAb1 to CD8 expressed on intratumoral human lymphocytes in s.c. Raji/hPBMC tumors (31.11±8.82% ID/g) compared to Raji only tumors (6.39±0.93% ID/g) grown in NSG mice. Tumor-to-blood ratios of Raji/hPBMC and Raji only tumors were 3.32±0.11 and 0.43±0.07, respectively. Furthermore, there is increased uptake in the spleens of mice that have been co-implanted with Raji/hPBMC tumors. Representative iPET images (FIG. 12) of Raji and Raji/hPBMC tumor-bearing mice at day 6 post-$^{89}$Zr-DFO-mAb1 injection demonstrate higher targeting of $^{89}$Zr-DFO-mAb1 to the tumor and spleen of the Raji/hPBMC tumor-bearing mice compared to Raji tumor-bearing mice. The % ID/g values from the biodistribution at day 6 post-$^{89}$Zr-DFO-mAb1 injection (Table 16) confirm the iPET imaging data.

TABLE 16

Ex vivo biodistribution at day 6 after administration of $^{89}$Zr-DFO-mAb1 injected at a protein dose of 0.1 mg/kg to Raji or Raji/hPBMC tumor-bearing NSG mice.

| SAMPLE | Raji tumor-bearing mice | | Raji/hPBMC tumor-bearing mice | |
|---|---|---|---|---|
| | Average % ID/g | STDEV % ID/g | Average % ID/g | STDEV % ID/g |
| Blood | 14.81 | 0.96 | 10.14 | 2.79 |
| Tumor | 6.39 | 0.93 | 31.11 | 8.82 |
| Spleen | 4.75 | 0.35 | 56.35 | 36.45 |
| Thymus | 6.56 | 1.70 | 3.96 | 0.76 |
| Heart | 3.42 | 0.65 | 2.41 | 0.57 |
| Lungs | 11.22 | 1.76 | 9.02 | 0.40 |
| Stomach | 0.57 | 0.08 | 0.56 | 0.19 |
| S Intestine | 1.18 | 0.26 | 1.01 | 0.23 |
| Liver | 2.62 | 0.13 | 8.64 | 3.04 |
| Kidneys | 4.00 | 0.59 | 4.31 | 0.78 |
| Muscle | 1.08 | 0.17 | 0.84 | 0.20 |
| Bone | 2.81 | 0.55 | 5.36 | 1.29 |
| Tumor-to-blood ratio | 0.43 | 0.07 | 3.32 | 0.11 |

Values are shown as average and standard deviations of percent injected dose per gram tissue (% ID/g) and tumor-to-blood ratios.

Example 12: Treatment of Mice with Weak CD8 Functional Blocker Mab1 does not Negatively Impact the Clearance of Acute LCMV Infection in Humanized Mice The experimental data from this example is based on a previously published model: infection of C57Bl/6 mice with the Armstrong strain of lymphocytic choriomeningitis virus (Armstrong strain of LCMV or LCMV Arm) causes an acute infection whose resolution is dependent upon the generation of a functional CD8+ CTL response (PNAS. Vol. 91, pp. 10854-10858; J Virol. 1987 June; 61(6):1867-74). In this example, mice were genetically engineered to express human TCRs, HLA, CD4 and CD8 co-receptors, referred to as humanized mice. The humanized mice were challenged with LCMV Arm (2×10$^5$ ffu (focus forming unit), intraperitoneal injection (i.p.)) and demonstrated a resolution of acute infection similar to control C57Bl/6 mice, albeit with slightly delayed kinetics (day 12-21 post-infection vs day 8-10 in controls) (data not shown).

In this example, the LCMV acute infection model in humanized mice was used to assess the effect of anti-human CD8 antibodies with differential blocking activity on virus clearance. Groups consisted of mice treated with A) a CD8 T cell depleting antibody (OKT8), which is considered the positive control, B) a strong blocking antibody of CD8 activity, C) a weak blocking antibody CD8 activity (Mab1), and D) a non-CD8-binding protein control. The blocking activities of B and C were assessed using the engineered bioassay described in Example 5.

The depleting OKT8 antibody was administered 2 days prior, 1 day prior and 1 day after infection at 100 ug/dose i.p., while the other treatment conditions were delivered as a single dose of 0.5 mg/kg i.p. one day prior to injection. Mice were infected with LCMV Arm ($2 \times 10^5$ ffu i.p.) and spleens were harvested from groups of mice at day 5, 14, and 21 post infection. Virus titers were assessed from homogenized spleen tissue using standard plaque assay methods.

Figure 13:
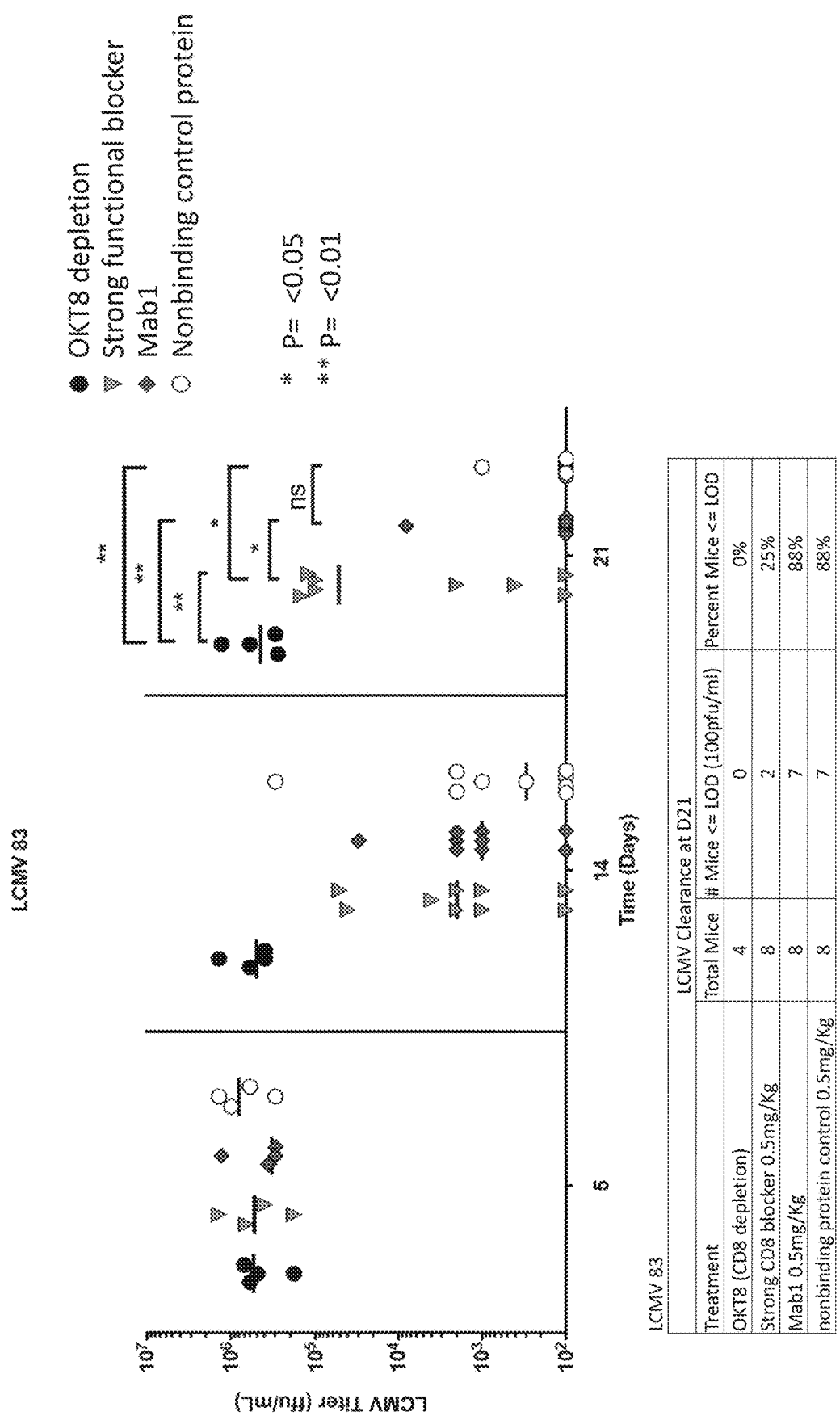
FIG. 13 compares antibody treatment of mice infected with LCMV, and demonstrates that mice treated with mAb1 retained the ability to clear LCMV relative to mice treated with a strong CD8 blocking antibody.

At day 5 post infection, as shown in FIG. 13, all treatment groups had high titers of LCMV ($>1 \times 10^5$ ffu/ml) demonstrating proper establishment of virus infection in the genetically modified mice. As in C57B1I/6 mice, the clearance of LCMV in humanized mice is CD8 dependent, since depletion of CD8 T cells using the OKT8 anti-human CD8 antibody results in a delay in clearance of LCMV infection over the first month post infection. Mice treated with the OKT8 CD8 depletion antibody failed to clear virus and maintained high virus titers ($>1 \times 10^5$ ffu/ml) at both day 14 and day 21 post-infection, while the control group progressively cleared the virus to the limit of detection (LOD 100 ffu/ml). Mice treated with a single dose of Mab1, a weak CD8 blocker of CD8 T cell function, demonstrated clearance of virus similar to the non-binding control with no statistical difference (n.s.). Treatment of mice with a single dose of antibody that strongly blocks CD8 function exhibited an intermediate virus clearance phenotype that was statistically different to both the weak blocker and non-binding protein control groups at day 21 ($p<0.05$). All treatment groups at day 21 were statistically different from the OKT8 depletion group ($p<0.01$). See FIG. 13.

Collectively, the data demonstrate that the weaker blocking antibody to CD8 (mAb 1), at a therapeutically relevant dose, does not impair the ability of humanized mice to clear LCMV infection, and therefore, T cell function is unimpaired when compared to both the positive control (CD8 depleting antibody) and negative control (non-binding protein control).

Example 13: Conjugation of mAb1 with NIR Fluorescent Compounds

Approximately 10 mg of the antibody, mAb1, was buffer exchanged from the formulation buffer (histidine-based) to 50 mM carbonate, pH 8.4, via a pre-conditioned Nap-5 column (GE Healthcare, Cat. #: 17085302) according to the manufacturer's instructions. This process was performed in quadruplicate; each elution (400 µL) was collected and combined for a total of 1600 µL. The combined elution concentration was determined to be 18.1 mg/mL by UV/VIS spectrometry (Nanodrop 2000 UV/VIS spectrometer, Thermo Scientific, Cat. #ND-2000c-US-CAN).

For IRDye 800CW (Li-Cor, Cat. #: 929-70020) conjugations, either 2, 4, or 6-fold mol-to-mol excess of 10 mM of IRDye 800CW NHS Ester in DMSO was introduced to 7.2 mg (400 µL) of the buffer exchanged mAb1. After gentle mixing by pipette, the reaction was allowed to proceed for 2 hours at room temperature, quiescent in the dark.

For the cyanine-based Vivotag680XL (Perkin-Elmer, Cat. #: NEV11120) conjugation, a 2-fold mol-to-mol excess of 10 mM VivoTag680XL in DMSO was introduced to 7.2 mg (400 µL) of the buffer exchanged mAb1. After gentle mixing by pipette, the reaction was allowed to proceed for 2 hours at room temperature, quiescent in the dark.

Each conjugation reaction was buffer exchanged by a Nap-5 column pre-conditioned with PBS plus 5% glycerol, pH 7.4 to remove reacted dye. In short, for each conjugation reaction, the total elution of 1000 µL was fractioned, and each fraction was assayed for the presence of protein by the UV/VIS spectrometer. Fractions with high protein content were combined. The final protein concentration and dye-to-antibody ratio (DAR) for each reaction was determined by UV/VIS spectrometry following the manufacturer's instructions. Results are summarized in Table 17.

Under all conjugation conditions, the monomeric purity was determined to be greater than or equal to 95.0% as assayed by size exclusion high-performance liquid chromatography, SE-HPLC, monitoring at absorbance 280 nm (column: Superdex 200 10/300 GL SEC Column, GE Lifesciences, Cat. #: 28990944). Results are summarized in Table 17. Antibody integrity was assayed by sodium dodecyl sulfate polyacrylamide gel electrophoresis (SDS-PAGE, Novex 4-20% Tris-Glycine Gel, ThermoFisher Scientific, Cat. #: EC6026BOX) under both reduced and non-reduced conditions. As compared to the unconjugated antibody, fragmentation of the conjugates was not observed.

TABLE 17

DAR, concentration and monomeric purity of IR dye conjugates.

| Dye | Conjugation Condition (dye-to-antibody) | DAR | Final Concentration (mg/mL) | Monomeric Purity By SE-HPLC (%) |
|---|---|---|---|---|
| IRDye 800CW | 2-to-1 | 0.16 | 12.7 | 97.4 |
| IRDye 800CW | 4-to-1 | 0.34 | 12.5 | 97.5 |
| IRDye 800CW | 6-to-1 | 0.57 | 11.1 | 95.0 |
| VivoTag680 XL | 2-to-1 | 1.51 | 14.6 | 96.3 |

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

TABLE 18

| | Informal Sequence Listing | |
|---|---|---|
| SEQ ID NO. | Sequence | Description |
| 1. | caggtgcagc tggtggagtc tgggggaggc gtggaccagc ctgggaggtc cctgagactc tcctgtgcag cgtctggatt catcttcagt aactatggta ttcactgggt ccgtcaggct ccaggcaagg ggctggagtg ggtggcagtt atatggtatg atggaagtaa taaatacttt gaagactccg tgaagggccg attcaacatc tccagagaca attccaagaa catagtgtat ctgcaaatga acagcctgag agccgaggac acggctgtgt atttctgtgc gagaagttac gatatgttga ctgggtcggg tgactactac ggtttggacg tctggggcca agggaccacg gtcaccgtct cctca | DNA nucleotide sequence |
| 2. | QVQLVESGGG VDQPGRSLRL SCAASGFIFS NYGIHWVRQA PGKGLEWVAV IWYDGSNKYF EDSVKGRFNI SRDNSKNIVY LQMNSLRAED TAVYFCARSY DMLTGSGDYY GLDVWGQGTT VTVSS | AA amino acid sequence |
| 3. | ggattcatct tcagtaacta tggt | DNA nucleotide sequence |
| 4. | GFIFSNYG | AA amino acid sequence |
| 5. | atatggtatg atggaagtaa taaa | DNA nucleotide sequence |
| 6. | IWYDGSNK | AA amino acid sequence |
| 7. | gcgagaagtt acgatatgtt gactgggtcg ggtgactact acggtttgga cgtc | DNA nucleotide sequence |
| 8. | ARSYDMLTGS GDYYGLDV | AA amino acid sequence |
| 9. | gacatccaga tgacccagtc tccatcctca ctgtctgcat ctgtaggaga cagagtcacc atcacttgtc gggcgagtca ggacattacc aattatttag cttggtttca gcagaaacca gggaaagccc ctaagtccct gatctatggt gcatccagtt tgcaaagtgg ggtcccatca aagttcagcg gcagtggatc tgggacagat ttcactctca ccatcagcag cctgcagcct gaagattttg caacttatta ttgtcaacag tataacaatt atcctctcac tttcggcgga gggaccaagg tggagatcaa a | DNA nucleotide sequence |
| 10. | DIQMTQSPSS LSASVGDRVT ITCRASQDIT NYLAWFQQKP GKAPKSLIYG ASSLQSGVPS KFSGSGSGTD FTLTISSLQP EDFATYYCQQ YNNYPLTFGG GTKVEIK | AA amino acid sequence |
| 11. | caggacatta ccaattat | DNA nucleotide sequence |
| 12. | QDITNY | AA amino acid sequence |
| 13. | ggtgcatcc | DNA nucleotide sequence |
| 14. | GAS | AA amino acid sequence |
| 15. | caacagtata acaattatcc tctcact | DNA nucleotide sequence |
| 16. | QQYNNYPLT | AA amino acid sequence |

TABLE 18-continued

Informal Sequence Listing

| SEQ ID NO. | Sequence | Description |
|---|---|---|
| 17. | atgcatagac ctagacgccg gggtacaaga cctcccccac tcgcccttct cgccgccctc cttcttgctg cccgcggagc cgatgcatca caatttcgcg tgtcccccct tgatcgaacc tggaaccttg gcgagacagt tgaactcaaa tgccaggtgc tgctttccaa tcccacatca ggatgttcat ggcttttcca accacgaggc gctgctgcta gccccacttt tctcctttac ctttcccaaa acaaacctaa agccgccgaa ggactcgaca cacaacgctt ttcaggaaaa cgactcggcg atacctttgt actcactctc tcagatttta gacgcgaaaa tgaaggatat tatttctgct ccgcccctc aaattcaatc atgtatttct ctcatttgt tcctgtattc cttcccgcta accaactac cactcctgct ccccgccccc caacacctgc tcaactatt gcatcccaac cactctccct cagacccgaa gcttgtcgcc ccgccgcgg aggtgctgtt cacactagag gactcgattt tgcttgcgac atttatatct gggccccact tgcaggtact tgcggagtat tgctgctctc acttgttatt actctttatt gcaaccatag aaaccgacgc agagtttgca aatgtccacg ccagttgtc aagtcaggcg ataaaccttc acttagtgca cgatacgtct ga | DNA nucleotide sequence |
| 18. | SQFRVSPLDR TWNLGETVEL KCQVLLSNPT SGCSWLFQPR GAAASPTFLL YLSQNKPKAA EGLDTQRFSG KRLGDTFVLT LSDFRRENEG YYFCSALSNS IMYFSHFVPV FLPAKPTTTP APRPPTPAPT IASQPLSLRP EACRPAAGGA VHTRGLDFAC DIYIWAPLAG TCGVLLLSLV ITLYCNHRNR RRVCKCPRPV VKSGDKPSLS ARYV | AA amino acid sequence |
| 19. | atgcatcgcc ccgaagacg cggtactaga ccccaccc tcgcccttct ggcagcccctt ctgctcgccg ccgaggcgc tgacgccctt caacaaacac ccgcctacat taaagtccaa acaaacaaaa tggtaatgct gtcctgtgaa gctaagatat ccctttcaaa tatgcgcatt tactggctta dacaaagaca agcacccagc tcagactcac accatgaatt tctcgccctc tgggattccg caaaaggtac catccatgga gaagaagtag aacaagaaaa aattgcagta ttccgagatg ccagtcgatt catcctcaat ctgacttcag ttaaacccga agatagcggt atctactttt gcatgatcgt tggctcacca gaactcacct tcggtaaagg aacccaattg tccgtgtcg atttcctgcc cactacagcc caacctacca aaaagtcaac ccttaagaag agagtttgca gactgccag acccgaaaca cagaaaggac ccctctgctc tcctattaca cttggcttgc tcgtcgctgg agtcctcgtc cttcttgtat cccttggagt tgccattcac ctgtgttgta gacgccgccg cgccagactc cggtttatga agcagttta caaatga | DNA nucleotide sequence |
| 20. | LQQTPAYIKV QTNKMVMLSC EAKISLSNMR IYWLRQRQAP SSDSHHEFLA LWDSAKGTIH GEEVEQEKIA VFRDASRFIL NLTSVKPEDS GIYFCMIVGSPE LTFGKGTQLS VVDFLPTTAQ PTKKSTLKKR VCRLPRPETQ KGPLCSPITL GLLVAGVLVL LVSLGVAIHL CCRRRARLR FMKQFYK | AA amino acid sequence |

SEQUENCE LISTING

```
Sequence total quantity: 20
SEQ ID NO: 1                moltype = DNA  length = 375
FEATURE                     Location/Qualifiers
misc_feature                1..375
                            note = 1 VH
source                      1..375
                            mol_type = other DNA
                            organism = synthetic construct
SEQUENCE: 1
caggtgcagc tggtggagtc tgggggaggc gtggaccagc ctggggaggtc cctgagactc    60
tcctgtgcag cgtctggatt catcttcagt aactatggta ttcactgggt ccgtcaggct   120
ccaggcaagg ggctggagtg ggtggcagtt atatggtatg atggaagtaa taatactttt   180
gaagactccg tgaagggccg attcaacatc tccagagaca attccaagaa catagtgtat   240
ctgcaaatga acagcctgag agccgaggac acggctgtgt atttctgtgc gagaagttac   300
gatatgttga ctgggtcggg tgactactac ggtttggacg tctggggcca agggaccacg   360
gtcaccgtct cctca                                                    375

SEQ ID NO: 2                moltype = AA   length = 125
FEATURE                     Location/Qualifiers
REGION                      1..125
                            note = 2 VH
source                      1..125
```

```
                            mol_type = protein
                            organism = synthetic construct
SEQUENCE: 2
QVQLVESGGG  VDQPGRSLRL  SCAASGFIFS  NYGIHWVRQA  PGKGLEWVAV  IWYDGSNKYF   60
EDSVKGRFNI  SRDNSKNIVY  LQMNSLRAED  TAVYFCARSY  DMLTGSGDYY  GLDVWGQGTT  120
VTVSS                                                                  125

SEQ ID NO: 3                moltype = DNA   length = 24
FEATURE                     Location/Qualifiers
misc_feature                1..24
                            note = 3 CDR1
source                      1..24
                            mol_type = other DNA
                            organism = synthetic construct
SEQUENCE: 3
ggattcatct tcagtaacta tggt                                              24

SEQ ID NO: 4                moltype = AA    length = 8
FEATURE                     Location/Qualifiers
REGION                      1..8
                            note = 4 CDR1
source                      1..8
                            mol_type = protein
                            organism = synthetic construct
SEQUENCE: 4
GFIFSNYG                                                                 8

SEQ ID NO: 5                moltype = DNA   length = 24
FEATURE                     Location/Qualifiers
misc_feature                1..24
                            note = 5 CDR2
source                      1..24
                            mol_type = other DNA
                            organism = synthetic construct
SEQUENCE: 5
atatggtatg atggaagtaa taaa                                              24

SEQ ID NO: 6                moltype = AA    length = 8
FEATURE                     Location/Qualifiers
REGION                      1..8
                            note = 6 CDR2
source                      1..8
                            mol_type = protein
                            organism = synthetic construct
SEQUENCE: 6
IWYDGSNK                                                                 8

SEQ ID NO: 7                moltype = DNA   length = 54
FEATURE                     Location/Qualifiers
misc_feature                1..54
                            note = 7 CDR3
source                      1..54
                            mol_type = other DNA
                            organism = synthetic construct
SEQUENCE: 7
gcgagaagtt acgatatgtt gactgggtcg ggtgactact acggtttgga cgtc             54

SEQ ID NO: 8                moltype = AA    length = 18
FEATURE                     Location/Qualifiers
REGION                      1..18
                            note = 8 CDR3
source                      1..18
                            mol_type = protein
                            organism = synthetic construct
SEQUENCE: 8
ARSYDMLTGS GDYYGLDV                                                     18

SEQ ID NO: 9                moltype = DNA   length = 321
FEATURE                     Location/Qualifiers
misc_feature                1..321
                            note = 9 VK
source                      1..321
                            mol_type = other DNA
                            organism = synthetic construct
SEQUENCE: 9
gacatccaga tgacccagtc tccatcctca ctgtctgcat ctgtaggaga cagagtcacc        60
atcacttgtc gggcgagtca ggacattacc aattatttag cttggtttca gcagaaacca      120
gggaaagccc ctaagtccct gatctatggt gcatccagtt tgcaaagtgg ggtcccatca      180
aagttcagcg gcagtggatc tgggacagat ttcactctca ccatcagcag cctgcagcct      240
```

```
gaagatttttg caacttatta ttgtcaacag tataacaatt atcctctcac tttcggcgga    300
gggaccaagg tggagatcaa a                                               321
```

```
SEQ ID NO: 10              moltype = AA  length = 107
FEATURE                    Location/Qualifiers
REGION                     1..107
                           note = 10 VK
source                     1..107
                           mol_type = protein
                           organism = synthetic construct
SEQUENCE: 10
DIQMTQSPSS LSASVGDRVT ITCRASQDIT NYLAWFQQKP GKAPKSLIYG ASSLQSGVPS    60
KFSGSGSGTD FTLTISSLQP EDFATYYCQQ YNNYPLTFGG GTKVEIK                  107

SEQ ID NO: 11              moltype = DNA  length = 18
FEATURE                    Location/Qualifiers
misc_feature               1..18
                           note = 11 CDR1
source                     1..18
                           mol_type = other DNA
                           organism = synthetic construct
SEQUENCE: 11
caggacatta ccaattat                                                   18

SEQ ID NO: 12              moltype = AA  length = 6
FEATURE                    Location/Qualifiers
REGION                     1..6
                           note = 12 CDR1
source                     1..6
                           mol_type = protein
                           organism = synthetic construct
SEQUENCE: 12
QDITNY                                                                 6

SEQ ID NO: 13              moltype =     length =
SEQUENCE: 13
000

SEQ ID NO: 14              moltype =     length =
SEQUENCE: 14
000

SEQ ID NO: 15              moltype = DNA  length = 27
FEATURE                    Location/Qualifiers
misc_feature               1..27
                           note = 15 CDR3
source                     1..27
                           mol_type = other DNA
                           organism = synthetic construct
SEQUENCE: 15
caacagtata acaattatcc tctcact                                         27

SEQ ID NO: 16              moltype = AA  length = 9
FEATURE                    Location/Qualifiers
REGION                     1..9
                           note = 16 CDR3
source                     1..9
                           mol_type = protein
                           organism = synthetic construct
SEQUENCE: 16
QQYNNYPLT                                                              9

SEQ ID NO: 17              moltype = DNA  length = 732
FEATURE                    Location/Qualifiers
source                     1..732
                           mol_type = unassigned DNA
                           organism = Homo sapiens
SEQUENCE: 17
atgcatagac ctagacgccg gggtacaaga cctccccccac tcgcccttct cgccgccctc    60
cttcttgctg cccgcggagc cgatgcatca caatttcgcg tgtccccct tgatcgaacc    120
tggaaccttg gcgagacagt tgaactcaaa tgccaggtgc tgctttccaa tcccacatca   180
ggatgttcat ggcttttcca accacgaggc gctgctgcta gccccacttt tctccttttac  240
ctttcccaaa acaaacctaa agccgccgaa ggactcgaca cacaacgctt ttcaggaaaa   300
cgactcggcg atacctttgt actcactctc tcagatttta gacgcgaaaa tgaaggtat   360
tatttctgct ccgccctctc aaattcaatc atgtatttct ctcatttttgt tcctgtattc  420
cttcccgcta aaccaactac cactcctgct ccccgcccc caaacctgc tccaactatt    480
gcatcccaac cactctccct cagacccgaa gcttgtcgcc ccgccgccgg aggtgctgtt   540
cacactagag gactcgattt tgcttgcgac atttatatct gggcccacct tgcaggtact   600
tgcggagtat tgctgctctc acttgttatt actctttatt gcaaccatag aaaccgacgc   660
```

```
agagtttgca aatgtccacg accagttgtc aagtcaggcg ataaaccttc acttagtgca  720
cgatacgtct ga                                                      732

SEQ ID NO: 18          moltype = AA  length = 214
FEATURE                Location/Qualifiers
source                 1..214
                       mol_type = protein
                       organism = Homo sapiens
SEQUENCE: 18
SQFRVSPLDR TWNLGETVEL KCQVLLSNPT SGCSWLFQPR GAAASPTFLL YLSQNKPKAA   60
EGLDTQRFSG KRLGDTFVLT LSDFRRENEG YYFCSALSNS IMYFSHFVPV FLPAKPTTTP  120
APRPPTPAPT IASQPLSLRP EACRPAAGGA VHTRGLDFAC DIYIWAPLAG TCGVLLLSLV  180
ITLYCNHRNR RRVCKCPRPV VKSGDKPSLS ARYV                              214

SEQ ID NO: 19          moltype = DNA  length = 657
FEATURE                Location/Qualifiers
source                 1..657
                       mol_type = unassigned DNA
                       organism = Homo sapiens
SEQUENCE: 19
atgcatcgcc cccgaagacg cggtactaga ccccaccc tcgcccttct ggcagccctt    60
ctgctgccg cccgaggcgc tgacgccctt caacaaacac ccgactacat taaagtccaa  120
acaaacaaaa tggtaatgct gtcctgtgaa gctaagatat ccctttcaaa tatgcgcatt 180
tactggctta gacaaagaca agcccagc tcagactcac accatgaatt tctcgccctc   240
tgggattccg caaaaggtac catccatgga gaagaagtag aacaagaaaa aattgcagta  300
ttccgagatg ccagtcgatt catcctcaat ctgacttcag ttaaacccga agatagcggt  360
atctactttt gcatgatcgt tggctcacca gaactcacct tcggtaaagg aacccaattg  420
tccgtcgtcg atttcctgcc cactacagcc caacctacca aaaagtcaac ccttaagaag  480
agagtttgca gactgcccag acccgaaaca cagaaaggac ccctctgctc tcctattaca  540
cttggcttgc tcgtcgctgg agtcctcgtc cttcttgtat cccttggagt tgccattcac  600
ctgtgttgta gacgccgccg cgccagactc cggtttatga agcagtttta caaatga     657

SEQ ID NO: 20          moltype = AA  length = 189
FEATURE                Location/Qualifiers
source                 1..189
                       mol_type = protein
                       organism = Homo sapiens
SEQUENCE: 20
LQQTPAYIKV QTNKMVMLSC EAKISLSNMR IYWLRQRQAP SSDSHHEFLA LWDSAKGTIH   60
GEEVEQEKIA VFRDASRFIL NLTSVKPEDS GIYFCMIVGS PELTFGKGTQ LSVVDFLPTT  120
AQPTKKSTLK KRVCRLPRPE TQKGPLCSPI TLGLLVAGVL VLLVSLGVAI HLCCRRRRAR  180
LRFMKQFYK                                                          189
```

What is claimed is:

1. A composition comprising:

(i) a radiolabeled antibody conjugate comprising an antibody or antigen binding fragment thereof that binds CD8, a chelating moiety, and a positron emitter, wherein the antibody or antigen-binding fragment thereof comprises three heavy chain CDRs (HCDR1, HCDR2, and HCDR3) contained within a heavy chain variable region (HCVR) amino acid sequence of SEQ ID NO: 2; and three light chain CDRs (LCDR1, LCDR2, and LCDR3) contained within a light chain variable region (LCVR) amino acid sequence of SEQ ID NO: 10; and (ii) CD8 expressing T cells.

2. The composition of claim 1, wherein the positron emitter is $^{89}$Zr.

3. The composition of claim 1, wherein the chelating moiety is desferrioxamine.

4. The composition of claim 1, wherein the chelating moiety is

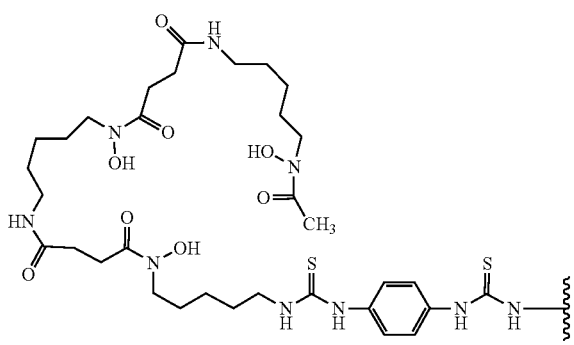 [SMILES: *CNC(=S)Nc1ccc(NC(=S)NCCCCCN(O)C(=O)CCC(=O)NCCCCCN(O)C(=O)CCC(=O)NCCCCCN(O)C(C)=O)cc1]

wherein

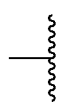

is a covalent bond to the antibody or antigen-binding fragment thereof.

5. The composition of claim 1, wherein the radiolabeled antibody conjugate has a chelating moiety to antibody ratio (DAR) of from 1.0 to 2.0.

6. The composition of claim 5, wherein the chelating moiety-to-antibody ratio is about 1.7.

7. The composition of claim 1, wherein the antibody or antigen-binding fragment thereof comprises an HCDR1 comprising the amino acid sequence of SEQ ID NO: 4; an HCDR2 comprising the amino acid sequence of SEQ ID NO: 6; an HCDR3 comprising the amino acid sequence of SEQ ID NO: 8; an LCDR1 comprising the amino acid sequence of SEQ ID NO: 12; an LCDR2 comprising the amino acid sequence of SEQ ID NO: 14; and an LCDR3 comprising the amino acid sequence of SEQ ID NO: 16.

8. The composition of claim 1, wherein the antibody or antigen-binding fragment thereof comprises an HCVR having an amino acid sequence as set forth in SEQ ID NO: 2 and an LCVR having an amino acid sequence as set forth in SEQ ID NO: 10.

9. A method of identifying a subject for anti-tumor therapy with an anti-PD-1 antibody, or an antigen-binding fragment thereof, or an anti-PD-L1 antibody, or an antigen-binding fragment thereof, comprising:
determining a presence of CD8+ T-cells in a tumor by:
(i) administering a radiolabeled anti-CD8 antibody conjugate to the tumor,
wherein the radiolabeled anti-CD8 antibody conjugate comprises an antibody or antigen-binding fragment thereof that binds CD8, a chelating moiety, and a positron emitter, wherein the antibody or antigen-binding fragment thereof comprises three heavy chain CDRs (HCDR1, HCDR2, and HCDR3) contained within a heavy chain variable region (HCVR) amino acid sequence of SEQ ID NO: 2; and three light chain CDRs (LCDR1, LCDR2, and LCDR3) contained within a light chain variable region (LCVR) amino acid sequence of SEQ ID NO: 10; and
(ii) visualizing the presence of CD8+ T-cells by positron emission tomography (PET) imaging;
wherein the presence of CD8+ T cells in the tumor identifies the subject for selection for anti-tumor therapy with an anti-PD-1 antibody, or an antigen-binding fragment thereof, or an anti-PD-L1 antibody, or an antigen-binding fragment thereof.

10. The method of claim 9, wherein the positron emitter is $^{89}$Zr.

11. The method of claim 9, wherein the chelating moiety is desferrioxamine.

12. The method of claim 9, wherein the antibody or antigen-binding fragment thereof comprises an HCDR1 comprising the amino acid sequence of SEQ ID NO: 4; an HCDR2 comprising the amino acid sequence of SEQ ID NO: 6; an HCDR3 comprising the amino acid sequence of SEQ ID NO: 8; an LCDR1 comprising the amino acid sequence of SEQ ID NO: 12; an LCDR2 comprising the amino acid sequence of SEQ ID NO: 14; and an LCDR3 comprising the amino acid sequence of SEQ ID NO: 16.

13. The method of claim 9, wherein the antibody or antigen-binding fragment thereof comprises an HCVR having an amino acid sequence as set forth in SEQ ID NO: 2 and an LCVR having an amino acid sequence as set forth in SEQ ID NO: 10.

14. The method of claim 9, wherein the anti-tumor therapy is an anti-PD-1 antibody or antigen-binding fragment thereof selected from the group consisting of REGN2810, nivolumab, and pembrolizumab.

15. The method of claim 9, wherein the anti-tumor therapy is an anti-PD-1 antibody or antigen-binding fragment thereof and the anti-PD-1 antibody or antigen-binding fragment thereof is REGN2810.

16. The method of claim 9, wherein the anti-tumor therapy is an anti-PD-L1 antibody or antigen-binding fragment thereof and the anti-PD-L1 antibody or antigen-binding fragment thereof is atezolizumab, avelumab, or durvalumab.

17. The method of claim 9, wherein the tumor is selected from the group consisting of blood cancer, brain cancer, renal cell cancer, ovarian cancer, bladder cancer, prostate cancer, breast cancer, hepatic cell carcinoma, bone cancer, colon cancer, non-small-cell lung cancer, squamous cell carcinoma of head and neck, colorectal cancer, mesothelioma, B cell lymphoma, and melanoma.

18. A labeling agent comprising:

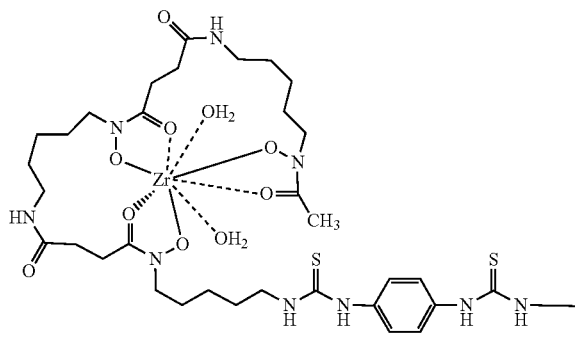

and wherein Zr is the positron emitter Zr$^{89}$, connected to an anti-CD8 antibody or antigen-binding fragment thereof, wherein the anti-CD8 antibody or antigen-binding fragment thereof is a weak blocker of CD8+ T-cell function, and wherein the antibody or antigen-binding fragment thereof comprises an HCDR1 comprising the amino acid sequence of SEQ ID NO: 4; an HCDR2 comprising the amino acid sequence of SEQ ID NO: 6; an HCDR3 comprising the amino acid sequence of SEQ ID NO: 8; an LCDR1 comprising the amino acid sequence of SEQ ID NO: 12; an LCDR2 comprising the amino acid sequence of SEQ ID NO: 14; and an LCDR3 comprising the amino acid sequence of SEQ ID NO: 16.

19. The labeling agent of claim 18, wherein the antibody or antigen-binding fragment thereof comprises an HCVR having an amino acid sequence as set forth in SEQ ID NO: 2 and an LCVR having an amino acid sequence as set forth in SEQ ID NO: 10.

* * * * *